(12) United States Patent
Priepke et al.

(10) Patent No.: US 8,791,103 B2
(45) Date of Patent: Jul. 29, 2014

(54) CARBOXYLIC ACID AMIDES, THE PREPARATION THEREOF AND THEIR USE AS MEDICAMENTS

(71) Applicants: Henning Priepke, Warthausen (DE); Kai Gerlach, Mittelbiberach (DE); Roland Pfau, Biberach an der Riss (DE); Norbert Hauel, Schemmerhofen (DE); Iris Kauffmann-Hefner, Attenweiler (DE); Georg Dahmann, Warthausen-Birkenhard (DE); Herbert Nar, Ochsenhausen (DE); Sandra Handschuh, Biberach an der Riss (DE); Wolfgang Wienen, Biberach an der Riss (DE); Annette Schuler-Metz, Ulm (DE)

(72) Inventors: Henning Priepke, Warthausen (DE); Kai Gerlach, Mittelbiberach (DE); Roland Pfau, Biberach an der Riss (DE); Norbert Hauel, Schemmerhofen (DE); Iris Kauffmann-Hefner, Attenweiler (DE); Georg Dahmann, Warthausen-Birkenhard (DE); Herbert Nar, Ochsenhausen (DE); Sandra Handschuh, Biberach an der Riss (DE); Wolfgang Wienen, Biberach an der Riss (DE); Annette Schuler-Metz, Ulm (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 13/866,255

(22) Filed: Apr. 19, 2013

(65) Prior Publication Data
US 2013/0237522 A1    Sep. 12, 2013

Related U.S. Application Data

(60) Division of application No. 12/958,882, filed on Dec. 2, 2010, now Pat. No. 8,445,525, which is a division of application No. 11/960,222, filed on Dec. 19, 2007, now Pat. No. 7,947,700, which is a continuation of application No. 11/056,413, filed on Feb. 11, 2005, now Pat. No. 7,371,743.

(30) Foreign Application Priority Data

Feb. 28, 2004  (DE) ............... 10 2004 009 835
Dec. 18, 2004  (DE) ............... 10 2004 060 984

(51) Int. Cl.
*A01N 43/62* (2006.01)
*A61K 31/55* (2006.01)
*C07D 223/00* (2006.01)

(52) U.S. Cl.
USPC ............... 514/218; 540/484; 540/492

(58) Field of Classification Search
USPC .................. 540/484, 492; 514/218
See application file for complete search history.

(56) References Cited

U.S. PATENT DOCUMENTS

| | | | |
|---|---|---|---|
| 6,248,770 B1 | 6/2001 | Ries et al. |
| 6,451,832 B2 | 9/2002 | Ries et al. |
| 6,593,355 B2 | 7/2003 | Ries et al. |
| 6,747,023 B1 | 6/2004 | Kobayashi et al. |
| 6,943,179 B2 | 9/2005 | Mederski et al. |
| 7,157,456 B2 | 1/2007 | Straub et al. |
| 7,192,968 B2 | 3/2007 | Yoshino et al. |
| 7,199,133 B2 | 4/2007 | Dorsch et al. |
| 2002/0183519 A1 | 12/2002 | Nar et al. |
| 2003/0004356 A1 | 1/2003 | Ries et al. |
| 2004/0176603 A1 | 9/2004 | Priepke et al. |
| 2004/0220169 A1 | 11/2004 | Gillard et al. |
| 2004/0242660 A1 | 12/2004 | Straub et al. |
| 2005/0272792 A1 | 12/2005 | Gerlach et al. |
| 2013/0237522 A1 | 9/2013 | Priepke et al. |

FOREIGN PATENT DOCUMENTS

| | | |
|---|---|---|
| AU | 2003292239 A1 | 7/2004 |
| CA | 2393916 A1 | 7/2001 |

(Continued)

OTHER PUBLICATIONS

International Search Report for PCT/EP2005/001796 mailed on Jun. 13, 2005.
John J. Masters et al; Bicyclic S1-Binding Constructs in a Series of Phenyl Glycine-Based Inhibitors of Human Factor XA; Abstract Medi (2002) 284.
Wei He et al; Benzimidazoles and Isosteric Compounds as Potent and Selective Factor Xa Inhibitors; Bioorganic & Medicinal Chemistry Letters (2002) vol. 12 pp. 919-922; Elsevier Science Ltd.

(Continued)

*Primary Examiner* — Paul V. Ward
(74) *Attorney, Agent, or Firm* — Michael P. Morris; Usha R. Patel

(57) ABSTRACT

The present invention relates to new substituted carboxylic acid amides of general formula

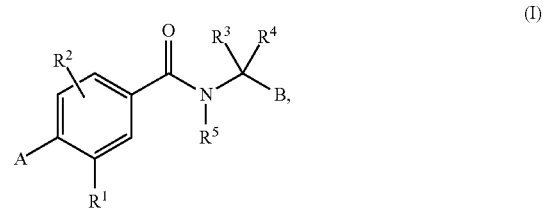

(I)

wherein A, B and $R^1$ to $R^5$ are defined as in claim 1, the tautomers, the enantiomers, the diastereomers, the mixtures thereof and the salts thereof, particularly the physiologically acceptable salts thereof with inorganic or organic acids or bases, which have valuable properties.

27 Claims, No Drawings

(56) References Cited

FOREIGN PATENT DOCUMENTS

| | | |
|---|---|---|
| CA | 2439231 A1 | 9/2002 |
| EP | 1106605 A1 | 6/2001 |
| WO | 0001704 A2 | 1/2000 |
| WO | 0009480 A1 | 2/2000 |
| WO | 0026197 A1 | 5/2000 |
| WO | 0054729 A2 | 9/2000 |
| WO | 0071512 A1 | 11/2000 |
| WO | 0076970 A2 | 12/2000 |
| WO | 0076971 A2 | 12/2000 |
| WO | 0119788 A2 | 3/2001 |
| WO | 0147896 A1 | 7/2001 |
| WO | 0147919 A1 | 7/2001 |
| WO | 0151456 A2 | 7/2001 |
| WO | 0156989 A2 | 8/2001 |
| WO | 0174774 A1 | 10/2001 |
| WO | 0196303 A1 | 12/2001 |
| WO | 0196304 A1 | 12/2001 |
| WO | 0196323 A1 | 12/2001 |
| WO | 0210154 A2 | 2/2002 |
| WO | 0226720 A2 | 4/2002 |
| WO | 0234711 A1 | 5/2002 |
| WO | 02057236 A1 | 7/2002 |
| WO | 02064567 A2 | 8/2002 |
| WO | 02072558 A1 | 9/2002 |
| WO | 02074735 A2 | 9/2002 |
| WO | 02074765 A1 | 9/2002 |
| WO | 03000256 A1 | 1/2003 |
| WO | 03026652 A1 | 4/2003 |
| WO | 03039543 A1 | 5/2003 |
| WO | 2004056784 A1 | 7/2004 |

OTHER PUBLICATIONS

Werner W. K. R. Mederski, et al; Halothiophene benzimidazoles as P1 surrogates of inhibitors of blood coagulation factor Xa; Bioorganic & Medicinal Chemistry Letters 14, vol. 14, pp. 3763-3769; Apr. 29, 2004; Elsevier "Publisher".

Mederski, Werner W.K.R. et al. "Halothiophene benzimidazoles as P1 surrogates of inhibitors of blood coagulation factor Xa" (2004) Bioorganic & Medicinal Chemistry Letters 14, pp. 3763-3769.

Zhao, Zuchun et al. "Design, Synthesis, and In Vitro Biological Activity of Benzimidazole Based Factor Xa Inhibitors" (2000) Bioorganic & Medicinal Chemistry Letters 10, pp. 963-966.

CARBOXYLIC ACID AMIDES, THE PREPARATION THEREOF AND THEIR USE AS MEDICAMENTS

This application is a divisional of U.S. Ser. No. 12/958,882 filed Dec. 2, 2010, which is a divisional of U.S. Ser. No. 11/960,222 filed Dec. 19, 2007, which claims priority to U.S. Ser. No. 11/056,413, filed Feb. 11, 2005, which claims priority to German Application DE 10 2004 009 835, filed on Feb. 28, 2004 and to German Application DE 10 2004 060 984, filed on Dec. 18, 2004, each of which is incorporated herein in its entirety.

FIELD OF THE INVENTION

The present invention relates to new substituted carboxylic acid amides of general formula

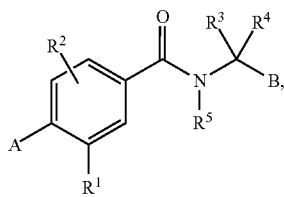

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

The present application thus relates to the new compounds of the above general formula I, the preparation thereof, the pharmaceutical compositions containing the pharmacologically effective compounds, the preparation and use thereof.

In the above general formula in a first embodiment
A denotes a group of general formula

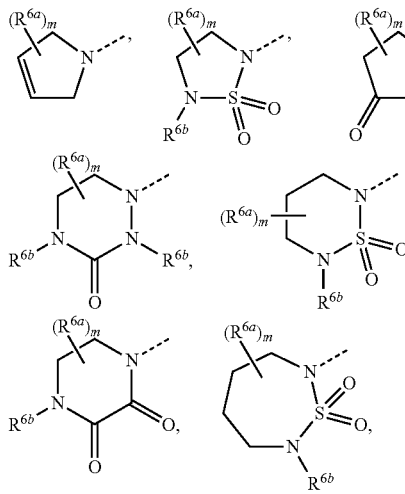

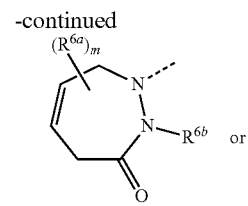

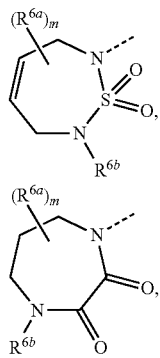

wherein
m denotes the number 1 or 2,
$R^{6a}$ independently of one another denotes a hydrogen, fluorine, chlorine or bromine atom or a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and
$R^{6b}$ independently of one another may be a hydrogen atom, a $C_{1-4}$-alkyl, $C_{1-4}$-alkylcarbonyl, $C_{1-4}$-alkyloxycarbonyl or $C_{1-3}$-alkylsulphonyl group, with the proviso that
in the above-mentioned substituted 5- to 7-membered groups A the heteroatoms optionally introduced as substituents are not separated from another heteroatom by precisely one carbon atom, or
a group of general formula

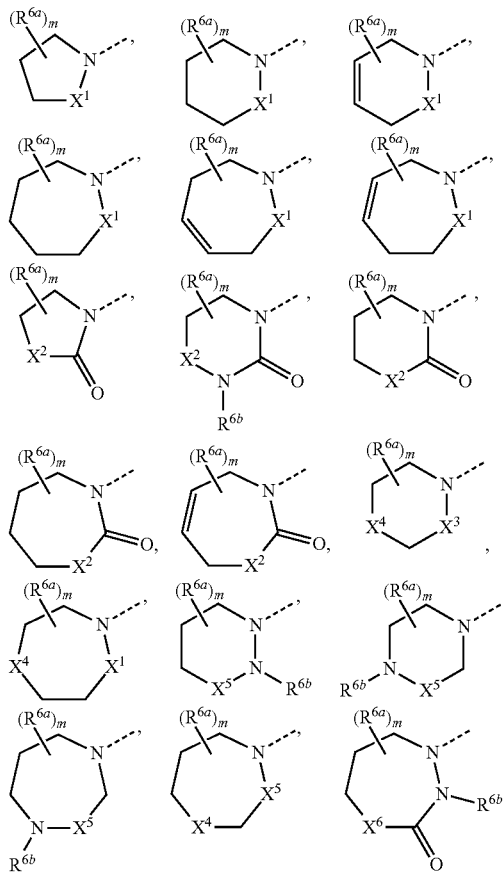

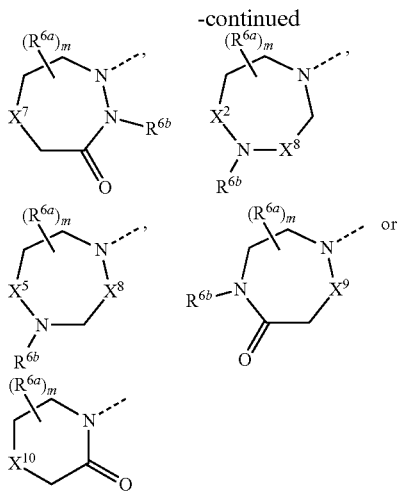

wherein
m denotes the number 1 or 2,
$X^1$ denotes an oxygen atom or a methylene, $-NR^{6b}-$, carbonyl or sulphonyl group,
$X^2$ denotes an oxygen atom or a $-NR^{6b}$ group,
$X^3$ denotes a methylene, carbonyl or sulphonyl group,
$X^4$ denotes an oxygen or sulphur atom, a $-NR^{6b}$ or carbonyl group,
$X^5$ denotes a carbonyl or sulphonyl group,
$X^6$ denotes an oxygen atom, a $-NR^{6b}$ or methylene group,
$X^7$ denotes an oxygen or sulphur atom or a $-NR^{6b}$ group,
$X^8$ denotes a methylene or carbonyl group,
$X^9$ denotes a $-NR^{6b}$ or carbonyl group,
$X^{10}$ denotes a sulphinyl or sulphonyl group and
$R^{6a}$ independently of one another denote a hydrogen, fluorine, chlorine or bromine atom or a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and
$R^{6b}$ independently of one another may be a hydrogen atom, a $C_{1-4}$-alkyl, $C_{1-4}$-alkylcarbonyl, $C_{1-4}$-alkoxycarbonyl or $C_{1-3}$-alkylsulphonyl group, with the proviso that
in the above-mentioned substituted 5- to 7-membered groups A the heteroatoms optionally introduced as substituents are not separated from another heteroatom by precisely one carbon atom,
$R^1$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, nitro, amino, $C_{1-3}$-alkoxy, a mono-, di- or trifluoromethoxy group,
$R^2$ denotes a hydrogen, fluorine, chlorine or bromine atom or a $C_{1-3}$-alkyl group,
$R^3$ denotes a hydrogen atom, a $C_{2-3}$-alkenyl or $C_{2-3}$-alkynyl group or a straight-chain or branched $C_{1-6}$-alkyl group wherein the hydrogen atoms may be wholly or partly replaced by fluorine atoms, and which is optionally substituted by a nitrile, hydroxy, a $C_{1-6}$-alkyloxy group wherein the hydrogen atoms may be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, mercapto, $C_{1-3}$-alkylsulphanyl, $C_{1-3}$-alkylsulphinyl, $C_{1-3}$-alkylsulphonyl, $C_{1-3}$-alkylcarbonylamino-$C_{1-3}$-alkylsulphanyl, $C_{1-3}$-alkylcarbonylamino-$C_{1-3}$-alkylsulphinyl, $C_{1-3}$-alkylcarbonylamino-$C_{1-}$ $_3$-alkylsulphonyl, carboxy, $C_{1-3}$-alkyloxycarbonyl, allyloxycarbonyl, propargyloxycarbonyl, benzyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-5}$-alkylcarbonylamino, $C_{1-3}$-alkyl-sulphonylamino, N—($C_{1-3}$-alkylsulphonyl)-$C_{1-3}$-alkylamino, $C_{3-6}$-cycloalkylcarbonyl-amino, aminocarbonylamino, $C_{1-3}$-alkylaminocarbonylamino, di-($C_{1-3}$-alkyl)-amino-carbonylamino, a 4- to 7-membered cycloalkyleneiminocarbonylamino, benzyl-oxycarbonylamino, phenylcarbonylamino or guanidino group,
a carboxy, aminocarbonyl, $C_{1-4}$-alkylaminocarbonyl, $C_{3-6}$-cycloalkylaminocarbonyl, di-($C_{1-3}$-alkyl)-aminocarbonyl, $C_{1-4}$-alkoxycarbonyl, $C_{4-6}$-cycloalkyleneiminocarbonyl group,
a phenyl or heteroaryl, phenylcarbonyl-$C_{1-3}$-alkyl, phenyl-$C_{1-3}$-alkyl or heteroaryl -$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, benzyloxy, carboxy-$C_{1-3}$-alkyloxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4- to 7-membered cycloalkyleneiminocarbonyl-$C_{1-3}$-alkoxy, carboxy, $C_{1-3}$-alkyloxycarbonyl or $C_{1-3}$-alkyloxycarbonylamino group,
a 3- to 7-membered cycloalkyl, cycloalkyleneimino, cycloalkyl-$C_{1-3}$-alkyl or cycloalkyleneimino-$C_{1-3}$-alkyl group wherein in the cyclic moiety a methylene group may be replaced by an —NH— group optionally substituted by a $C_{1-3}$-alkyl or $C_{1-3}$-alkylcarbonyl group or by an oxygen atom and wherein additionally a methylene group adjacent to the —NH—, —N($C_{1-3}$-alkylcarbonyl)- or —N($C_{1-3}$-alkyl)-group may be replaced in each case by a carbonyl or sulphonyl group, with the proviso that a cycloalkyleneimino group as hereinbefore defined wherein two nitrogen atoms are separated from one another by precisely one —CH$_2$— group is excluded,
$R^4$ denotes a hydrogen atom or a $C_{1-3}$-alkyl group or
$R^3$ and $R^4$ together with the carbon atom to which they are bound, denote a $C_{3-7}$-cycloalkyl group, while
one of the methylene groups of the $C_{3-7}$-cycloalkyl group may be replaced by an imino, $C_{1-3}$-alkylimino, acylimino or sulphonylimino group,
$R^5$ denotes a hydrogen atom or a $C_{1-3}$-alkyl group,
B denotes a group of formula

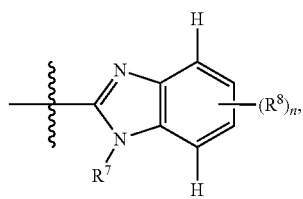

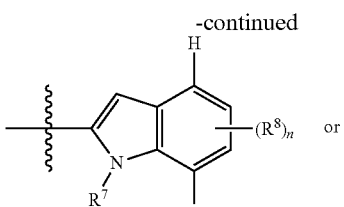

or

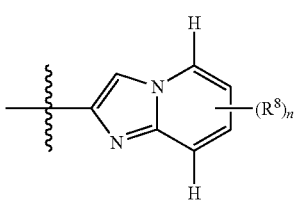

wherein
n denotes the number 1 or 2,

R[7] denotes a hydrogen atom or a $C_{1-3}$-alkyl, hydroxy, $C_{1-5}$-alkyloxycarbonyl, carboxy-$C_{1-3}$-alkyl, $C_{1-3}$-alkyloxycarbonyl-$C_{1-3}$-alkyl, amino or $C_{1-3}$-alkylamino group and R[8] independently of one another denote a hydrogen, fluorine, chlorine, bromine or iodine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy, amino, nitro or nitrile group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzoxazolyl, benzo[c]isoxazolyl, benzo[d]-isoxazolyl, benzo[1,2,5]oxadiazolyl, benzo[1,2,5]thiadiazolyl, benzo[1,2,3]thia-diazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-8}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl group.

Examples of the $C_{1-8}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy, neo-pentyloxy, 1-hexyloxy, 2-hexyloxy, 3-hexyloxy, 1-heptyloxy, 2-heptyloxy, 3-heptyloxy, 4-heptyloxy, 1-octyloxy, 2-octyloxy, 3-octyloxy or 4-octyloxy group.

By a group which can be converted in vivo into a carboxy group is meant for example a carboxy group esterified with an alcohol wherein the alcohol moiety is preferably a $C_{1-8}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bond to the oxygen atom starts from a carbon atom which carries a double or triple bond, a $C_{3-8}$-cycloalkyl-$C_{1-3}$-alkanol or an alcohol of formula $$R^9-CO-O-(R^{10}CR^{11})-OH,$$

wherein

R[9] denotes a $C_{1-8}$-alkyl, $C_{5-7}$-cycloalkyl, phenyl or phenyl-$C_{1-3}$-alkyl group, R[10] denotes a hydrogen atom, a $C_{1-3}$-alkyl, $C_{5-7}$-cycloalkyl or phenyl group and R[11] denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyl-oxy, n-pentyloxy, n-hexyloxy or cyclohexyloxy group or a phenyl-$C_{1-3}$-alkoxy group such as the benzyloxy group.

Those compounds of general formula I wherein R[3] contains a group which may be converted in vivo into a carboxy group are prodrugs for those compounds of general formula I wherein R[3] contains a carboxy group.

A 2nd embodiment of the present invention comprises those compounds of general formula I wherein A denotes a group of general formula

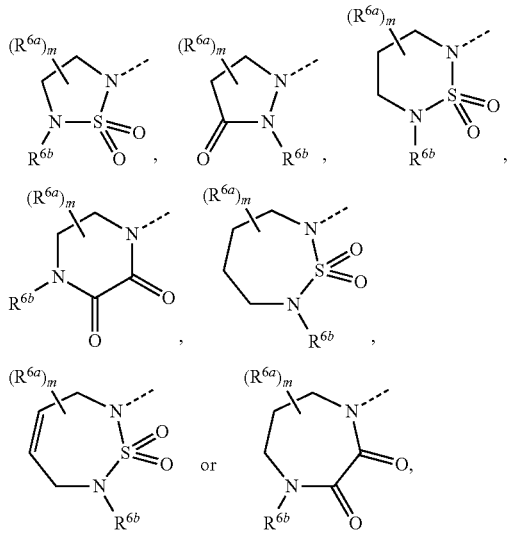

wherein m denotes the number 1 or 2, $R^{6a}$ independently of one another denote a hydrogen or fluorine atom, a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and $R^{6b}$ independently of one another may be a hydrogen atom, a $C_{1-4}$-alkyl, $C_{1-4}$-alkyl-carbonyl, $C_{1-4}$-alkoxycarbonyl or $C_{1-3}$-alkylsulphonyl group, with the proviso that
in the above-mentioned substituted 5- to 7-membered groups A the heteroatoms optionally introduced as substituents are not separated from another heteroatom by precisely one carbon atom, or a group of general formula

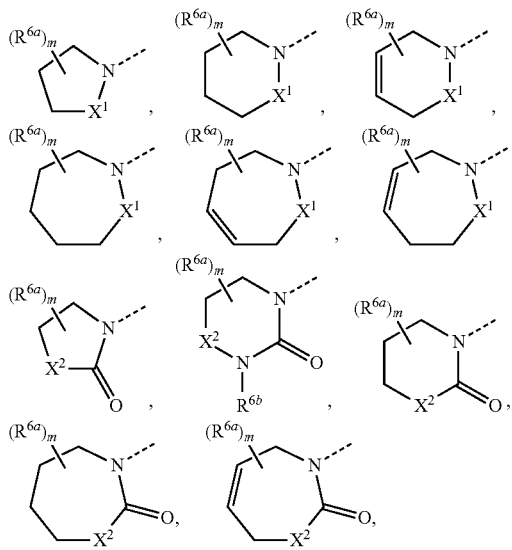

wherein
m denotes the number 1 or 2,
$X^1$ denotes a methylene, —$NR^{6b}$—, carbonyl or sulphonyl group,
$X^2$ denotes an oxygen atom or a —$NR^{6b}$ group,
$X^3$ denotes a methylene, carbonyl or sulphonyl group,
$X^4$ denotes an oxygen or sulphur atom, a —$NR^{6b}$ or carbonyl group,
$X^5$ denotes a carbonyl or sulphonyl group,
$X^8$ denotes a carbonyl group,
$X^9$ denotes a carbonyl group,
$R^{6a}$ independently of one another denote a hydrogen or fluorine atom, a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and
$R^{6b}$ independently of one another may be a hydrogen atom, a $C_{1-4}$-alkyl, $C_{1-4}$-alkylcarbonyl, $C_{1-4}$-alkoxycarbonyl or $C_{1-3}$-alkylsulphonyl group, with the proviso that
in the above-mentioned substituted 5- to 7-membered cyclic groups A the heteroatoms introduced as substituents are not separated from another heteroatom by precisely one carbon atom, $R^1$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, nitro, amino, $C_{1-3}$-alkoxy, a mono-, di- or trifluoromethoxy group, $R^2$ denotes a hydrogen, fluorine, chlorine or bromine atom or a $C_{1-3}$-alkyl group, $R^3$ denotes a $C_{2-3}$-alkenyl or $C_{2-3}$-alkynyl group or a straight-chain or branched $C_{1-8}$-alkyl group wherein the hydrogen atoms may be wholly or partly replaced by fluorine atoms, and which is optionally substituted by a nitrile, hydroxy, a $C_{1-5}$-alkyloxy group wherein the hydrogen atoms may be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, mercapto, $C_{1-3}$-alkylsulphanyl, $C_{1-3}$-alkylsulphinyl, $C_{1-3}$-alkylsulphonyl, $C_{1-3}$-alkylcarbonylamino-$C_{1-3}$-alkylsulphanyl, $C_{1-3}$-alkylcarbonylamino-$C_{1-3}$-alkylsulphinyl, $C_{1-3}$-alkylcarbonylamino-$C_{1-3}$-alkylsulphonyl, carboxy, $C_{1-3}$-alkyloxycarbonyl, allyloxycarbonyl, propargyloxycarbonyl, benzyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkyl-amino, di-($C_{1-3}$-alkyl)-amino, $C_{1-5}$-alkylcarbonylamino, $C_{1-3}$-alkylsulphonylamino, N—($C_{1-3}$-alkylsulphonyl)-$C_{1-3}$-alkylamino, $C_{3-6}$-cycloalkylcarbonylamino, aminocarbonylamino, $C_{1-3}$-alkylaminocarbonylamino, di-($C_{1-3}$-alkyl)-aminocarbonylamino, a 4- to 7-membered cycloalkyleneiminocarbonylamino, benzyloxycarbonylamino, phenylcarbonylamino or guanidino group, a carboxy, aminocarbonyl, $C_{1-4}$-alkylaminocarbonyl, $C_{3-6}$-cycloalkylaminocarbonyl, di-($C_{1-3}$-alkyl)-aminocarbonyl, $C_{1-4}$-alkoxycarbonyl, $C_{4-6}$-cycloalkyleneiminocarbonyl group, a phenyl or heteroaryl, phenylcarbonyl-$C_{1-3}$-alkyl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, benzyloxy, carboxy-$C_{1-3}$-alkyloxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4- to 7-membered cycloalkyleneiminocarbonyl-$C_{1-3}$-alkoxy, carboxy, $C_{1-3}$-alkyloxycarbonyl or $C_{1-3}$-alkyloxycarbonylamino group, a 3- to 7-membered cycloalkyl, cycloalkyleneimino, cycloalkyl-$C_{1-3}$-alkyl or cycloalkyleneimino-$C_{1-3}$-alkyl group wherein in the cyclic moiety a methylene group may be replaced by a —NH— group optionally substituted by a $C_{1-3}$-alkyl or $C_{1-3}$-alkylcarbonyl group or by an oxygen atom and wherein additionally a methylene group adjacent to the —NH—, —N($C_{1-3}$-alkylcarbonyl)- or —N($C_{1-3}$-alkyl)-group may be replaced in each case by a carbonyl or sulphonyl group, with the proviso that a cycloalkyleneimino group as hereinbefore defined wherein two nitrogen atoms are separated from one another by precisely one —CH$_2$— group is excluded, $R^4$ denotes a hydrogen atom or a $C_{1-3}$-alkyl group,
$R^5$ denotes a hydrogen atom or a $C_{1-3}$-alkyl group,
B denotes a group of formula

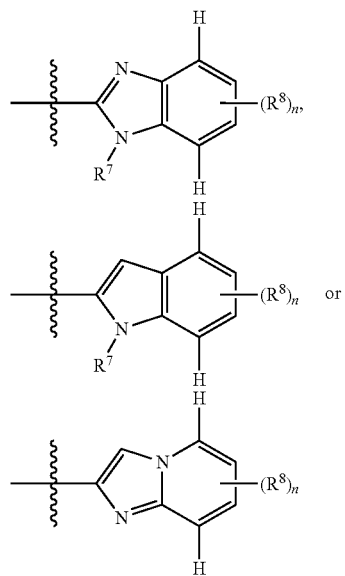

wherein
n denotes the number 1 or 2,
$R^7$ denotes a hydrogen atom, a $C_{1-3}$-alkyl, hydroxy, $C_{1-5}$-alkyloxycarbonyl, carboxy-$C_{1-3}$-alkyl, $C_{1-3}$-alkyloxycarbonyl-$C_{1-3}$-alkyl, amino or $C_{1-3}$-alkylamino group and $R^8$ independently of one another denote a hydrogen, fluorine, chlorine, bromine or iodine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy, amino, nitro or nitrile group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 3rd embodiment of the present invention comprises those compounds of general formula I, wherein
A denotes a group of general formula

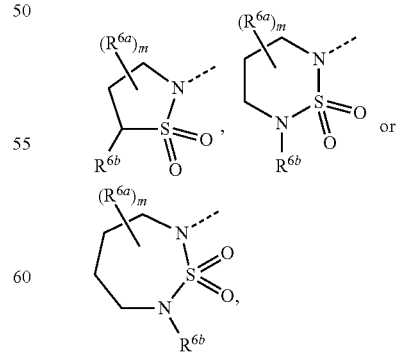

wherein m denotes the number 1 or 2,
$R^{6a}$ independently of one another denote a hydrogen or fluorine atom, a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and $R^{6b}$ independently of one another may be a hydrogen atom, a $C_{1-4}$-alkyl, $C_{1-4}$-alkyl-carbonyl, $C_{1-4}$-alkoxycarbonyl or $C_{1-3}$-alkylsulphonyl group, with the proviso that
in the above-mentioned substituted 5- to 7-membered groups A the heteroatoms optionally introduced as substituents are not separated from another heteroatom by precisely one carbon atom, or a group of general formula

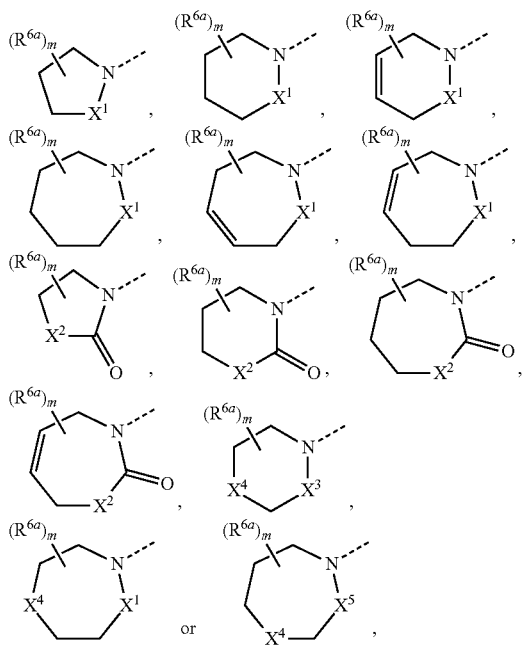

wherein
m denotes the number 1 or 2,
$X^1$ denotes a methylene, —$NR^{6b}$—, carbonyl or sulphonyl group,
$X^2$ denotes an oxygen atom or a —$NR^{6b}$ group,
$X^3$ denotes a methylene, carbonyl or sulphonyl group,
$X^4$ denotes an oxygen or sulphur atom or a —$NR^{6b}$ group,
$X^5$ denotes a carbonyl or sulphonyl group,
$R^{6a}$ independently of one another denote a hydrogen or fluorine atom, a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and
$R^{6b}$ independently of one another may be a hydrogen atom, a $C_{1-4}$-alkyl, $C_{1-4}$-alkylcarbonyl, $C_{1-4}$-alkoxycarbonyl or $C_{1-3}$-alkylsulphonyl group, with the proviso that
in the above-mentioned substituted 5- to 7-membered cyclic groups A the heteroatoms introduced as substituents are not separated from another heteroatom by precisely one carbon atom, $R^1$ denotes a fluorine, chlorine or bromine atom, a $C_{1-3}$-alkyl group wherein the hydrogen atoms may be wholly or partly replaced by fluorine atoms, a nitro, $C_{1-3}$-alkoxy, a mono-, di- or trifluoromethoxy group, $R^2$ denotes a hydrogen atom, $R^3$ denotes a straight-chain or branched $C_{1-6}$-alkyl group wherein the hydrogen atoms may be wholly or partly replaced by fluorine atoms, and which is optionally substituted by a nitrile, hydroxy, benzyloxy, a $C_{1-5}$-alkyloxy group wherein the hydrogen atoms may be wholly or partly replaced by fluorine atoms, an allyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, $C_{1-3}$-alkylsulphanyl, $C_{1-3}$-alkylsulphonyl, carboxy, $C_{1-3}$-alkyloxycarbonyl, $C_{1-3}$-alkylaminocarbonyl, di-($C_{1-3}$-alkyl)-aminocarbonyl, $C_{3-6}$-cycloalkyleneiminocarbonyl, aminocarbonylamino, $C_{1-3}$-alkylaminocarbonylamino or di-($C_{1-3}$-alkyl)-aminocarbonylamino group, an aminocarbonyl, $C_{1-4}$-alkylaminocarbonyl, $C_{3-6}$-cycloalkylaminocarbonyl or di-($C_{1-3}$-alkyl)-aminocarbonyl group, a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, carboxy, or $C_{1-3}$-alkyloxycarbonyl group, a 3- to 7-membered cycloalkyl group wherein in the cyclic moiety a methylene group may be replaced by a —NH— group optionally substituted by a $C_{1-3}$-alkyl or $C_{1-3}$-alkylcarbonyl group, or an oxygen atom, $R^4$ denotes a hydrogen atom, $R^5$ denotes a hydrogen atom, B denotes a group of formula

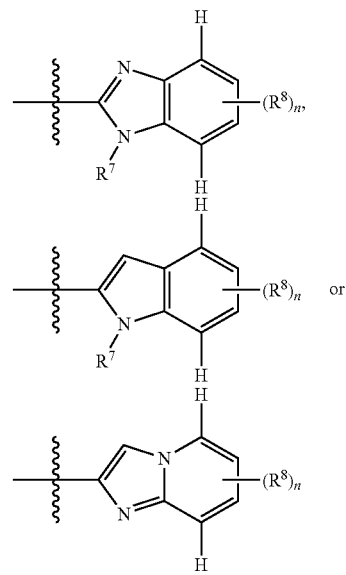

wherein
n denotes the number 1,
$R^7$ denotes a hydrogen atom and
$R^8$ denotes a hydrogen, fluorine, chlorine, bromine or iodine atom, a methyl, $C_{2-3}$-alkynyl, or methoxy group, wherein the hydrogen atoms may be wholly or partly replaced by fluorine atoms, while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl and alkoxy groups contained in the abovementioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 4th embodiment of the present invention comprises those compounds of general formula I wherein A, $R^1$, $R^2$, $R^4$, $R^5$ and B are defined as described under the 3rd embodiment and $R^3$ denotes a straight-chain or branched $C_{1-6}$-alkyl group wherein the hydrogen atoms may be wholly or partly replaced by fluorine atoms, and which is optionally substituted by a nitrile, hydroxy, benzyloxy, a $C_{1-5}$-alkyloxy group wherein the hydrogen atoms may be wholly or partly replaced by fluorine atoms, an allyloxy, $C_{1-5}$-alkylcarbonyloxy, $C_{1-5}$-alkyloxycarbonyloxy, carboxy-$C_{1-3}$-alkyloxy, $C_{1-5}$-alkyl-oxycarbonyl-$C_{1-3}$-alkyloxy, $C_{1-8}$-alkyloxycarbonylamino, $C_{1-3}$-alkylsulphanyl, $C_{1-3}$-alkylsulphonyl, carboxy, $C_{1-3}$-alkyloxycarbonyl, $C_{1-3}$-alkylaminocarbonyl, di-($C_{1-3}$-alkyl)-aminocarbonyl, $C_{3-6}$-cycloalkyleneiminocarbonyl, aminocarbonylamino, $C_{1-3}$-alkylaminocarbonylamino or di-($C_{1-3}$-alkyl)-aminocarbonylamino group, an aminocarbonyl, $C_{1-4}$-alkylaminocarbonyl, $C_{3-6}$-cycloalkylaminocarbonyl or di-($C_{1-3}$-alkyl)-aminocarbonyl group, while the alkyl and alkoxy groups contained in the abovementioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 5th embodiment of the present invention comprises those compounds of general formula I wherein A, $R^1$, $R^2$, $R^4$, $R^5$ and B are defined as described under the 3rd embodiment and $R^3$ denotes a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, carboxy, or $C_{1-3}$-alkyloxycarbonyl group, a 3- to 7-membered cycloalkyl group wherein in the cyclic moiety a methylene group may be replaced by a —NH— group optionally substituted by a $C_{1-3}$-alkyl or $C_{1-3}$-alkylcarbonyl group, or by an oxygen atom, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 6th embodiment of the present invention comprises those compounds of general formula I, wherein A denotes a group of general formula

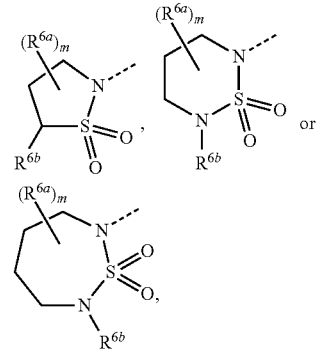

wherein m denotes the number 1 or 2, $R^{6a}$ independently of one another denote a hydrogen or fluorine atom or a $C_{1-3}$-alkyl group and $R^{6b}$ may be a hydrogen atom or a $C_{1-3}$-alkyl group, with the proviso that in the above-mentioned substituted 5- to 7-membered groups A the heteroatoms optionally introduced as substituents are not separated from another heteroatom by precisely one carbon atom, or a group of general formula

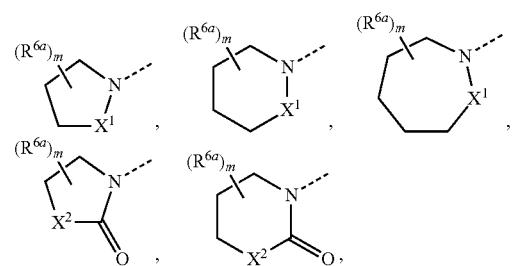

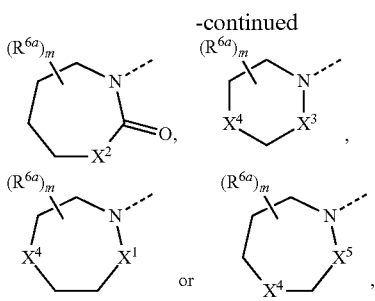

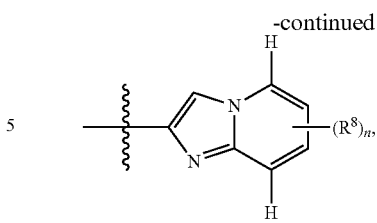

wherein
m denotes the number 1 or 2,
$X^1$ denotes a methylene, —$NR^{6b}$—, carbonyl or sulphonyl group,
$X^2$ denotes an oxygen atom or a —$NR^{6b}$ group,
$X^3$ denotes a methylene, carbonyl or sulphonyl group,
$X^4$ an oxygen or sulphur atom or a —$NR^{6b}$ group,
$X^5$ denotes a carbonyl or sulphonyl group,
$R^{6a}$ independently of one another denote a hydrogen or fluorine atom or a $C_{1-3}$-alkyl group and
$R^{6b}$ independently of one another may be a hydrogen atom or a $C_{1-3}$-alkyl group, with the proviso that
in the above-mentioned substituted 5- to 7-membered cyclic groups A the heteroatoms introduced as substituents are not separated from another heteroatom by precisely one carbon atom,
$R^1$ denotes a chlorine or bromine atom, a methyl or methoxy group, wherein the hydrogen atoms may be wholly or partly replaced by fluorine atoms, or a nitro group,
$R^2$ denotes a hydrogen atom,
$R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group,
a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, $C_{1-4}$-alkyloxy, mono-, di- or trifluoromethoxy, carboxy, or $C_{1-3}$-alkyloxycarbonyl group,
$R^4$ denotes a hydrogen atom,
$R^5$ denotes a hydrogen atom and
B denotes a group of formula

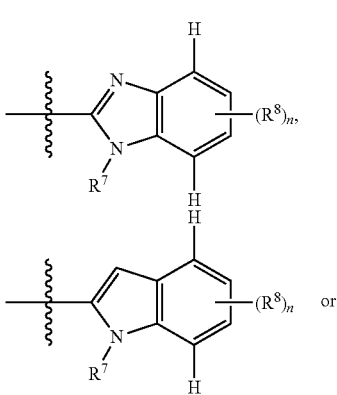

wherein
n denotes the number 1,
$R^7$ denotes a hydrogen atom and
$R^8$ denotes a chlorine or bromine atom or the ethynyl group,
while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a $C_{1-3}$-alkyl group, an oxygen or sulphur atom or
an imino group optionally substituted by a $C_{1-3}$-alkyl group or an oxygen or sulphur atom and additionally a nitrogen atom or
an imino group optionally substituted by a $C_{1-3}$-alkyl group and two or three nitrogen atoms,
and the bond is effected via a nitrogen atom or via a carbon atom,
while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
the tautomers, the enantiomers, the diastereomers, the mixtures thereof and the salts thereof.
A 7th embodiment of the present invention comprises those compounds of general formula I, wherein
A, $R^1$, $R^2$, $R^4$, $R^5$ and B are defined as described under the 6th embodiment and
$R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group,
while the alkyl and alkoxy groups contained in the abovementioned definitions which have more than two carbon atoms may, unless otherwise stated, be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
the tautomers, the enantiomers, the diastereomers, the mixtures thereof and the salts thereof.
An 8th embodiment of the present invention comprises those compounds of general formula I, wherein
A, $R^1$, $R^2$, $R^4$, $R^5$ and B are defined as described under the 6th embodiment and $R^3$ denotes a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, $C_{1-4}$-alkyloxy, mono-, di- or trifluoromethoxy, carboxy, or $C_{1-3}$-alkyloxycarbonyl group, a 3- to 7-membered cycloalkyl group wherein in the cyclic moiety a methylene group may be replaced by a —NH— group optionally substituted by a $C_{1-3}$-alkyl or $C_{1-3}$-alkylcarbonyl group, or by an oxygen atom, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 9th embodiment of the present invention comprises those compounds of general formula I, wherein A denotes a group of formula

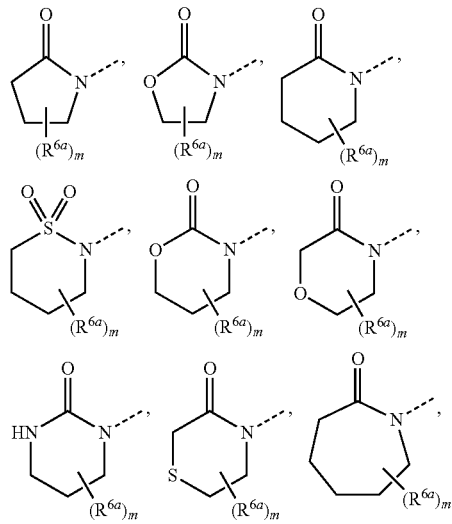

-continued

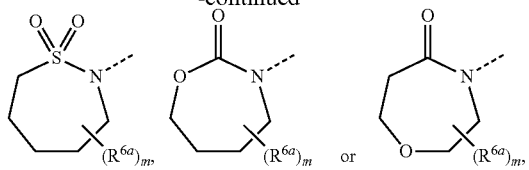

wherein
m denotes the number 1 or 2,
$R^{6a}$ independently of one another denote a hydrogen or fluorine atom or a $C_{1-3}$-alkyl group, with the proviso that in the above-mentioned substituted 5- to 7-membered cyclic groups A the fluorine atoms introduced as substituents are not separated from another heteroatom by precisely one carbon atom, $R^1$ denotes a chlorine or bromine atom, a methyl or methoxy group, wherein the hydrogen atoms may be wholly or partly replaced by fluorine atoms, or a nitro group, $R^2$ denotes a hydrogen atom, $R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group, a furanyl, thiophenyl, pyrrolyl, pyrazolyl, imidazolyl, oxazolyl, isoxazolyl, thiazolyl, pyridinyl, pyrimidinyl, pyrazinyl, pyridinyl-$C_{1-2}$-alkyl or imidazolyl-$C_{1-2}$-alkyl group which may optionally be substituted in the heteroaryl moiety by one or two $C_{1-3}$-alkyl groups, $C_{1-3}$-alkyloxy groups, carboxy or $C_{1-3}$-alkyloxycarbonyl groups, and $R^4$ denotes a hydrogen atom,
$R^5$ denotes a hydrogen atom and
B denotes a group of formula

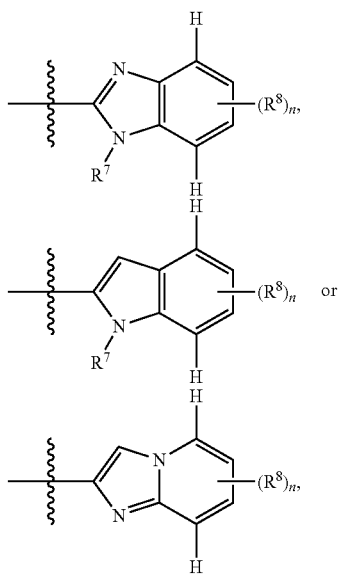

wherein
n denotes the number 1,
$R^7$ denotes a hydrogen atom and
$R^8$ denotes a chlorine or bromine atom or an ethynyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 10th embodiment of the present invention comprises those compounds of general formula I, wherein A, $R^1$, $R^2$, $R^4$, $R^5$ and B are defined as described under the 9th embodiment and $R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

An 11th embodiment of the present invention comprises those compounds of general formula I wherein A, $R^1$, $R^2$, $R^4$, $R^5$ and B are defined as described under the 9th embodiment and denote a furanyl, thiophenyl, pyrrolyl, pyrazolyl, imidazolyl, oxazolyl, isoxazolyl, thiazolyl, pyridinyl, pyrimidinyl, pyrazinyl, pyridinyl-$C_{1-2}$-alkyl or imidazolyl-$C_{1-2}$-alkyl group which may optionally be substituted in the heteroaryl moiety by one or two $C_{1-3}$-alkyl groups, wherein the hydrogen atoms may be wholly or partly replaced by fluorine atoms, $C_{1-3}$-alkyloxy groups, wherein the hydrogen atoms may be wholly or partly replaced by fluorine atoms, carboxy or $C_{1-3}$-alkyloxycarbonyl groups, and unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 12th embodiment of the present invention comprises those compounds of general formula I corresponding to the embodiments 1, 2, 3, 4, 5, 6, 7 and 8, wherein the group $X^1$ denotes a methylene group.

A 13th embodiment of the present invention comprises those compounds of general formula I corresponding to the embodiments 1, 2, 3, 4, 5, 6, 7 and 8, wherein the group $X^1$ denotes a carbonyl group.

A 14th embodiment of the present invention comprises those compounds of general formula I corresponding to the embodiments 1, 2, 3, 4, 5, 6, 7, 8, 12 and 13, wherein the group $X^3$ denotes a methylene group.

A 15th embodiment of the present invention comprises those compounds of general formula I corresponding to the embodiments 1, 2, 3, 4, 5, 6, 7, 8, 12 and 13 wherein the group $X^3$ denotes a carbonyl group.

A 16th embodiment of the present invention comprises those compounds of general formula I corresponding to the embodiments 1, 2, 3, 4, 5, 6, 7, 8, 12, 13, 14 and 15, wherein the group $X^4$ denotes an oxygen atom.

A 17th embodiment of the present invention comprises those compounds of general formula I corresponding to the embodiments 1, 2, 3, 4, 5, 6, 7, 8, 9, 10, 11, 12, 13, 14, 15 and 16, wherein the group B denotes the group

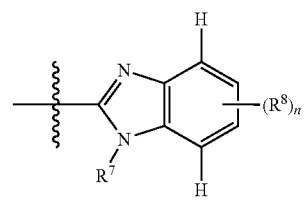

An 18th embodiment of the present invention comprises those compounds of general formula I corresponding to the embodiments 1, 2, 3, 4, 5, 6, 7, 8, 9, 10, 11, 12, 13, 14, 15 and 16, wherein the group B denotes the group

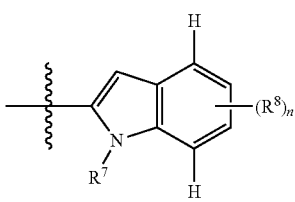

A 19th embodiment of the present invention comprises those compounds of general formula I corresponding to the embodiments 1, 2, 3, 4, 5, 6, 7, 8, 9, 10, 11, 12, 13, 14, 15 and 16, wherein the group B denotes the group

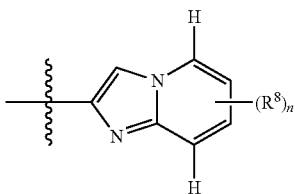

A 20th embodiment of the present invention comprises those compounds of general formula I corresponding to the embodiments 1, 2, 3, 4, 5, 6, 7, 8, 9, 10, 11, 12, 13, 14, 15, 16, 17, 18 and 19, wherein the group $R^8$ denotes a chlorine atom.

A 21st embodiment of the present invention comprises those compounds of general formula I corresponding to the embodiments 1, 2, 3, 4, 5, 6, 7, 8, 9, 10, 11, 12, 13, 14, 15, 16, 17, 18 and 19, wherein the group $R^8$ denotes a bromine atom.

A 22nd embodiment of the present invention comprises those compounds of general formula I corresponding to the embodiments 1, 2, 3, 4, 5, 6, 7, 8, 9, 10, 11, 12, 13, 14, 15, 16, 17, 18 and 19, wherein the group $R^8$ denotes an ethynyl group.

A 23rd embodiment of the present invention comprises those compounds of general formula I corresponding to the embodiments 1, 2, 3, 4, 5, 6, 7, 8, 9, 10, 11, 12, 13, 14, 15, 16, 17, 18, 19, 20, 21 and 22, which correspond to general formula Ia

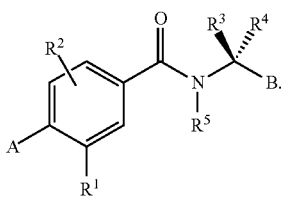

(Ia)

The following preferred compounds of general formula I will now be mentioned by way of example:
(1) 3-chloro-N-[(1S)-1-(5-chloro-1H-benzimidazol-2-yl)-ethyl]-4-([1,4]diazepan-1-yl)-benzamide,
(2) 4-(4-N-Boc-piperazin-1-yl)-N-[(1S)-1-(5-chloro-1H-benzimidazol-2-yl)-ethyl]-3-trifluoromethyl-benzamide,
(3) N-[(1S)-1-(5-chloro-1H-benzimidazol-2-yl)-ethyl]-4-(piperazin-1-yl)-3-trifluoromethyl-benzamide,
(4) N-[(1R)-1-(5-chloro-1H-benzimidazol-2-yl)-2-methoxy-ethyl)-4-(piperazin-1-yl)-3-trifluoromethyl-benzamide,
(5) 4-(4-N-acetyl-piperazin-1-yl)-N-[(1S)-1-(5-chloro-1H-benzimidazol-2-yl)-ethyl]-3-trifluoromethyl-benzamide,
(6) 4-(azepan-2-on-1-yl)-N-[(1S)-1-(5-chloro-1H-benzimidazol-2-yl)-ethyl]-3-methyl-benzamide,
(7) 4-(azepan-2-on-1-yl)-N-[(1R)-1-(5-chloro-1H-benzimidazol-2-yl)-2-methoxy-ethyl]-3-methyl-benzamide,
(8) 4-(azepan-2-on-1-yl)-N-[(1R)-1-(5-chloro-1H-benzimidazol-2-yl)-2-hydroxy-ethyl]-3-methyl-benzamide,
(9) N-[(1S)-1-(5-chloro-1H-benzimidazol-2-yl)-ethyl]-4-(pyrrolidin-2-on-1-yl)-benzamide,
(10) N-[(1S)-1-(5-chloro-1H-benzimidazol-2-yl)-ethyl]-3-methyl-4-(pyrrolidin-2-on-1-yl)-benzamide,
(11) N-[(1S)-1-(5-chloro-1H-benzimidazol-2-yl)-3-methyl-sulphanyl-propyl]-3-methyl-4-(pyrrolidin-2-on-1-yl)-benzamide,
(12) 3-chloro-N-[(1S)-1-(5-chloro-1H-benzimidazol-2-yl)-ethyl]-4-(4-N-methyl-[1,4]diazepan-1-yl)-benzamide,
(13) 3-chloro-N-[(1S)-1-(5-chloro-1H-benzimidazol-2-yl)-ethyl]-4-(2-methyl-pyrrolidin-1-yl)-benzamide,
(14) N-[(1S)-1-(5-chloro-1H-benzimidazol-2-yl)-ethyl]-3-chloro-4-(morpholin-1-yl)-benzamide,
(15) N-[(1S)-1-(5-chloro-1H-benzimidazol-2-yl)-ethyl]-3,5-difluoro-4-(morpholin-1-yl)-benzamide,
(16) N-[(1R)-1-(5-chloro-1H-benzimidazol-2-yl)-2-methoxy-ethyl]-3-trifluoromethyl-4-(morpholin-1-yl)-benzamide,
(17) 4-(azepan-1-yl)-N-[(1S)-1-(5-chloro-1H-benzimidazol-2-yl)-ethyl]-3-trifluoromethyl-benzamide,
(18) 4-(azepan-1-yl)-3-chloro-N-[(1S)-1-(5-chloro-1H-benzimidazol-2-yl)-ethyl]-benzamide,
(19) 3-chloro-N-[(1S)-1-(5-chloro-1H-benzimidazol-2-yl)-ethyl]-4-(piperidin-1-yl)-benzamide,
(20) 3-chloro-N-[(1S)-1-(5-chloro-1H-benzimidazol-2-yl)-ethyl]-4-([1,4]oxazepan-4-yl)-benzamide,
(21) N-[(1R)-1-(5-chloro-1H-benzimidazol-2-yl)-2-methoxy-ethyl]-4-(morpholin-3-on-4-yl)-3-trifluoromethyl-benzamide,
(22) N-[(1R)-1-(5-chloro-1H-benzimidazol-2-yl)-2-methoxy-ethyl]-3-methyl-4-(morpholin-3-on-4-yl)-benzamide,
(23) N-[(1S)-1-(5-chloro-1H-benzimidazol-2-yl)-ethyl]-3-methyl-sulphanyl-propyl]-3-methyl-4-(morpholin-3-on-4-yl)-benzamide,
(24) N-[(1R)-1-(5-chloro-1H-benzimidazol-2-yl)-2-hydroxy-ethyl]-3-methyl-4-(morpholin-3-on-4-yl)-benzamide,
(25) 4-(azepan-2-on-1-yl)-3-chloro-N-[(1R)-1-(5-chloro-1H-benzimidazol-2-yl)-2-methoxy-ethyl]-benzamide,
(26) 4-(azepan-2-on-1-yl)-N-[(1R)-1-(5-chloro-1H-benzimidazol-2-yl)-2-methoxy-ethyl]-3-trifluoromethyl-benzamide,
(27) N-[(1S)-1-(5-chloro-1H-benzimidazol-2-yl)-ethyl]-4-(morpholin-3-on-4-yl)-benzamide,
(28) N-[(1S)-1-(5-chloro-1H-benzimidazol-2-yl)-ethyl]-3-methyl-4-(morpholin-3-on-4-yl)-benzamide,
(29) N-[(1S)-1-(5-chloro-1H-benzimidazol-2-yl)-ethyl]-4-(morpholin-3-on-4-yl)-benzamide,
(30) N-[(1S)-1-(5-chloro-1H-benzimidazol-2-yl)-ethyl]-3-methyl-4-(piperazin-1-yl)-benzamide,
(31) N-[(1S)-1-(5-chloro-1H-benzimidazol-2-yl)-ethyl]-3-methyl-4-(piperazin-2-on-1-yl)-benzamide,
(32) N-[(1S)-1-(5-chloro-1H-benzimidazol-2-yl)-ethyl]-3-methyl-4-(piperidin-2-on-1-yl)-benzamide,
(33) N-[(1S)-1-(5-chloro-1H-benzimidazol-2-yl)-ethyl]-4-(N-methyl-piperazin-1-yl)-3-trifluoromethyl-benzamide,
(34) N-[(1S)-1-(5-chloro-1H-benzimidazol-2-yl)-3-methyl-sulphonyl-propyl]-3-methyl-4-(morpholin-3-on-4-yl)-benzamide,
(35) N-[(1S)-1-(5-chloro-1H-benzimidazol-2-yl)-3-methyl-sulphanyl-propyl]-4-(pyrrolidin-2-on-1-yl)-benzamide,

(36) N-[1-(5-chloro-1H-benzimidazol-2-yl)-1-phenyl-methyl]-4-(pyrrolidin-2-on-1-yl)-benzamide,
(37) N-[(1S)-1-(5-chloro-1H-benzimidazol-2-yl)-ethyl]-4-(3,5-dimethylpiperidin-1-yl)-benzamide,
(38) 3-chloro-N-[(1S)-1-(5-chloro-1H-benzimidazol-2-yl)-ethyl]-4-(3,4-didehydro-piperidin-1-yl)-benzamide,
(39) N-[(1S)-1-(5-chloro-1H-benzimidazol-2-yl)-ethyl]-3-methyl-4-([1,3]oxazepan-2-on-3-yl)-benzamide
(40) N-[(1S)-1-(5-chloro-1H-benzimidazol-2-yl)-3-methylsulphanyl-propyl)-4-(piperazin-1-yl)-3-trifluoromethyl-benzamide,
(41) N-[(1S)-1-(5-chloro-1H-benzimidazol-2-yl)-3-methylsulphanyl-propyl]-4-(morpholin-3-on-4-yl)-3-nitro-benzamide,
(42) 3-chloro-N-[(1S)-1-(5-chloro-1H-benzimidazol-2-yl)-ethyl]-4-(tetrahydro-pyrimidin-2-on-1-yl)-benzamide,
(43) N-[(1R)-1-(5-chloro-1H-benzimidazol-2-yl)-2-methoxy-ethyl]-3-methyl-4-([1,3]oxazepan-2-on-3-yl)-benzamide,
(44) 3-chloro-N-[(1R)-1-(5-chloro-1H-benzimidazol-2-yl)-2-methoxy-ethyl]-4-([1,4]oxazepan-5-on-4-yl)-benzamide,
(45) 3-chloro-N-[(1R)-1-(5-chloro-1H-benzimidazol-2-yl)-2-methoxy-ethyl]-4-([1,4]oxazepan-3-on-4-yl)-benzamide,
(46) 3-chloro-N-[(1R)-1-(5-chloro-1H-benzimidazol-2-yl)-2-methoxy-ethyl]-4-(piperidin-2-on-1-yl)-benzamide,
(47) N-[(1R)-1-(5-bromo-1H-benzimidazol-2-yl)-2-hydroxy-ethyl]-3-methyl-4-(morpholin-3-on-4-yl)-benzamide,
(48) N-[(1S)-1-(5-chloro-1H-benzimidazol-2-yl)-ethyl]-4-(1,1-dioxo-isothiazolidin-2-yl)-3-methyl-benzamide,
(49) N-[1-(5-chloro-1H-indol-2-yl)-ethyl]-3-methyl-4-(morpholin-3-on-4-yl)-benzamide,
(50) 3-chloro-N-[(1S)-1-(5-chloro-1H-benzimidazol-2-yl)-ethyl]-4-[2-(4-methyl-piperazin-1-yl-methyl)-piperidin-1-yl]-benzamide,
(51) N-[(1S)-1-(5-chloro-1H-benzimidazol-2-yl)-ethyl]-3-methyl-4-(oxazolidin-2-on-3-yl)-benzamide,
(52) 3-chloro-N-[(1S)-1-(5-chloro-1H-benzimidazol-2-yl)-ethyl]-4-(morpholin-3-on-4-yl)-benzamide,
(53) N-[(1R,2S)-1-(5-chloro-1H-benzimidazol-2-yl)-2-methoxy-propyl]-3-methyl-4-(morpholin-3-on-4-yl)-benzamide,
(54) N-[(1S)-1-(5-chloro-1H-benzimidazol-2-yl)-ethyl]-4-(3,5-dimethylpiperidin-1-yl)-benzamide,
(55) N-[(1S)-1-(5-chloro-1H-benzimidazol-2-yl)-ethyl]-3-methyl-4-(thiomorpholin-3-on-4-yl)-benzamide,
(56) N-[(1R)-1-(5-chloro-1H-benzimidazol-2-yl)-2-methoxy-ethyl]-3-methyl-4-(piperidin-2-on-1-yl)-benzamide,
(57) N-[(1S)-1-(5-chloro-1H-benzimidazol-2-yl)-ethyl]-3-methyl-4-([1,3]-oxazinan-2-on-3-yl)-benzamide,
(58) N-[(1R)-1-(5-chloro-1H-benzimidazol-2-yl)-2-methoxy-ethyl]-3-methyl-4-([1,3]-oxazinan-2-on-3-yl)-benzamide,
(59) N-[(1R)-1-(5-chloro-1H-benzimidazol-2-yl)-2-methoxy-ethyl]-4-(piperidin-2-on-1-yl)-3-trifluoromethyl-benzamide,
(60) N-[(1R)-1-(5-chloro-1H-benzimidazol-2-yl)-2-methoxy-ethyl]-4-(1,1-dioxo-[1,2]thiazinan-2-yl)-3-methyl-benzamide,
(61) N-[(1S)-1-(5-chloro-1H-benzimidazol-2-yl)-ethyl]-3-methyl-4-(5,6-didehydro-azepan-2-on-1-yl)-benzamide,
(62) 4-(azepan-2-on-1-yl)-N-[(1S)-1-(5-chloro-6-fluoro-1H-benzimidazol-2-yl)-ethyl]-3-methyl-benzamide,
(63) N-[(1S)-1-(5-chloro-1H-benzimidazol-2-yl)-ethyl]-4-(1,3-dioxo-thiomorpholin-4-yl)-3-methyl-benzamide,
(64) N-[(1S)-1-(5-chloro-1H-benzimidazol-2-yl)-ethyl]-3-methyl-4-(1,1,3-trioxo-thiomorpholin-4-yl)-benzamide,
(65) N-[(1R)-1-(5-chloro-1H-benzimidazol-2-yl)-2-methoxy-ethyl]-3-methyl-4-(piperazin-1-yl)-benzamide,
(66) N-[(1R)-1-(5-chloro-1H-benzimidazol-2-yl)-2-methoxy-ethyl]-3-methyl-4-(piperazin-2-on-1-yl)-benzamide,
(67) N-[(1S)-1-(5-chloro-1H-benzimidazol-2-yl)-butyl]-3-methyl-4-(morpholin-3-on-4-yl)-benzamide,
(68) N-[(1R)-1-(5-chloro-1H-benzimidazol-2-yl)-2-methoxy-ethyl]-4-([1,3]oxazepan-2-on-3-yl)-3-trifluoromethyl-benzamide,
(69) N-[(1S)-1-(5-chloro-1H-benzimidazol-2-yl)-ethyl]-3-methoxy-4-(piperidin-2-on-1-yl)-benzamide,
(70) N-[(1R)-1-(5-chloro-1H-benzimidazol-2-yl)-2-methoxy-ethyl]-3-methoxy-4-(piperidin-2-on-1-yl)-benzamide,
(71) N-[(1R)-1-(5-chloro-1H-benzimidazol-2-yl)-2-methoxy-ethyl]-4-(1,1-dioxo-[1,2,6]thiadiazinan-2-yl)-3-methyl-benzamide,
(72) N-[(1S)-1-(5-chloro-1H-benzimidazol-2-yl)-ethyl]-4-(1,1-dioxo-[1,2,6]thiadiazinan-2-yl)-3-methyl-benzamide,
(73) N-[(1S)-1-(5-chloro-1H-benzimidazol-2-yl)-ethyl]-4-(1,1-dioxo-6-methyl-[1,2,6]thiadiazinan-2-yl)-3-methyl-benzamide,
(74) N-[(1R)-1-(5-chloro-1H-benzimidazol-2-yl)-2-methoxy-ethyl]-4-(1,1-dioxo-3-methyl-[1,2,6]thiadiazinan-2-yl)-3-methyl-benzamide,
(75) N-[(1R)-1-(5-bromo-1H-benzimidazol-2-yl)-2-methoxy-ethyl]-3-methyl-4-(morpholin-3-on-4-yl)-benzamide,
(76) N-[(1S)-1-(5-chloro-1H-benzimidazol-2-yl)-3-(1H-tetrazol-5-yl)-propyl]-3-methyl-4-(morpholin-3-on-4-yl)-benzamide,
(77) N-[(1S)-1-(5-chloro-1H-benzimidazol-2-yl)-3-methoxy-propyl]-3-methyl-4-(morpholin-3-on-4-yl)-benzamide,
(78) N-[1-(5-chloro-1H-benzimidazol-2-yl)-thiophen-3-yl-methyl]-3-methyl-4-(morpholin-3-on-4-yl)-benzamide,
(79) N-[(1R)-1-(5-chloro-1H-benzimidazol-2-yl)-2-methylsulphanyl-ethyl]-3-methyl-4-(morpholin-3-on-4-yl)-benzamide,
(80) N-[(1R)-1-(5-chloro-1H-benzimidazol-2-yl)-2-methoxy-ethyl]-3-methyl-4-(thiomorpholin-3-on-4-yl)-benzamide,
(81) 3-chloro-N-[(1R)-1-(5-chloro-1H-benzimidazol-2-yl)-2-methoxy-ethyl]-4-(morpholin-3-on-4-yl)-benzamide,
(82) 3-chloro-N-[(1S)-1-(5-chloro-1H-benzimidazol-2-yl)-ethyl]-4-(3,6-dihydro-[1,2]oxazin-2-yl)-benzamide,
(83) 3-chloro-N-[(1R)-1-(5-chloro-1H-benzimidazol-2-yl)-2-methoxy-ethyl]-4-(1,1-dioxo-[1,2]thiazinan-2-yl)-benzamide,
(84) N-[(1R)-1-(5-chloro-1H-benzimidazol-2-yl)-2-methoxy-ethyl]-4-(1,1-dioxo-[1,2]thiazepan-2-yl)-3-methyl-benzamide,
(85) N-[(1S)-1-(5-chloro-1H-benzimidazol-2-yl)-ethyl]-4-(piperidin-2-on-1-yl)-3-trifluoromethoxy-benzamide,
(86) 3-bromo-N-[(1S)-1-(5-chloro-1H-benzimidazol-2-yl)-ethyl]-4-(piperidin-2-on-1-yl)-benzamide,
(87) 3-bromo-N-[(1R)-1-(5-chloro-1H-benzimidazol-2-yl)-2-methoxy-ethyl]-4-(piperidin-2-on-1-yl)-benzamide,
(88) N-[1-(5-chloro-1H-benzimidazol-2-yl)-1-(furan-2-yl)-methyl]-3-methyl-4-(piperidin-2-on-1-yl)-benzamide,
(89) 3-chloro-N-[(1S)-1-(5-chloro-1H-benzimidazol-2-yl)-ethyl]-4-([1,2]oxazinan-2-yl)-benzamide,

(90) N-[(1R)-1-(5-chloro-1H-benzimidazol-2-yl)-2-methoxy-ethyl]-3-methyl-4-(5-oxo-[1,4]oxazepan-4-yl)-benzamide,
(91) N-[(1S)-1-(5-chloro-1H-benzimidazol-2-yl)-ethyl]-4-(4,4-dimethyl-2-oxo-imidazolidin-1-yl)-3-methyl-benzamide,
(92) N-[(1R)-1-(5-chloro-1H-benzimidazol-2-yl)-2-methoxy-ethyl]-4-(4,4-dimethyl-2-oxo-imidazolidin-1-yl)-3-methyl-benzamide,
(93) 3-chloro-N-[(1S)-1-(5-chloro-1H-benzimidazol-2-yl)-ethyl]-4-(4-methyl-2-oxo-oxazolidin-3-yl)-benzamide,
(94) 3-chloro-N-[(1R)-1-(5-chloro-1H-benzimidazol-2-yl)-2-methoxy-ethyl]-4-(4-methyl-2-oxo-oxazolidin-3-yl)-benzamide,
(95) N-[1-(5-chloro-1H-benzimidazol-2-yl)-1-phenyl-methyl]-3-methyl-4-(morpholin-3-on-4-yl)-benzamide,
(96) N-[(1S)-1-(5-chloro-1H-benzimidazol-2-yl)-propyl]-3-methyl-4-(morpholin-3-on-4-yl)-benzamide,
(97) 3-bromo-N-[(1R)-1-(5-chloro-1H-benzimidazol-2-yl)-2-methoxy-ethyl]-4-(morpholin-3-on-4-yl)-benzamide,
(98) N-[(1S)-1-(5-chloro-1H-benzimidazol-2-yl)-ethyl]-3-methyl-4-(7-oxo-[1,4]diazepan-1-yl)-benzamide,
(99) N-[(1R)-1-(5-chloro-1H-benzimidazol-2-yl)-1-(thiophen-2-yl)-methyl]-3-methyl-4-(morpholin-3-on-4-yl)-benzamide,
(100) N-[(1R)-1-(5-bromo-1H-benzimidazol-2-yl)-2-hydroxy-ethyl]-4-(1,1-dioxo-[1,2]thiazinan-2-yl)-3-methyl-benzamide,
(101) N-[(1R)-1-(5-bromo-1H-benzimidazol-2-yl)-2-hydroxy-ethyl]-3-methyl-4-([1,3]oxazepan-2-on-3-yl)-benzamide,
(102) N-[(1R)-1-(5-chloro-1H-benzimidazol-2-yl)-2-methoxy-ethyl]-3-methyl-4-(4-(4S)-methyl-2-oxo-oxazolidin-3-yl)-benzamide,
(103) 3-chloro-N-[(1R)-1-(5-chloro-1H-benzimidazol-2-yl)-2-methoxy-ethyl]-4-(4,4-dimethyl-2-oxo-oxazolidin-3-yl)-benzamide,
(104) N-[(1R)-1-(5-chloro-1H-benzimidazol-2-yl)-2-methoxy-ethyl]-3-methyl-4-(4-(4R)-methyl-2-oxo-oxazolidin-3-yl)-benzamide,
(105) 3-chloro-N-[(1R)-1-(5-chloro-1H-benzimidazol-2-yl)-2-methoxy-ethyl]-4-(4-(4R)-ethyl-2-oxo-oxazolidin-3-yl)-benzamide,
(106) N-[(1R)-1-(5-chloro-1H-benzimidazol-2-yl)-2-methoxy-ethyl]-3-fluoro-4-(morpholin-3-on-4-yl)-benzamide,
(107) N-[1-(5-chloro-1H-benzimidazol-2-yl)-1-(1H-pyrazol-3-yl)-methyl]-3-methyl-4-(morpholin-3-on-4-yl)-benzamide,
(108) N-[1-(1S)-(5-chloro-1H-benzimidazol-2-yl)-2-cyanoethyl]-3-methyl-4-(morpholin-3-on-4-yl)-benzamide,
(109) N-[1-(5-chloro-1H-benzimidazol-2-yl)-1-pyridin-3-yl-methyl]-3-methyl-4-(morpholin-3-on-4-yl)-benzamide,
(110) N-[1-(5-chloro-1H-benzimidazol-2-yl)-1-(1H-1-methyl-pyrazol-3-yl)-methyl]-3-methyl-4-(morpholin-3-on-4-yl)-benzamide,
(111) 3-chloro-N-[(1R)-1-(5-chloro-1H-benzimidazol-2-yl)-2-methoxy-ethyl]-4-(5-methyl-morpholin-3-on-4-yl)-benzamide,
(112) 3-chloro-N-[(1S)-1-(5-chloro-1H-benzimidazol-2-yl)-ethyl]-4-(3-dimethylamino-pyrrolidin-1-yl)-benzamide,
(113) N-[(1S)-1-(5-chloro-1H-benzimidazol-2-yl)-ethyl]-4-(pyrazolidin-3-on-1-yl)-3-trifluoromethyl-benzamide,
(114) 3-chloro-N-[(1R)-1-(5-chloro-1H-benzimidazol-2-yl)-2-methoxy-ethyl]-4-(tetrahydro-pyrimidin-2-on-1-yl)-benzamide,
(115) N-[(1R)-1-(5-chloro-1H-benzimidazol-2-yl)-2-methoxy-ethyl]-3-chloro-4-([1,4]diazepan-1-yl)-benzamide,
(116) 3-chloro-N-[1-(5-chloro-1H-indol-2-yl)-2-methoxy-ethyl]-4-([1,4]diazepan-1-yl)-benzamide,
(117) N-[1-(5-chloro-1H-indol-2-yl)-2-methoxy-ethyl]-3-methyl-4-(morpholin-3-on-4-yl)-benzamide,
(118) 3-bromo-N-[1-(5-chloro-1H-indol-2-yl)-1-(furan-2-yl)-methyl]-4-([1,4]oxazepan-5-on-4-yl)-benzamide,
(119) N-[1-(5-bromo-1H-indol-2-yl)-1-(1-methyl-1H-pyrazol-3-yl)-methyl]-3-methyl-4-([1,3]oxazepan-2-on-3-yl)-benzamide,
(120) N-[1-(5-chloro-1H-indol-2-yl)-3-(methyl-sulphonyl)-propyl]-3-methyl-4-(tetrahydropyrimidin-2-on-1-yl)-benzamide,
(121) N-[1-(5-chloro-1H-indol-2-yl)-2-hydroxy-ethyl]-3-methyl-4-(5-methyl-pyrrolidin-2-on-1-yl)-benzamide,
(122) N-[1-(5-chloro-1H-indol-2-yl)-1-phenyl-methyl]-4-(piperazin-1-yl)-3-trifluoromethyl-benzamide,
(123) 4-(azepan-2-on-1-yl)-3-chloro-N-[1-(5-chloro-1H-indol-2-yl)-3-(1H-tetrazol-5-yl)-propyl]-benzamide,
(124) N-[1-(5-bromo-1H-indol-2-yl)-2-hydroxy-ethyl]-4-(1,1-dioxo-[1,2]thiazepan-2-yl)-3-methyl-benzamide,
(125) 3-chloro-N-[1-(7-chloro-imidazo[1,2a]pyridin-2-yl)-2-methoxy-ethyl]-4-(diazepan-1-yl)-benzamide,
(126) 3-chloro-N-[1-(7-chloro-imidazo[1,2a]pyridin-2-yl)-ethyl]-4-([1,4]oxazepan-5-on-4-yl)-benzamide,
(127) N-[(1S)-1-(7-chloro-imidazo[1,2a]pyridin-2-yl)-3-methyl-butyl]-3-methyl-4-(morpholin-3-on-4-yl)-benzamide,
(128) N-[1-(7-chloro-imidazo[1,2a]pyridin-2-yl)-2-methoxy-ethyl]-3-methyl-4-(morpholin-3-on-4-yl)-benzamide,
(129) 3-bromo-N-[1-(7-chloro-imidazo[1,2a]pyridin-2-yl)-1-(1H-pyrazol-3-yl)-methyl]-4-([1,4]oxazepan-5-on-4-yl)-benzamide,
(130) N-[1-(7-bromo-imidazo[1,2a]pyridin-2-yl)-2-hydroxy-ethyl]-3-chloro-4-(4-methyl-piperazin-1-yl)-benzamide,
(131) N-[1-(7-chloro-imidazo[1,2a]pyridin-2-yl)-2-hydroxy-ethyl]-3-methyl-4-(morpholin-3-on-4-yl)-benzamide,
(132) N-[1-(7-chloro-imidazo[1,2a]pyridin-2-yl)-1-(furan-2-yl)-methyl]-4-(diazepan-1-yl)-3-trifluoromethyl-benzamide,
(133) N-[1-(7-chloro-imidazo[1,2a]pyridin-2-yl)-1-phenyl-methyl]-3-methyl-4-(1,1-dioxo-[1,2]thiazepan-2-yl)-benzamide,
(134) 3-chloro-N-[1-(7-chloro-imidazo[1,2a]pyridin-2-yl)-2-methoxy-ethyl]-4-(morpholin-3-on-4-yl)-benzamide,
(135) 3-bromo-N-[1-(7-chloro-imidazo[1,2a]pyridin-2-yl)-3-(methyl-sulphanyl)-propyl]-4-([1,4]oxazepan-3-on-4-yl)-benzamide,
(136) 3-chloro-N-[1-(7-chloro-imidazo[1,2a]pyridin-2-yl)-2-hydroxy-ethyl]-4-(piperazin-2-on-1-yl)-benzamide,
(137) N-[1-(7-chloro-imidazo[1,2a]pyridin-2-yl)-2-methoxy-ethyl]-3-methyl-4-(piperidin-2-on-1-yl)-benzamide,
(138) N-[1-(7-bromo-imidazo[1,2a]pyridin-2-yl)-3-methoxy-propyl]-3-chloro-4-(1,1-dioxo-[1,2]thiazinan-2-yl)-benzamide,
(139) N-[1-(7-chloro-imidazo[1,2a]pyridin-2-yl)-2-trifluoromethoxy-ethyl]-3-methyl-4-([1,4]oxazepan-5-on-4-yl)-benzamide,
(140) N-[1-(5-chloro-1H-benzimidazol-2-yl)-3-methyl-butyl]-3-methyl-4-(morpholin-3-on-4-yl)-benzamide,
(141) N-[(1R)-1-(5-chloro-1H-benzimidazol-2-yl)-2-benzyloxy-ethyl]-3-methyl-4-(morpholin-3-on-4-yl)-benzamide, (142) N-[1-(5-chloro-1H-benzimidazol-2-yl)-3-benzyloxycarbonyl-propyl]-3-methyl-4-(morpholin-3-on-4-yl)-benzamide,
(143) N-[1-(5-chloro-1H-benzimidazol-2-yl)-3-hydroxycarbonyl-propyl]-3-methyl-4-(morpholin-3-on-4-yl)-benzamide,
(144) N-[1-(5-chloro-1H-benzimidazol-2-yl)-1-(pyrazin-2-yl)-methyl]-3-methyl-4-(morpholin-3-on-4-yl)-benzamide,
(145) N-[1-(5-chloro-1H-benzimidazol-2-yl)-1-(oxazol-2-yl)-methyl]-3-methyl-4-(morpholin-3-on-4-yl)-benzamide,
(146) N-[1-(5-chloro-1H-benzimidazol-2-yl)-1-(1H-imidazol-4-yl)-methyl]-3-methyl-4-(morpholin-3-on-4-yl)-benzamide,
(147) N[1-(5-bromo-1H-benzimidazol-2-yl)-2-methoxy-ethyl]-3-difluoromethoxy-4-(morpholin-3-on-4-yl)-benzamide,
(148) N[1-(5-chloro-1H-benzimidazol-2-yl)-1-methyl-ethyl]-3-methyl-4-(morpholin-3-on-4-yl)-benzamide,
(149) N-[3-(5-chloro-1H-benzimidazol-2-yl)-tetrahydrofuran-3-yl]-3-methyl-4-(morpholin-3-on-4-yl)-benzamide,
(150) N-[1-(5-chloro-1H-benzimidazol-2-yl)-3-(pyrrolidin-1-yl-carbonyl)-propyl]-3-methyl-4-(morpholin-3-on-4-yl)-benzamide,
(151) N-[1-(5-ethynyl-1H-benzimidazol-2-yl)-ethyl]-3-methyl-4-(morpholin-3-on-4-yl)-benzamide,
(152) N-[1-(5-ethynyl-1H-benzimidazol-2-yl)-2-methoxy-ethyl]-3-methyl-4-(morpholin-3-on-4-yl)-benzamide,
(153) N-[1-(5-ethynyl-1H-benzimidazol-2-yl)-2-methoxy-ethyl]-3-methyl-4-(piperidin-2-on-1-yl)-benzamide,
(154) 3-bromo-N-[1-(5-ethynyl-1H-benzimidazol-2-yl)-2-methoxy-ethyl]-4-(morpholin-3-on-4-yl)-benzamide,
(155) N-[1-(5-ethynyl-1H-benzimidazol-2-yl)-2-methoxy-ethyl]-3-methyl-4-(4-methyl-oxazolidin-2-on-3-yl)-benzamide,
(156) N-[1-(5-ethynyl-1H-benzimidazol-2-yl)-2-methoxy-ethyl]-3-methyl-4-([1,4]oxazepan-5-on-4-yl)-benzamide,
(157) N-[(1S)-1-(5-chloro-1H-benzimidazol-2-yl)-2-methoxy-ethyl]-3-methyl-4-(2-methyl-tetrahydropyridazin-1-yl)-benzamide, the tautomers, the enantiomers, the diastereomers, the mixtures thereof and the salts thereof, while the compounds (1) 4-(azepan-2-on-1-yl)-N-[(1R)-1-(5-chloro-1H-benzimidazol-2-yl)-2-methoxy-ethyl]-3-methyl-benzamide,
(2) 4-(azepan-2-on-1-yl)-N-[(1R)-1-(5-chloro-1H-benzimidazol-2-yl)-2-hydroxy-ethyl]-3-methyl-benzamide,
(3) N-[(1S)-1-(5-chloro-1H-benzimidazol-2-yl)-3-methylsulphanyl-propyl]-3-methyl-4-(pyrrolidin-2-on-1-yl)-benzamide,
(4) N-[(1R)-1-(5-chloro-1H-benzimidazol-2-yl)-2-methoxy-ethyl]-4-(morpholin-3-on-4-yl)-3-trifluoromethyl-benzamide,
(5) N-[(1R)-1-(5-chloro-1H-benzimidazol-2-yl)-2-methoxy-ethyl]-3-methyl-4-(morpholin-3-on-4-yl)-benzamide,
(6) N-[(1S)-1-(5-chloro-1H-benzimidazol-2-yl)-3-methylsulphanyl-propyl]-3-methyl-4-(morpholin-3-on-4-yl)-benzamide,
(7) N-[(1R)-1-(5-chloro-1H-benzimidazol-2-yl)-2-hydroxy-ethyl]-3-methyl-4-(morpholin-3-on-4-yl)-benzamide,
(8) 4-(azepan-2-on-1-yl)-3-chloro-N-[(1R)-1-(5-chloro-1H-benzimidazol-2-yl)-2-methoxy-ethyl]-benzamide,
(9) 4-(azepan-2-on-1-yl)-N-[(1R)-1-(5-chloro-1H-benzimidazol-2-yl)-2-methoxy-ethyl]-3-trifluoromethyl-benzamide,
(10) N-[(1S)-1-(5-chloro-1H-benzimidazol-2-yl)-ethyl]-3-methyl-4-([1,3]oxazepan-2-on-3-yl)-benzamide,
(11) N-[(1S)-1-(5-chloro-1H-benzimidazol-2-yl)-3-methylsulphanyl-propyl]-4-(morpholin-3-on-4-yl)-3-nitro-benzamide,
(12) N-[(1R)-1-(5-chloro-1H-benzimidazol-2-yl)-2-methoxy-ethyl]-3-methyl-4-([1,3]oxazepan-2-on-3-yl)-benzamide,
(13) 3-chloro-N-[(1R)-1-(5-chloro-1H-benzimidazol-2-yl)-2-methoxy-ethyl]-4-([1,4]oxazepan-5-on-4-yl)-benzamide,
(14) 3-chloro-N-[(1R)-1-(5-chloro-1H-benzimidazol-2-yl)-2-methoxy-ethyl]-4-(piperidin-2-on-1-yl)-benzamide,
(15) N-[(1R)-1-(5-bromo-1H-benzimidazol-2-yl)-2-hydroxy-ethyl]-3-methyl-4-(morpholin-3-on-4-yl)-benzamide,
(16) N-[(1R,2S)-1-(5-chloro-1H-benzimidazol-2-yl)-2-methoxy-propyl]-3-methyl-4-(morpholin-3-on-4-yl)-benzamide,
(17) N-[(1S)-1-(5-chloro-1H-benzimidazol-2-yl)-ethyl]-3-methyl-4-(thiomorpholin-3-on-4-yl)-benzamide,
(18) N-[(1R)-1-(5-chloro-1H-benzimidazol-2-yl)-2-methoxy-ethyl]-3-methyl-4-(piperidin-2-on-1-yl)-benzamide,
(19) N-[(1R)-1-(5-chloro-1H-benzimidazol-2-yl)-2-methoxy-ethyl]-3-methyl-4-([1,3]-oxazinan-2-on-3-yl)-benzamide,
(20) N-[(1R)-1-(5-chloro-1H-benzimidazol-2-yl)-2-methoxy-ethyl]-4-(piperidin-2-on-1-yl)-3-trifluoromethyl-benzamide,
(21) N-[(1R)-1-(5-chloro-1H-benzimidazol-2-yl)-2-methoxy-ethyl]-4-(1,1-dioxo-[1,2]thiazinan-2-yl)-3-methyl-benzamide,
(22) N-[(1S)-1-(5-chloro-1H-benzimidazol-2-yl)-butyl]-3-methyl-4-(morpholin-3-on-4-yl)-benzamide,
(23) N-[(1R)-1-(5-chloro-1H-benzimidazol-2-yl)-2-methoxy-ethyl]-4-([1,3]oxazepan-2-on-3-yl)-3-trifluoromethyl-benzamide,
(24) N-[(1R)-1-(5-chloro-1H-benzimidazol-2-yl)-2-methoxy-ethyl]-4-(1,1-dioxo-[1,2,6]thiadiazinan-2-yl)-3-methyl-benzamide,
(25) N-[(1R)-1-(5-bromo-1H-benzimidazol-2-yl)-2-methoxy-ethyl]-3-methyl-4-(morpholin-3-on-4-yl)-benzamide,
(26) N-[(1S)-1-(5-chloro-1H-benzimidazol-2-yl)-3-(1H-tetrazol-5-yl)-propyl]-3-methyl-4-(morpholin-3-on-4-yl)-benzamide,
(27) N-[(1S)-1-(5-chloro-1H-benzimidazol-2-yl)-3-methoxy-propyl]-3-methyl-4-(morpholin-3-on-4-yl)-benzamide,
(28) N-[(1R)-1-(5-chloro-1H-benzimidazol-2-yl)-2-methylsulphanyl-ethyl]-3-methyl-4-(morpholin-3-on-4-yl)-benzamide,
(29) N-[(1R)-1-(5-chloro-1H-benzimidazol-2-yl)-2-methoxy-ethyl]-3-methyl-4-(thiomorpholin-3-on-4-yl)-benzamide,
(30) 3-chloro-N-[(1R)-1-(5-chloro-1H-benzimidazol-2-yl)-2-methoxy-ethyl]-4-(morpholin-3-on-4-yl)-benzamide,
(31) 3-chloro-N-[(1R)-1-(5-chloro-1H-benzimidazol-2-yl)-2-methoxy-ethyl]-4-(1,1-dioxo-[1,2]thiazinan-2-yl)-benzamide,
(32) N-[(1R)-1-(5-chloro-1H-benzimidazol-2-yl)-2-methoxy-ethyl]-4-(1,1-dioxo-[1,2]thiazepan-2-yl)-3-methyl-benzamide,
(33) 3-bromo-N-[(1S)-1-(5-chloro-1H-benzimidazol-2-yl)-ethyl]-4-(piperidin-2-on-1-yl)-benzamide,
(34) 3-bromo-N-[(1R)-1-(5-chloro-1H-benzimidazol-2-yl)-2-methoxy-ethyl]-4-(piperidin-2-on-1-yl)-benzamide,
(35) N-[1-(5-chloro-1H-benzimidazol-2-yl)-1-(furan-2-yl)-methyl]-3-methyl-4-(piperidin-2-on-1-yl)-benzamide,

(36) N-[(1R)-1-(5-chloro-1H-benzimidazol-2-yl)-2-methoxy-ethyl]-3-methyl-4-(5-oxo-[1,4]oxazepan-4-yl)-benzamide,
(37) 3-chloro-N-[(1R)-1-(5-chloro-1H-benzimidazol-2-yl)-2-methoxy-ethyl]-4-(4-methyl-2-oxo-oxazolidin-3-yl)-benzamide,
(38) N-[1-(5-chloro-1H-benzimidazol-2-yl)-1-phenyl-methyl]-3-methyl-4-(morpholin-3-on-4-yl)-benzamide,
(39) 3-bromo-N-[(1R)-1-(5-chloro-1H-benzimidazol-2-yl)-2-methoxy-ethyl]-4-(morpholin-3-on-4-yl)-benzamide,
(40) N-[(1R)-1-(5-chloro-1H-benzimidazol-2-yl)-1-(thiophen-2-yl)-methyl]-3-methyl-4-(morpholin-3-on-4-yl)-benzamide,
(41) N-[(1R)-1-(5-bromo-1H-benzimidazol-2-yl)-2-hydroxy-ethyl]-4-(1,1-dioxo-[1,2]thiazinan-2-yl)-3-methyl-benzamide,
(42) N-[(1R)-1-(5-bromo-1H-benzimidazol-2-yl)-2-hydroxy-ethyl]-3-methyl-4-([1,3]oxazepan-2-on-3-yl)-benzamide,
(43) N-[(1R)-1-(5-chloro-1H-benzimidazol-2-yl)-2-methoxy-ethyl]-3-methyl-4-(4-(4S)-methyl-2-oxo-oxazolidin-3-yl)-benzamide,
(44) 3-chloro-N-[(1R)-1-(5-chloro-1H-benzimidazol-2-yl)-2-methoxy-ethyl]-4-(4,4-dimethyl-2-oxo-oxazolidin-3-yl)-benzamide,
(45) N-[(1R)-1-(5-chloro-1H-benzimidazol-2-yl)-2-methoxy-ethyl]-3-methyl-4-(4-(4R)-methyl-2-oxo-oxazolidin-3-yl)-benzamide,
(46) 3-chloro-N-[(1R)-1-(5-chloro-1H-benzimidazol-2-yl)-2-methoxy-ethyl]-4-(4-(4R)-ethyl-2-oxo-oxazolidin-3-yl)-benzamide,
(47) N-[(1R)-1-(5-chloro-1H-benzimidazol-2-yl)-2-methoxy-ethyl]-3-fluoro-4-(morpholin-3-on-4-yl)-benzamide,
(48) N-[1-(5-chloro-1H-benzimidazol-2-yl)-1-(1H-pyrazol-3-yl)-methyl]-3-methyl-4-(morpholin-3-on-4-yl)-benzamide,
(49) N-[1-(5-chloro-1H-benzimidazol-2-yl)-1-(1H-1-methyl-pyrazol-3-yl)-methyl]-3-methyl-4-(morpholin-3-on-4-yl)-benzamide,
(50) 3-chloro-N-[(1R)-1-(5-chloro-1H-benzimidazol-2-yl)-2-methoxy-ethyl]-4-(5-methyl-morpholin-3-on-4-yl)-benzamide,
(51) 3-chloro-N-[(1R)-1-(5-chloro-1H-benzimidazol-2-yl)-2-methoxy-ethyl]-4-(tetrahydro-pyrimidin-2-on-1-yl)-benzamide,
(52) N-[1-(5-chloro-1H-benzimidazol-2-yl)-thiophen-3-yl-methyl]-3-methyl-4-(morpholin-3-on-4-yl)-benzamide,
(53) N-[(1S)-1-(5-chloro-1H-benzimidazol-2-yl)-ethyl]-3-methyl-4-([1,3]oxazepan-2-on-3-yl)-benzamide
(54) N-[(1S)-1-(5-chloro-1H-benzimidazol-2-yl)-3-methyl-sulphanyl-propyl)-4-(piperazin-1-yl)-3-trifluoromethyl-benzamide,
(55) N-[(1S)-1-(5-chloro-1H-benzimidazol-2-yl)-3-methyl-sulphanyl-propyl)-4-(morpholin-3-on-4-yl)-3-nitro-benzamide,
(56) N-[(1R)-1-(5-chloro-1H-benzimidazol-2-yl)-2-methoxy-ethyl]-3-methyl-4-(piperazin-1-yl)-benzamide,
(57) N-[(1S)-1-(7-chloro-imidazo[1,2a]pyridin-2-yl)-3-methyl-butyl]-3-methyl-4-(morpholin-3-on-4-yl)-benzamide,
the tautomers, the enantiomers, the diastereomers, the mixtures thereof and the salts thereof are particularly preferred.

Within the scope of the present application, where applicable, the "isomer", "stereoisomer", "diastereomer", "enantiomer", "chiral", "racemate" or "racemic mixture" are defined as follows. Compounds of the same empirical formula which differ in the nature or arrangement of the bonding of their atoms or their connectivity or the spatial arrangement of the atoms in the molecule are known as "isomers". Isomers which differ in the spatial arrangement of the atoms in the molecule and are not congruent, while having the same type of connectivity of their atoms, are known as "stereoisomers". Stereoisomers which do not behave as image and mirror image to one another are known as "diastereomers", and stereoisomers which behave as an image and mirror image to one another are known as "enantiomers". Where an asymmetric centre or atom is present (also known as a stereocentre or chiral centre), for example in the case of a carbon atom substituted by four different substituents, the molecule has the attribute "chiral", and a pair of enantiomers is possible. An enantiomer may be characterised by the absolute configuration of its stereocentre. The absolute configuration is described by means of the descriptors (R) and (S), which are determined by the application of the sequence rules according to Cahn, Ingold and Prelog, or by describing the rotation of the plane of polarised light as it interacts with the molecule, which is referred to as dextrorotatory or laevorotatory (i.e. accordingly with (+) or (−) as the descriptor). A chiral compound may occur both as an individual enantiomer or as a mixture of the corresponding enantiomers. A mixture which contains equal amounts of both enantiomers of a compound is known as a "racemate" or "racemic mixture".

According to the invention the compounds of general formula I are obtained by methods known per se, for example by the following methods:

(a) In order to prepare compounds of general formula

wherein $R^3$ to $R^5$ are as hereinbefore defined and $Z^1$ denotes the hydrogen atom or a protective group and B' denotes a group of formula

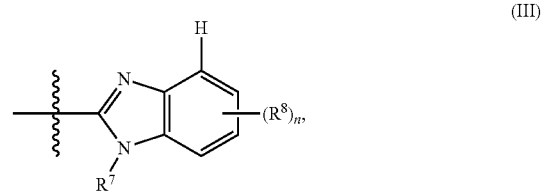

wherein $R^7$ and $R^8$ are as hereinbefore defined:
cyclisation of a compound of general formula

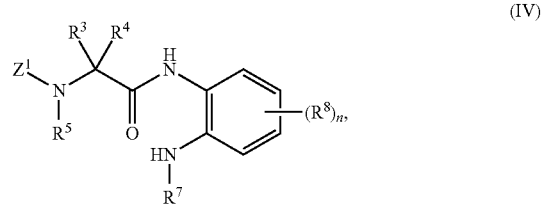

optionally formed in the reaction mixture wherein

R³ to R⁵, R⁷ and R⁸ are as hereinbefore defined and Z¹ denotes the hydrogen atom or a protective group, after which any protective group used is cleaved.

The cyclisation is conveniently carried out in a solvent or mixture of solvents such as ethanol, isopropanol, glacial acetic acid, benzene, chlorobenzene, toluene, xylene, glycol, glycolmonomethylether, diethyleneglycoldimethylether, sulpholane, dimethylformamide or tetralin, dimethylsulphoxide, methylene chloride, chloroform, tetrachloromethane, for example at temperatures between 0 and 250° C., but preferably between 20 and 100° C., optionally in the presence of a condensation agent such as phosphorus oxychloride, thionyl chloride, sulphurylchloride, sulphuric acid, p-toluenesulphonic acid, methanesulphonic acid, hydrochloric acid, phosphoric acid, polyphosphoric acid, acetic acid, acetic anhydride, N,N'-dicyclohexylcarbodiimide or optionally also in the presence of a base such as potassium ethoxide or potassium-tert.-butoxide. The cyclisation may however also be carried out without a solvent and/or condensation agent.

Compounds of general formula (IV) may be obtained by acylation of compounds of general formula

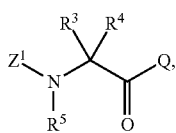

(XXIV)

wherein n, R⁷ and R⁸ are as hereinbefore defined, with compounds of general formula

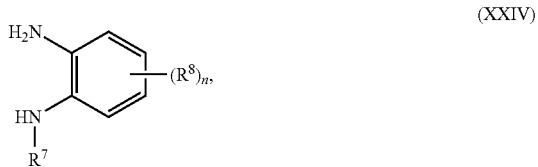

(XXV)

wherein R³, R⁴ and R⁵ are as hereinbefore defined, Q denotes a halogen atom or a hydroxy, $C_{1-4}$-alkoxy or $C_{1-4}$-acyloxy group and Z¹ denotes a protective group, according to processes described in (e).

(b) In order to prepare a compound of general formula

(II)

wherein R³ to R⁵ are as hereinbefore defined, Z¹ denotes the hydrogen atom or a protective group, for example a $C_{1-5}$-alkyloxycarbonyl or benzyloxycarbonyl group, and B' denotes a group of formula

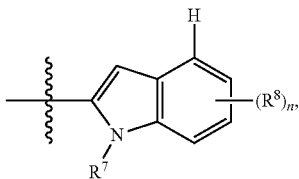

(V)

wherein R⁷ and R⁸ are as hereinbefore defined:

i) transition metal-catalysed coupling and cyclisation of a compound of general formula

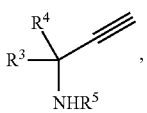

(VI)

wherein R³ denotes a phenyl or heteroaryl group and R⁴ denotes a hydrogen atom and R⁵ is as hereinbefore defined, with a compound of general formula

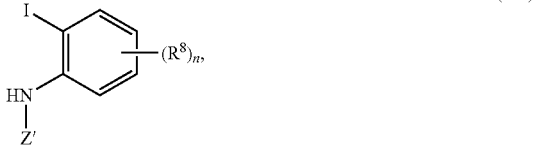

(VII)

wherein R⁸ is as hereinbefore defined and Z¹ denotes a protective group, for example an acetyl or methylsulphonyl group, after which the protective group is cleaved.

The reaction sequence is conveniently carried out in a solvent or mixture of solvents such as ethanol, isopropanol, glacial acetic acid, benzene, chlorobenzene, toluene, xylene, glycol, glycolmonomethylether, diethyleneglycoldimethylether, sulpholane, dimethylformamide, N-methylpyrrolidinone, tetralin, dimethylsulphoxide, methylene chloride, chloroform or tetrachloromethane, for example at temperatures between 0 and 250° C., but preferably between 20 and 120° C., conveniently in the presence of transition metal catalysts such as bis-(triphenylphosphine)-palladium (II)-chloride, bis-(tricyclohexylphosphine)-palladium (II)-chloride, bis-(triethylphosphine)-palladium (II)-chloride or bis-(tri-o-tolylphosphine)-palladium (II)-chloride and optionally in the presence of a transition metal catalyst such as copper (I)-iodide, copper (I)-bromide or copper (I)-acetate and conveniently in the presence of a base such as tetramethylguanidine, tetramethylethylenediamine or N,N'-dimethylethylenediamine as well as optionally using an inert gas atmosphere (for example nitrogen or argon).

ii) alkylation and subsequent reductive amination of a compound of general formula

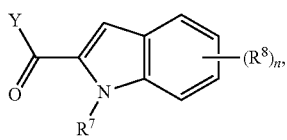

(VIII)

wherein $R^7$ and $R^8$ are as hereinbefore defined and Y denotes a halogen atom, a $C_{1-4}$-alkoxy, $C_{1-4}$-alkoxyamino or a N—$C_{1-4}$-alkoxy-N—$C_{1-4}$-alkylamino group, with a compound of general formula $$R^4\text{-M,} \quad (IX)$$

wherein $R^4$ is as hereinbefore defined and M denotes a metal such as for example lithium, sodium or potassium, or a metal such as for example magnesium, cadmium, copper or zinc, with a suitable counter-ion, such as for example chloride, bromide or iodide, or also a combination of two metals, such as for example magnesium and copper, lithium and copper or zinc and copper, with suitable counter-ions, such as for example cyanide, chloride, bromide or iodide, as well as a grouping containing combinations thereof, and subsequent reductive amination of the compounds thus obtained.

The alkylation is conveniently carried out in a solvent or mixture of solvents such as benzene, chlorobenzene, toluene, xylene, glycoldimethylether, diethyleneglycoldimethylether, sulpholane, dimethylformamide, N-methylpyrrolidinone, tetralin, dimethylsulphoxide, methylene chloride, chloroform, tetrachloromethane, diethyl ether, tert.-butyl-methylether or tetrahydrofuran, for example, at temperatures between −100 and +100° C., but preferably between −100 and 30° C., with alkylating reagents such as Grignard reagents, organolithium reagents, Gilman or Knochel cuprates which may be produced by methods known from the literature, optionally using an inert gas atmosphere (nitrogen or argon). The subsequent reductive amination of the ketones formed after alkylation is carried out for example by reaction with ammonia, hydroxylamine, alkoxyamines, primary amines, hydroxyl-alkylamines or alkoxy-alkylamines followed by or accompanied by reduction, for example with hydride donors such as sodium borohydride, lithium aluminium hydride, sodium cyanoborohydride, sodium triacetoxyborohydride or diisobutylaluminium hydride in a solvent or mixture of solvents such as ethanol, isopropanol, benzene, toluene, pyridine, ethyleneglycol-dimethylether, diethyleneglycoldimethylether, N-alkylmorpholine, diethyl ether, tert.-butylmethylether, tetrahydrofuran, hexane or cyclohexane or by hydrogenation optionally under pressure and conveniently in the presence of a catalyst such as Raney nickel, palladium, palladium charcoal, platinum or platinum oxide, in a solvent or mixture of solvents such as ethyl acetate, ethanol, isopropanol, benzene, toluene, pyridine, ethyleneglycol dimethylether, diethyleneglycol dimethylether, N—$C_{1-5}$-alkylmorpholine, diethyl ether, tert.-butyl-methylether, tetrahydrofuran, hexane or cyclohexane.

(c) In order to prepare a compound of general formula

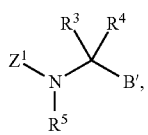

(II)

wherein $R^3$ to $R^5$ are as hereinbefore defined, $Z^1$ denotes the hydrogen atom or a protective group, for example a $C_{1-5}$-alkyloxycarbonyl or benzyloxycarbonyl group, and B' denotes a group of formula

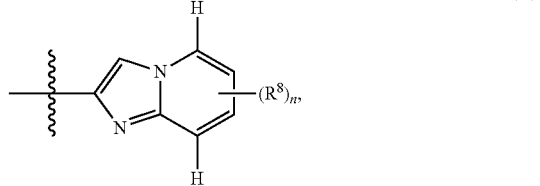

(X)

wherein $R^8$ is as hereinbefore defined:

coupling and subsequent cyclisation of a compound of general formula

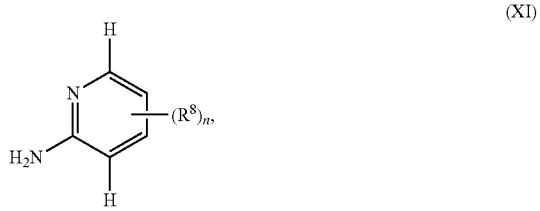

(XI)

wherein n and $R^8$ are as hereinbefore defined, with a compound of general formula

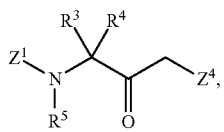

(XII)

wherein $R^3$ to $R^5$ are as hereinbefore defined, $Z^1$ denotes a protective group, for example a $C_{1-5}$-alkyloxycarbonyl or benzyloxycarbonyl group, and $Z^4$ denotes a nucleofugic leaving group, for example a chlorine, bromine or iodine atom, a tosylate, triflate or mesylate group, after which the protective group $Z^1$ is cleaved by methods known from the literature.

The reaction sequence is conveniently carried out in a solvent or mixture of solvents such as water, ethanol, isopropanol, benzene, chlorobenzene, toluene, xylene, glycol, glycoldimethylether, diethyleneglycoldimethylether, dimethylformamide, N-methylpyrrolidinone, tetralin, dimethylsulphoxide, sulpholane, methylene chloride, chloroform, tetrachloromethane or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., optionally conveniently in the presence of bases such as potassium carbonate, sodium carbonate, sodium hydrogen carbonate, potassium-tert.-butoxide, sodium ethoxide, potassium hexamethyldisilazane, sodium hydride or lithium diiso-propylamide.

(d) In order to prepare a compound of general formula

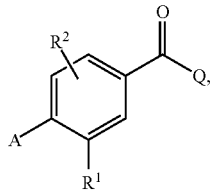
(XIII)

wherein A, $R^1$ and $R^2$ are as hereinbefore defined and Q denotes a halogen atom or a hydroxy, $C_{1-4}$-alkoxy or $C_{1-4}$-acyloxy group:
 i) nucleophilic substitution of a compound of general formula

A'-H, (XIV)

wherein A' denotes a 5- to 7-membered cycloalkyleneimino group as mentioned hereinbefore under the definition of A, at the aromatic group of general formula

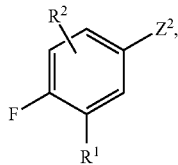
(XV)

wherein $R^1$ and $R^2$ are as hereinbefore defined and $Z^2$ denotes the nitrile group or a $C_{1-5}$-alkoxycarbonyl group, and subsequent saponification of the nitrile or $C_{1-5}$-alkoxycarbonyl group $Z^2$ and optionally further reaction of the resulting carboxyl group to form a reactive carboxylic acid derivative of general formula XIII.

The nucleophilic substitution is conveniently carried out in a solvent or mixture of solvents such as ethanol, isopropanol, benzene, chlorobenzene, toluene, xylene, glycol, glycoldimethylether, diethyleneglycoldimethylether, dimethylformamide, N-methylpyrrolidinone, tetralin, dimethylsulphoxide, sulpholane, methylene chloride, chloroform, tetrachloromethane or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between –30 and 250° C., but preferably between 0 and 150° C., optionally conveniently in the presence of bases such as potassium carbonate, sodium carbonate, potassium-tert.-butoxide, sodium ethoxide, potassium hexamethyldisilazane, sodium hydride or lithium diisopropylamide.
 ii) transition metal-catalysed coupling reaction of a compound of general formula

A'-H, (XIV)

wherein A' denotes a 5- to 7-membered cycloalkyleneimino group as mentioned hereinbefore under the definition of A, at the aromatic group of general formula

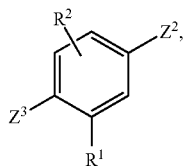
(XVI)

wherein $R^1$ and $R^2$ are as hereinbefore defined and $Z^2$ denotes the nitrile group or a $C_{1-5}$-alkoxycarbonyl group and $Z^3$ denotes a chlorine, bromine or iodine atom or a triflate group, and subsequent saponification of the nitrile or $C_{1-5}$-alkoxycarbonyl group $Z^2$ and optionally further reaction of the resulting carboxyl group to form a reactive carboxylic acid derivative of general formula XIII.

The reaction is expediently carried out in a solvent or mixture of solvents such as benzene, toluene, xylene, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethyl sulphoxide, methylene chloride, chloroform or tetrachloromethane, for example at temperatures between –30 and 250° C., but preferably between 0 and 150° C., conveniently in the presence of transition metal catalysts such as nickel on activated charcoal, palladium charcoal, tetrakis-(triphenylphosphine)-palladium (0), tris-(dibenzylideneacetone)-dipalladium (0), palladium (II)acetate, palladium (II)chloride, bis-(triphenylphosphine)-palladium (II)-chloride, bis-(tricyclohexylphosphine)-palladium (II)-chloride, bis-(triethylphosphine)-palladium (II)-chloride, bis-(tri-o-tolylphosphine)-palladium (II)-chloride, optionally in the presence of ligands such as triphenylphosphine, tri-o-tolylphosphine, tri-tert.-butylphosphine, 1,3-bis-(diphenylphosphino)-propane, 2,2'-bis-(diphenyl-phosphino)-1,1'-dinaphthyl, 1,1'-bis-(diphenylphosphino)-ferrocene, xantphos, and conveniently in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether as well as conveniently using an inert gas atmosphere (for example nitrogen or argon) and optionally under pressure.
 iii) Selective oxidation of a cycloalkyleneimino group in compounds of general formula

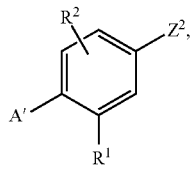
(XVII)

wherein A' denotes a 5- to 7-membered, optionally also substituted, 2-oxo-cycloalkyleneimine group as mentioned hereinbefore under the definition of A, $R^1$ and $R^2$ are as hereinbefore defined and $Z^2$ denotes the carboxyl group, and optionally further reacting to form a reactive carboxylic acid derivative of general formula XIII.

The reaction of a compound of general formula XIII obtained for example by the processes described hereinbefore, wherein A' denotes a cycloalkyleneimino group and Q denotes the hydroxy group, to form the corresponding lactam by oxidation of a methylene group adjacent to the nitrogen is carried out for example with oxidising agents such as potassium permanganate, potassium chromate, potassium dichromate, chromium (VI)oxide, mercury (II)chloride, selenium (IV)oxide, lead (IV)oxide, lead (II,IV)oxide, potassium peroxomonosulphate, hydrogen peroxide, sodium hypochlorite, optionally in the presence of a suitable catalyst such as nickel (II)chloride, cobalt (II)chloride, ruthenium (III)chloride, osmium (VIII)oxide, vanadium (IV)oxide and/or in the presence of a crown ether such as 18-crown-6, in a solvent or mixture of solvents such as water, formic acid, acetic acid, ethyl acetate, benzene, pyridine, dichloromethane, chloroform, tetrachloromethane, optionally under 2-phase conditions in the presence of a suitable phase transfer catalyst such as for example tetrabutylammonium chloride, tetrabutylammonium bromide, benzyl-triethyl-ammonium chloride or methyl-trioctyl-ammonium chloride, optionally in the presence of an acid such as acetic acid, hydrochloric acid, hydrobromic acid, sulphuric acid, phosphoric acid, sodium hydrogen sulphate, sodium dihydrogen phosphate and/or a base such as sodium hydroxide, potassium hydroxide, ammonia, pyridine, potassium phosphate, dipotassium hydrogen phosphate or sodium acetate at temperatures between −30 and 250° C., but preferably between 0 and 150° C. For example this reaction may be carried out as described by J. H. Markgraf, C. A. Stickney, *J. Heterocycl. Chem.* 2000, 37(1), 109.

iv) transition metal-catalysed coupling reaction of a compound of general formula

A'-H, (XIV)

wherein A' denotes a 5- to 7-membered, optionally substituted 2-oxo-cycloalkyleneimino group as mentioned hereinbefore under the definition of A, at the aromatic group of general formula

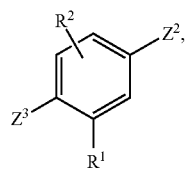

(XVI)

wherein $R^1$ and $R^2$ are as hereinbefore defined and $Z^2$ denotes the nitrile group or a $C_{1-5}$-alkoxycarbonyl group and $Z^3$ denotes a chlorine, bromine or iodine atom or a triflate group, and subsequent saponification of the nitrile or $C_{1-5}$-alkoxycarbonyl group $Z^2$ and optionally further reaction of the resulting carboxyl group to form a reactive carboxylic acid derivative of general formula XII.

The reaction is expediently carried out in a solvent or mixture of solvents such as benzene, toluene, xylene, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethylsulphoxide, methylene chloride, chloroform or tetrachloromethane, for example at temperatures between −30 and 250° C., but preferably between 0 and 200° C., conveniently in the presence of transition metal catalysts such as tetrakis-(triphenylphosphine)-palladium (0), tris-(dibenzylideneacetone)-dipalladium (0), palladium (II)acetate, palladium (II)chloride, bis-(triphenylphosphine)-palladium (II)-chloride, bis-(tricyclohexylphosphine)-palladium (II)-chloride, bis-(triethylphosphine)-palladium (II)-chloride, bis-(tri-o-tolylphosphine)-palladium (II)-chloride, optionally in the presence of ligands such as triphenylphosphine, tri-o-tolylphosphine, tri-tert.-butylphosphine, 1,3-bis-(diphenylphosphino)-propane, 2,2'-bis-(diphenylphosphino)-1,1'-dinaphthyl, 1,1'-bis-(diphenylphosphino)-ferrocene, xantphos, or for example in the presence of a transition metal catalyst such as copper (I)-iodide, copper (I)-bromide or copper (I)-acetate and conveniently in the presence of a base such as tetramethylguanidine, tetramethylethylenediamine or N,N'-dimethylethylenediamine and conveniently in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether and conveniently using an inert gas atmosphere (for example nitrogen or argon) and optionally under pressure.

v) Acylation/sulphonylation and alkylation of a compound of general formula

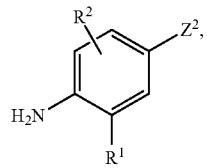

(XVIII)

wherein $R^1$ and $R^2$ are as hereinbefore defined and $Z^2$ denotes the nitrile group or a $C_{1-5}$-alkoxycarbonyl group, with a compound of general formula

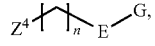

(XIX)

wherein E denotes a carbonyl, oxycarbonyl, sulphonyl or a sulphamoyl group optionally substituted at the nitrogen atom as mentioned hereinbefore, G denotes a chlorine, bromine or iodine atom or an anhydride, $C_{1-5}$-alkoxy or benzotriazoloxy group or E and G together denote an isocyano group and $Z^4$ denotes a nucleofugic leaving group, for example a chlorine, bromine or iodine atom, a tosylate, triflate or mesylate group, and n is a number between 3 and 5, while individual methylene groups according to the description mentioned hereinbefore may additionally be substituted or replaced by heteroatoms, and subsequent intramolecular cyclisation by alkylation of the anilide nitrogen while cleaving the nucleofugic leaving group $Z^4$, followed by saponification of the nitrile or $C_{1-5}$-alkoxycarbonyl group $Z^2$ and optionally further reaction of the resulting carboxyl group to form a reactive carboxylic acid derivative of general formula XIII.

The acylation/sulphonylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchanger.

The subsequent intramolecular alkylation is conveniently carried out in a solvent or mixture of solvents such as benzene, chlorobenzene, toluene, xylene, glycoldimethylether, diethyleneglycoldimethylether, dimethylformamide, dimethylsulphoxide, sulpholane, methylene chloride, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., conveniently in the presence of bases such as pyridine, triethylamine, potassium carbonate, sodium carbonate, potassium-tert.-butoxide, sodium methoxide, sodium ethoxide, sodium hydride, potassium hexamethyldisilazane or lithium diisopropylamide.

vi) carbamoylation/urea formation with a compound of general formula

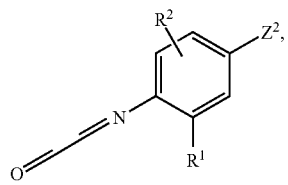

(XX)

wherein $R^1$ and $R^2$ are as hereinbefore defined and $Z^2$ denotes the nitrile group or a $C_{1-5}$-alkoxycarbonyl group, and which may be obtained by methods known from the literature from compounds of general formula XVIII, for example by reaction with phosgene in toluene, with a compound of general formula

(XXI)

wherein $Z^4$ denotes a nucleofugic leaving group, for example a chlorine, bromine or iodine atom, a tosylate, triflate or mesylate group, and E denotes a hydroxyl, amino or $C_{1-3}$-alkylamino function and n is a number between 2 and 4, while individual methylene groups may additionally be substituted according to the description mentioned hereinbefore, and subsequent intra-molecular cyclisation by alkylation of the anilide nitrogen while cleaving the nucleofugic leaving group $Z^4$, followed by saponification of the nitrile or $C_{1-5}$-alkoxycarbonyl group $Z^2$ and optionally further reaction of the resulting carboxyl group to form a reactive carboxylic acid derivative of general formula XIII.

The carbamoylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C. The subsequent intramolecular alkylation is carried out for example analogously to the method described under v).

vii) cyclisation metathesis of a compound of general formula

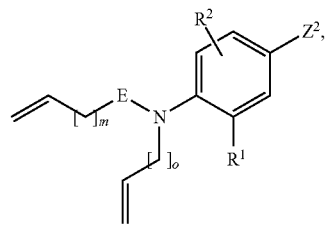

(XXII)

wherein $R^1$ and $R^2$ are defined as described hereinbefore, $Z^2$ denotes a nitrile, $C_{1-5}$-alkoxycarbonyl or carboxyl group, E denotes an aminocarbonyl, aminosulphonyl or amino group optionally substituted according to the description mentioned hereinbefore or a carbonyl or sulphonyl group or an oxygen or sulphur atom or a bond, while m and o independently of one another denote identical or different numbers between 1 and 3 which may be obtained by a sequence of alkylation and acylation/sulphonylation/carbamoylation/sulphamoylation with corresponding reagents by the methods already described herein or known from the literature, followed by saponification of the nitrile or $C_{1-5}$-alkoxycarbonyl group $Z^2$ and optionally further reaction of the resulting carboxyl group to obtain a reactive carboxylic acid derivative of general formula XIII.

The cyclisation by a reaction of metathesis is conveniently carried out in a solvent or mixture of solvents such as benzene, chlorobenzene, toluene, xylene, methanol, ethanol, propanol, diethyl ether, tert.-butyl-methyl-ether, tetrahydrofuran, dioxane, glycoldimethylether, diethyleneglycoldimethylether, dimethylformamide, N-methylpyrrolidinone, tetralin, dimethylsulphoxide, sulpholane, methylene chloride, chloroform, tetrachloromethane, pyridine, in the presence of a catalyst such as benzylidene-bis-(tricyclohexylphosphine)-dichloro-ruthenium (1st generation Grubbs catalyst) or benzylidene-[1,3-bis(2,4,6-trimethylphenyl)-2-imidazolidinylidene]-dichloro-(tricyclohexylphosphine)-dichloro-ruthenium (2nd generation Grubbs catalyst) for example at temperatures between −30 and 250° C., but preferably between 0 and 150° C., conveniently under an inert gas atmosphere, for example argon.

(e) In order to prepare a compound of general formula

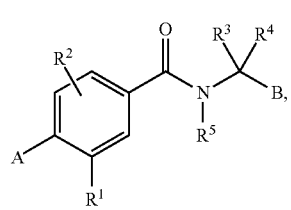

(XXIII)

wherein A, B and $R^1$ to $R^5$ are as hereinbefore defined:
acylation of a compound of general formula

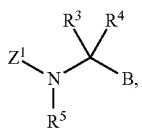
(II)

wherein B and $R^3$ to $R^5$ are as hereinbefore defined and $Z^1$ denotes the hydrogen atom,
with a carboxylic acid or a reactive carboxylic acid derivative of general formula

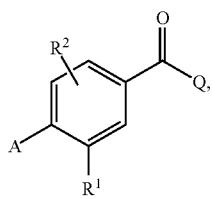
(XIII)

wherein A, $R^1$ and $R^2$ are as hereinbefore defined and Q denotes a hydroxy or $C_{1-4}$-alkoxy group, a halogen atom or an acyloxy group.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The acylation may, however, also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N-dicyclohexyl carbodiimide, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, apentafluorophenyl-N,N,N',N'-tetramethyluronium hexafluorophosphate/triethylamine, N,N'-thionyldiimidazole or triphenylphosphine/carbon tetrachloride, at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff, Pergamon 1995.

(f) In order to prepare a compound of general formula (II), (XXIV), (VII), (VIII), (XI) or (XXIII), wherein A, B and $R^1$ to $R^7$ are as hereinbefore defined and $R^8$ denotes a $C_{2-3}$-alkynyl group which is linked to the aromatic group via the carbon atom, and which simultaneously carries the triple bond, from a corresponding compound wherein $R^8$ denotes a bromine or iodine atom or the triflate, boric acid or boric acid ester group:

transition metal-catalysed coupling reaction of a compound of general formula

(XXVI)

wherein $Z^5$ denotes the hydrogen atom, the methyl group or a protective group such as for example a trimethylsilyl, tert.-butyl-dimethylsilyl, tert.-butyl-diphenylsilyl or triisopropyl group, which can then be cleaved,
with a compound of general formula (II), (XXIV), (VII), (VIII), (XI) or (XXIII), wherein A, B and $R^1$ to $R^7$ are as hereinbefore defined and $R^8$ denotes a bromine or iodine atom or the triflate, boric acid or boric acid ester group.

The reaction is preferably carried out in a solvent or mixture of solvents such as acetonitrile, diethyl ether, tetrahydrofuran, dioxane, water or dimethylformamide or a mixture of solvents in the presence of a palladium catalyst such as for example bis(triphenylphosphine)-palladium (II)chloride, palladium (II)-[1,1'-bis-(diphenylphosphino)ferrocene]-chloride or tetrakis-(triphenylphosphine)-palladium (0) in the presence of a base such as triethylamine, N-isopropyl-diethylamine, N,N-diisopropyl-ethylamine, potassium-tert.-butoxide, sodium carbonate or caesium carbonate, optionally in the presence of ligands such as triphenylphosphine, tri-o-tolylphosphine, tri-tert.-butylphosphine, 1,3-bis-(diphenylphosphino)-propane, 2,2'-bis-(diphenylphosphino)-1,1'-dinaphthyl, 1,1'-bis-(diphenylphosphino)-ferrocene, xantphos and optionally in the presence of a transition metal compound such as a copper halide such as for example copper (I)iodide and at temperatures between 20 and 120° C., preferably at temperatures between 20 and 90° C. under argon or nitrogen atmosphere (cf. also K. Sonogashira, Comprehensive Organic Synthesis, Vol. 3, page 52ff., Pergamon Press, Oxford 1991).

Any silyl protective group present such as for example trimethylsilyl is preferably cleaved in a solvent or mixture of solvents such as water, methanol, ethanol, isopropanol, acetone, dioxane, tetrahydrofuran or dimethylformamide in the presence of a base such as lithium hydroxide, sodium hydroxide, potassium carbonate or sodium methoxide. For cleaving in organic solvents such as for example diethyl ether, tetrahydrofuran, dimethylformamide or dichloromethane it is also possible to use fluoride reagents, such as for example tetrabutylammonium fluoride, lithium fluoride or potassium fluoride, optionally with the addition of a complexing agent such as 18-crown-6-ether.

In the reactions described above any reactive groups present such as hydroxy, carboxy, amino, alkylamino or imino groups may be protected during the reaction by conventional protecting groups which are cleaved again after the reaction. For example, a suitable protecting group for a hydroxy group may be the methoxy, benzyloxy, trimethylsilyl, acetyl, benzoyl, tert.butyl, trityl, benzyl or tetrahydropyranyl group,
suitable protecting groups for a carboxyl group might be the trimethylsilyl, methyl, ethyl, tert.butyl, benzyl or tetrahydropyranyl group,
suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group.

Other protective groups and their cleaving are described in T. W. Greene, P. G. M. Wuts, "Protecting Groups in Synthesis", Wiley, 1991 and 1999.

Any protecting group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

A methoxybenzyl group may also be cleaved in the presence of an oxidising agent such as cerium (IV)ammonium nitrate in a solvent such as methylene chloride, acetonitrile or acetonitrile/water at temperatures of between 0 and 50° C., but preferably at ambient temperature.

A methoxy group is expediently cleaved in the presence of boron tribromide in a solvent such as methylene chloride at temperatures between −35 and −25° C.

A 2,4-dimethoxybenzyl group is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium (I)chloride in a solvent such as aqueous ethanol and optionally in the presence of a base such as 1,4-diazabicyclo[2.2.2]octane at temperatures between 20 and 70° C.

Compounds of general formulae (II), wherein the group B' is represented by a group of general formula (III), and (IV) may be prepared for example analogously to K. Maekawa, J. Ohtani, *Agr. Biol. Chem.* 1976, 40, 791-799.

Moreover the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyl-tartaric acid, malic acid, mandelic acid, camphorsulphonic acid, glutamic acid, aspartic acid or quinic acid. An optically active alcohol may be for example (+) or (−)-menthol and an optically active acyl group in amides may be a (+)- or (−)-menthyloxycarbonyl, for example.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula I as well as the tautomers, the enantiomers, the diastereomers and the physiologically acceptable salts thereof have valuable pharmacological properties, particularly an antithrombotic activity, which is preferably based on an effect on thrombin or factor Xa, for example on a thrombin-inhibiting or factor Xa-inhibiting activity, on a prolonging effect on the aPTT time and/or on an inhibiting effect on related serine proteases such as e.g. urokinase, factor VIIa, factor IXa, factor XIa and factor XIIa.

The compounds listed in the experimental section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free Factor Xa (Calbiochem), spec. activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 µMol/l Procedure:

10 µl of a 23.5-times concentrated starting solution of the test substance or solvent (control), 175 ml of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbation of COPD, for treating ulcerative colitis, for treating and preventing coronary thrombosis, for preventing stroke and the occlusion of shunts. In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic incidents in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention without restricting its scope:

EXPERIMENTAL SECTION

As a rule, melting points, IR, UV, $^1$H-NMR and/or mass spectra have been obtained for the compounds prepared. Unless otherwise stated, $R_f$ values were obtained using ready-made silica gel 60 $F_{254}$ TLC plates (E. Merck, Darmstadt, Item no. 1.05714) without chamber saturation. The $R_f$ values obtained under the name Alox were determined using ready-made aluminium oxide 60 $F_{254}$ TLC plates (E. Merck, Darmstadt, Item no. 1.05713) without chamber saturation. The $R_f$ values obtained under the name Reversed-phase-8 were determined using ready-made RP-$8_{F254s}$ TLC plates (E. Merck, Darmstadt, Item no. 1.15684) without chamber saturation. The ratios given for the eluants refer to units by volume of the solvent in question. Chromatographic purification was done using silica gel supplied by Messrs Millipore (MATREX™, 35-70 µm). If the configuration is not specified in detail, it is unclear whether the compound in question is a pure stereoisomer or a mixture of enantiomer and diastereomer.

The following abbreviations are used in the descriptions of the tests:
Boc tert.-butoxycarbonyl
DIPEA N-ethyl-diisopropylamine
DMSO dimethylsulphoxide
DMF N,N-dimethylformamide
sat. saturated
h hour(s)
i. vac. in vacuo
conc. concentrated
NMM N-methyl-morpholine
NMP N-methyl-pyrrolidin-2-one
o ortho
PfTU O-pentafluorophenyl-N,N,N',N'-etramethyluronium hexafluorophosphate
PPA propanephosphonic cycloanhydride
quant. quantitative
$R_f$ retention factor
$R_t$ retention time
rac. racemic
TBTU O-(benzotriazol-1-yl)-N,N,N,N-tetramethyluronium tetrafluoroborate
TEA triethylamine
TFA trifluoroacetic acid
THF tetrahydrofuran
tert. tertiary
Σ yield over all the steps carried out analogously as described The HPLC/MS data for Examples 35 to 38 were obtained under the following conditions:
(a) Waters ZMD, Alliance 2690 HPLC, Waters 2700 Autosampler, Waters 996 diode array detector
The following was used as the mobile phase:
A: water with 0.1% trifluoroacetic acid
B: acetonitrile with 0.1% trifluoroacetic acid

| time in min | % A | % B | flow rate in ml/min |
|---|---|---|---|
| 0.0 | 95 | 5 | 1.00 |
| 0.1 | 95 | 5 | 1.00 |
| 5.1 | 2 | 98 | 1.00 |
| 6.5 | 2 | 98 | 1.00 |
| 7.0 | 95 | 5 | 1.00 |

The stationary phase used was a Waters column X-Terra™ MS $C_{18}$ 3.5 μm, 4.6 mm×50 mm (column temperature: constant at 25° C.)
The diode array detection took place in a wavelength range from 210-500 nm Range of mass-spectrometry detection: m/z 120 to m/z 950
(b) The HPLC/MS data for the other Examples, if provided, were obtained under the following conditions:
HP 1100 with quarternary pump, Gilson G215 Autosampler, HP diode array detector.
The mobile phase used was:
A: water with 0.1% TFA
B: acetonitrile with 0.08% TFA

| time in min | % A | % B | flow rate in ml/min |
|---|---|---|---|
| 0.0 | 95 | 5 | 0.4 |
| 0.15 | 95 | 5 | 0.4 |
| 4.65 | 2 | 98 | 0.4 |
| 6.0 | 2 | 98 | 0.4 |
| 6.5 | 95 | 5 | 0.4 |

The stationary phase used was a Waters column X-Terra™ MS $C_{18}$ 2.5 μm, 2.1 mm×50 mm (column temperature: constant at 25° C.)
The diode array detection took place in a wavelength range from 210-550 nm Range of mass-spectrometry detection: m/z 120 to m/z 1000.

Example 1

3-chloro-N-[(1S)-1-(5-chloro-1H-benzimidazol-2-yl)-ethyl]-4-([1,4]diazepan-1-yl)-benzamide

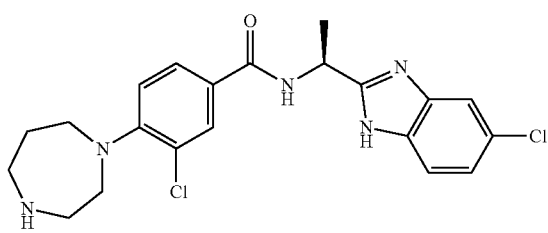 [SMILES: C[C@H](NC(=O)c1ccc(N2CCCNCC2)c(Cl)c1)c1nc2cc(Cl)ccc2[nH]1]

(a) 4-(4-N-acetyl-[1,4]diazepan-1-yl)-3-chloro-benzonitrile 4.67 g (30 mmol) 3-chloro-4-fluoro-benzonitrile and 4.27 g (30 mmol) N-1-acetyl-[1,4]diazepan are stirred in 5.0 ml DIPEA for 6 hours at 90° C. Then the mixture is evaporated down i. vac. and the residue is dissolved in dichloromethane. The organic phase is washed twice with water, dried over sodium sulphate and evaporated down i. vac. The residue is further reacted without any more purification.
Yield: 7.50 g (90%)
$R_f$ value: 0.20 (silica gel; dichloromethane/ethanol=50:1)

(b) 3-chloro-4-([1,4]diazepan-1-yl)-benzoic acid

The residue obtained in Example 1a (7.50 g, 27.0 mmol) is refluxed for 8 h in 50 ml 25% potassium hydroxide solution. Then the mixture is adjusted to pH 5 with conc. hydrochloric acid. The solid precipitated is filtered off, dried and further reacted without any more purification.
Yield: 5.60 g (81%)
$R_f$ value: 0.0 (silica gel; dichloromethane/ethanol=9:1)

(c) methyl 3-chloro-4-([1,4]diazepan-1-yl)-benzoate

The residue obtained in Example 1b (3.00 g, 11.8 mmol) is suspended in 100 ml of methanol and hydrogen chloride is piped in over 1 hour with stirring and heating to reflux temperature. Then the mixture is evaporated down i. vac., the residue is combined with 5% sodium hydrogen carbonate solution and extracted 3 times with dichloromethane. The combined organic phases are dried over sodium sulphate. The residue remaining after evaporation i. vac. is further reacted without any more purification.
Yield: 2.25 g (71%)
$R_f$ value: 0.10 (silica gel; dichloromethane/ethanol=4:1+2% ammonia)
$C_{13}H_{17}ClN_2O_2$ (268.75)
Mass spectrum: $(M+H)^+$=269/271 (chlorine isotope)

(d) methyl 4-(4-N-Boc-[1,4]diazepan-1-yl)-3-chloro-benzoate

The residue obtained in Example 1c (1.00 g, 3.72 mmol) is combined with 0.53 g (3.80 mmol) potassium carbonate in 10 ml dichloromethane and then 0.83 g (3.80 mmol) di-tert. butyl pyrocarbonate are added dropwise. Then the mixture is stirred for 16 hours at ambient temperature. Then it is diluted with dichloromethane, washed twice with water, dried over sodium sulphate and evaporated down i. vac. Purification by chromatography on silica gel is then carried out (eluant: methylene chloride/ethanol 99:1).
Yield: 1.34 g (98%)
$R_f$ value: 0.50 (silica gel; dichloromethane/ethanol=50:1)
$C_{18}H_{25}ClN_2O_4$ (368.86)
Mass spectrum: $(M+H)^+$=369/371 (chlorine isotope)

(e) 4-(4-N-Boc-[1,4]diazepan-1-yl)-3-chloro-benzoic acid 0.60 g (1.63 mmol) methyl 4-(4-N-Boc-[1,4]diazepan-1-yl)-3-chloro-benzoate are dissolved in 10 ml of methanol, combined with 4 ml 2-molar potassium hydroxide solution and stirred for 3 hours at 40° C. Then the mixture is evaporated down i. vac., the residue is diluted with distilled water, acidified with saturated potassium hydrogen sulphate solution and extracted 3 times with ethyl acetate. The combined organic phases are dried over sodium sulphate and concentrated by evaporation. The residue is further reacted without any more purification.
Yield: 0.50 g (87%)
$R_f$ value: 0.05 (silica gel; dichloromethane/ethanol=50:1)
$C_{17}H_{23}ClN_2O_4$ (354.84)

(f) 4-(4-N-Boc-[1,4]diazepan-1-yl)-3-chloro-N-[(1S)-1-(5-chloro-1H-benzimidazol-2-yl)-ethyl]-benzamide 532 mg (1.50 mmol) 4-(4-N-Boc-[1,4]diazepan-1-yl)-3-chloro-benzoic acid are suspended in 15 ml THF and after the addition of 546 mg (1.70 mmol) TBTU and 646 mg (5.0 mmol) DIPEA stirred for 30 minutes at ambient temperature. Then 403 mg (1.50 mmol) (1S)-1-(5-chloro-1H-benzimidazol-2-yl)-ethylamine-dihydrochloride are added and the mixture is stirred for a further 16 hours at ambient temperature. It is then evaporated down i. vac., the residue is dissolved in ethyl acetate, the organic phase is washed with 5% sodium hydrogen carbonate solution and water and dried over sodium sulphate. After evaporation i. vac. the residue remaining is purified by chromatography on silica gel (eluting gradient: petroleum ether/ethyl acetate: 90:10->60:40).

Yield: 630 mg (79%)
$R_f$-value: 0.50 (silica gel; dichloromethane/ethanol=19:1)
$C_{26}H_{31}Cl_2N_5O_3$ (532.48)
Mass spectrum: $(M+H)^+$=532/534/536 (chlorine isotope)

(g) 3-chloro-N-[(1S)-1-(5-chloro-1H-benzimidazol-2-yl)-ethyl]-4-([1,4]diazepan-1-yl)-benzamide A solution of 610 mg (1.15 mmol) 4-(4-N-Boc-[1,4]diazepan-1-yl)-3-chloro-N-[(1S)-1-(5-chloro-1H-benzimidazol-2-yl)-ethyl]-benzamide in 30 ml dichloromethane is combined with 3 ml TFA and stirred for 3 hours at ambient temperature. Then it is evaporated down i. vac., the residue is taken up in ethyl acetate, washed with 5% sodium hydrogen carbonate solution and water and dried over sodium sulphate. After evaporation i. vac. the residue is purified by chromatography on silica gel (eluting gradient: petroleum ether/ethyl acetate 80:20->50:50).

Yield: 380 mg (77%)
$R_f$-value: 0.10 (silica gel; dichloromethane/ethanol=9:1)
$C_{21}H_{23}Cl_2N_5O$ (432.36)
Mass spectrum: $(M+H)^+$=432/434/436 (chlorine isotope)
The following compound was prepared analogously:

Example 2

4-(4-N-Boc-piperazin-1-yl)-N-[(1S)-1-(5-chloro-1H-benzimidazol-2-yl)-ethyl]-3-trifluoromethyl-benzamide

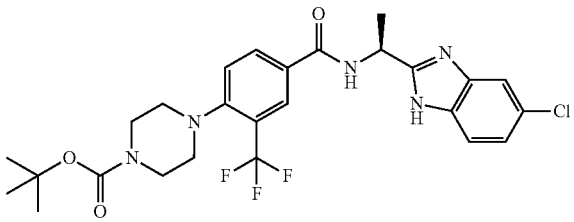

(a) 4-(piperazin-1-yl)-3-trifluoromethyl-benzoic acid 37.9 g (195 mmol) piperazine hexahydrate are refluxed for 2 hours with 12.4 g (66 mmol) 4-fluoro-3-trifluoromethyl-benzonitrile suspended in 40 ml of ethanol. Then 13.7 ml (261 mmol) 50% sodium hydroxide solution and 13.7 ml of water are added and the mixture is refluxed for a further 3.5 hours and kept at ambient temperature for a further 15 hours. Then 43.5 ml of conc. hydrochloric acid are added and the mixture is cooled to 10° C. for 30 minutes with stirring. The precipitate obtained is suction filtered, washed with a little water and dried at 40° C. in the circulating air dryer for 24 hours.

Yield: 20.8 g (quantitative)

(b) methyl 4-(piperazin-1-yl)-3-trifluoromethyl-benzoate 5.00 g (18.2 mmol) 4-(piperazin-1-yl)-3-trifluoromethyl-benzoic acid are stirred 16 hours in 50 ml of methanolic hydrochloric acid. After evaporation of the reaction mixture i.

| structural formula No. Name | | yield | mass peak(s) | $R_f$-value/$R_t$ value |
|---|---|---|---|---|
| 115 | 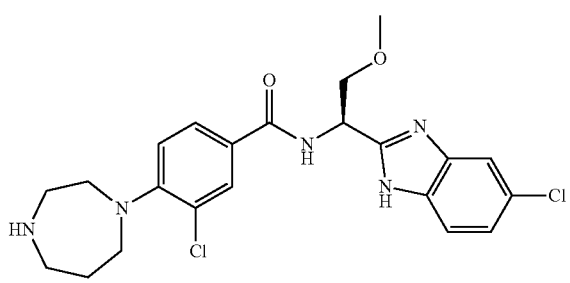 [SMILES: COC[C@H](NC(=O)c1ccc(N2CCCNCC2)c(Cl)c1)c1nc2cc(Cl)ccc2[nH]1] | Σ: 13% | $(M + H)^+$ = 462/464/466 (chlorine isotope) | 0.13 (silica gel, dichloromethane/ methanol = 9:1) |
| | N-[(1R)-1-(5-chloro-1H-benzimidazol-2-yl)-2-methoxy-ethyl]-3-chloro-4-([1,4]-diazepan-1-yl)-benzamide | | | | vac. the residue is stirred with isopropanol. The solid is filtered off, washed with diethyl ether and dried at 60° C. in the circulating air dryer.
Yield: 5.00 g (76%)
$C_{13}H_{15}F_3N_2O_2 \cdot 2HCl$ (288.27/361.19)
Mass spectrum: $(M+H)^+=289$
$R_f$ value: 0.58 (silica gel; cyclohexane/dichloromethane/methanol=70:15:15+2% conc. ammonia solution)

(c) methyl 4-(4-N-Boc-piperazin-1-yl)-3-trifluoromethyl-benzoate 5.77 g (11.78 mmol) methyl 4-(piperazin-1-yl)-3-trifluoromethyl-benzoate are placed in 100 ml THF and combined with 4.47 g (20.5 mmol) di-tert. butyl pyrocarbonate. After 40 hours stirring at ambient temperature under a nitrogen atmosphere the reaction mixture is evaporated down i. vac., the residue is combined with water and sat. sodium chloride solution and extracted with ethyl acetate. The combined organic phases are washed with water, semisaturated and sat. sodium chloride solution, dried over magnesium sulphate and evaporated down i. vac. The residue is purified by chromatography on silica gel (eluting gradient: petroleum ether/ethyl acetate 9:1->8:1).
Yield: 2.60 g (34%)
$R_f$ value: 0.52 (silica gel; petroleum ether/ethyl acetate 7:3+1% conc. ammonia solution)
$C_{18}H_{23}F_3N_2O_4$ (388.39)
Mass spectrum: $(M+H)^+=389$ (d) 4-(4-N-Boc-piperazin-1-yl)-3-trifluoromethyl-benzoic acid 2.60 g (6.69 mmol) methyl 4-(4-N-tert.-butoxylcarbonyl-piperazin-1-yl)-3-trifluoromethyl-benzoate are dissolved in 10 ml of methanol and combined with 12.3 ml (12.3 mmol) 1-molar sodium hydroxide solution. After 15 minutes a further 10 ml of methanol are added and the reaction mixture is stirred for 42 hours at ambient temperature. Then the mixture is evaporated down i. vac., the residue is combined with ice and acidified with acetic acid. The precipitate obtained is suction filtered, washed with water and dried in the circulating air dryer at 50° C. and in the drying pistol at 40° C. over KOH and $SiO_2$.
Yield: 2.40 g (96%)
$R_f$ value: 0.41 (silica gel; petroleum ether/ethyl acetate=1:1+1% acetic acid)
$C_{17}H_{21}F_3N_2O_4$ (374.36)
Mass spectrum: $(M-H)^-=373$ (e) 4-(4-N-Boc-piperazin-1-yl)-N-[(1S)-1-(5-chloro-1H-benzimidazol-2-yl)-ethyl]-3-trifluoromethyl-benzamide Prepared analogously to Example 1f from 4-(4-N-Boc-piperazin-1-yl)-3-trifluoromethyl-benzoic acid, TBTU, NMM and (1S)-1-(5-chloro-1H-benzimidazol-2-yl)ethylamine in NMP and subsequent purification by chromatography on silica gel (eluant: petroleum ether/ethyl acetate=50:50).
Yield: 57%
$R_f$ value: 0.20 (silica gel; petroleum ether/ethyl acetate=1:1)
$C_{26}H_{29}ClF_3N_5O_3$ (552.00)
Mass spectrum: $(M+H)^+=552/554$ (chlorine isotope)

Example 3

N-[(1S)-1-(5-chloro-1H-benzimidazol-2-yl)-ethyl]-4-(piperazin-1-yl)-3-trifluoromethyl-benzamide

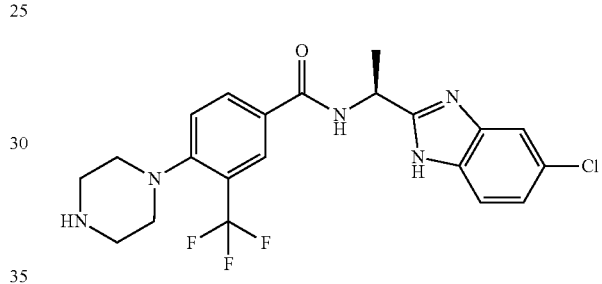

Prepared analogously to Example 1g from 4-(4-N-Boc-piperazin-1-yl)-N-[(1S)-1-(5-chloro-1H-benzimidazol-2-yl)-ethyl]-3-trifluoromethyl-benzamide and TFA in dichloromethane.
Yield: 73%
$R_f$ value: 0.28 (silica gel; dichloromethane/methanol=90:10+ammonia solution)
$C_{21}H_{21}ClF_3N_5O \cdot 2\ CF_3COOH$ (679.93/451.88)
Mass spectrum: $(M+H)^+=452/454$ (chlorine isotope)
The following were prepared analogously to the sequence described in Examples 2 and 3:

| No. | structural formula Name | yield | mass peak(s) | $R_f$ value |
|---|---|---|---|---|
| 4 | ![structure] N-[(1R)-1-(5-chloro-1H-benzimidazol-2-yl)-2-methoxy-ethyl)-4-(piperazin-1-yl)-3-trifluoromethyl-benzamide | Σ: 14% | $(M + H)^+ =$ 482/484 (chlorine isotope) | 0.15 (silica gel, $CH_3COOC_2H_5$/$C_2H_5OH$ 9:1 + $NH_3$) |

| structural formula No. Name | yield | mass peak(s) | $R_f$ value |
|---|---|---|---|
| 40 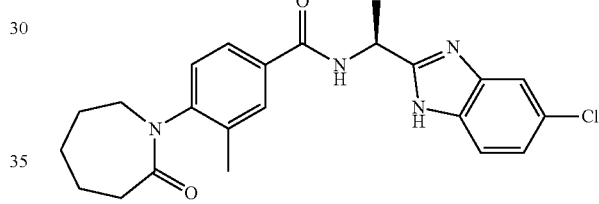<br>N-[(1S)-1-(5-chloro-1H-benzmidazol-2-yl)-3-methylsulphanyl-propyl]-4-(piperazin-1-yl)-3-trifluoromethyl-benzamide | Σ: 13% | $(M + H)^+$ = 512/514 (chlorine isotope) | 0.20 (silica gel, $CH_2Cl_2$/ $C_2H_5OH$ 9:1) |

Example 5

4-(4-N-acetyl-piperazin-1-yl)-N-[(1S)-1-(5-chloro-1H-benzimidazol-2-yl)-ethyl]-3-trifluoromethyl-benzamide

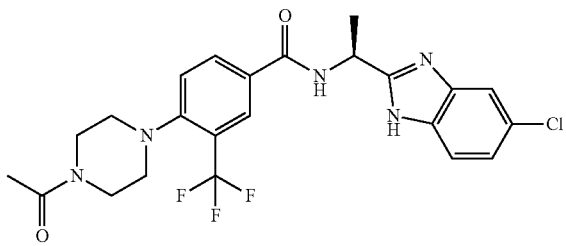 [SMILES: CC(=O)N1CCN(c2ccc(C(=O)N[C@@H](C)c3nc4cc(Cl)ccc4[nH]3)cc2C(F)(F)F)CC1]

220 mg (0.32 mmol) N-[(1S)-1-(5-chloro-1H-benzimidazol-2-yl)-ethyl]-4-(piperazin-1-yl)-3-trifluoromethyl-benzamide-ditrifluoroacetate in 5 ml THF are combined with 0.23 ml (1.65 mmol) TEA, 50 µl (0.70 mmol) acetylchloride are added dropwise with stirring and cooling in the ice bath and stirred for 2 hours at ambient temperature. The reaction mixture is poured into ice water and then extracted with ethyl acetate. The organic phase is washed with water and sat. sodium chloride solution, dried over sodium sulphate and evaporated down i. vac. The residue is triturated with a solvent mixture of ethyl acetate and diethyl ether, filtered off, washed with diethyl ether and dried in a drying pistol at 50° C.

Yield: 0.13 g (81%)

$R_f$ value: 0.55 (silica gel; dichloromethane/ethanol=9:1+ ammonia solution)

$C_{23}H_{23}ClF_3N_5O_2$ (493.92)

Mass spectrum: $(M+H)^+$=494/496 (chlorine isotope)

Example 6

4-(azepan-2-on-1-yl)-N-[(1S)-1-(5-chloro-1H-benzimidazol-2-yl)-ethyl]-3-methyl-benzamide

(a) methyl 4-(6-bromo-hexanoyl-amino)-3-methyl-benzoate

A solution of 2.14 g (10 mmol) 6-bromo-hexanoylchloride in 5.0 ml THF is slowly added dropwise with stirring at ambient temperature to 1.65 g (10 mmol) methyl 4-amino-3-methyl-benzoate in 50 ml THF with 2 ml DIPEA. After 16 hours stirring at ambient temperature the mixture is evaporated down i. vac., the residue is dissolved in dichloromethane, washed twice with water and dried over sodium sulphate. The residue remaining after evaporation i. vac. is further reacted without any more purification.

Yield: 3.30 g (96%)

$R_f$ value: 0.40 (silica gel; petroleum ether/ethyl acetate=4:1)

$C_{15}H_{20}BrNO_3$ (342.24)

(b) methyl 4-(azepan-2-on-1-yl)-3-methyl-benzoate 3.20 g (9.35 mmol) of the product obtained in Example 5a is refluxed for 4 hours in a freshly prepared solution of 1.00 g (43.5 mmol) sodium in 80 ml of methanol. Then the mixture is evaporated down i. vac., the residue is acidified with 2-molar acetic acid and extracted with ethyl acetate. The combined organic phases are washed with water and dried over sodium sulphate. The residue obtained after evaporation i. vac. is further reacted without any more purification.

Yield: 1.90 g (contaminated product)
R_f value: 0.30 (silica gel; dichloromethane/ethanol=50:1)
C$_{15}$H$_{19}$NO$_3$ (261.32)
Mass spectrum: (M+H)$^+$=262

(c) 4-(azepan-2-on-1-yl)-3-methyl-benzoic acid 1.90 g of the product obtained in Example 5b in 30 ml of methanol is combined with 10 ml 2-molar sodium hydroxide solution and stirred for 16 hours at ambient temperature. After evaporation i. vac. the residue is combined with water and acidified with conc. hydrochloric acid. The precipitate formed is filtered off and dried. After dissolving in methanol and applying to silica gel the product is purified by chromatography on silica gel (eluting gradient: petroleum ether/ethyl acetate 70:30->50:50).
Yield: 0.23 g (10% over 2 steps)
R_f value: 0.10 (silica gel; petroleum ether/ethyl acetate=1:2)

C$_{14}$H$_{17}$NO$_3$ (247.30)
Mass spectrum: (M+H)$^+$=248

(d) 4-(azepan-2-on-1-yl)-N-[(1S)-1-(5-chloro-1H-benzimidazol-2-yl)-ethyl]-3-methyl-benzamide Prepared analogously to Example 1f from 4-(azepan-2-on-1-yl)-3-methyl-benzoic acid, TBTU, DIPEA and (1S)-1-(5-chloro-1H-benzimidazol-2-yl)ethylamine in THF and subsequent purification by chromatography on silica gel (eluting gradient: ethyl acetate/ethanol 95:5->90:10).
Yield: 61%
R_f value: 0.30 (silica gel; ethyl acetate)
C$_{23}$H$_{25}$ClN$_4$O$_2$ (424.93)
Mass spectrum: (M+H)$^+$=425/427 (chlorine isotope)
The following compounds were prepared analogously:

| No. | structural formula Name | yield | mass peak(s) | R_f value |
|---|---|---|---|---|
| 7 | 4-(azepan-2-on-1-yl)-N-[(1R)-1-(5-chloro-1H-benzimidazol-2-yl)-2-methoxy-ethyl]-3-benzamide | Σ: 1.1% | (M − H)$^-$ = 453/455 (chlorine isotope) | 0.60 (aluminum oxide, CH$_2$Cl$_2$/ C$_2$H$_5$OH 19:1) |
| 8 | 4-(azepan-2-on-1-yl)-N-[(1R)-(5-chloro-1H-benzimidazol-2-yl)-2-hydroxy-ethyl]-3-methyl-benzamide | Σ: 7.6% | (M + H)$^+$ = 441/443 (chlorine isotope) | 0.20 (silica gel, CH$_2$Cl$_2$/ C$_2$H$_5$OH 19:1) |
| 10 | N-[(1S)-1-(5-chloro-1H-benzimidazol-2-yl)-ethyl]-3-methyl-4-(pyrrolidin-2-on-1-yl)-benzamide | Σ: 72% | (M + H)$^+$ = 397/399 (chlorine isotope) | 0.50 (silica gel, CH$_2$Cl$_2$/ C$_2$H$_5$OH 9:1) |

| structural formula | | | | |
| --- | --- | --- | --- | --- |
| No. | Name | yield | mass peak(s) | $R_f$ value |
| 11 | 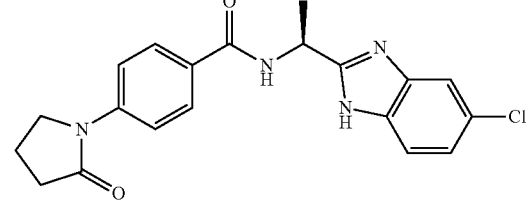 | Σ: 24% | (M + H)⁺ = 457/459 (chlorine isotope) | 0.63 (silica gel, $CH_2Cl_2$/ $C_2H_5OH$ 9:1) |
| | N-[(1S)-1-(5-chloro-1H-benzimidazol-2-yl)-3-methylsulphanyl-propyl]-3-methyl-4-(pyrrolidin-2-on-1-yl)-benzamide | | | |

Example 9

N-[(1S)-1-(5-chloro-1H-benzimidazol-2-yl)-ethyl]-4-(pyrrolidin-2-on-1-yl)-benzamide

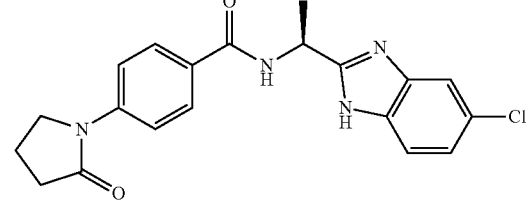

(a) 4-(pyrrolidin-2-on-1-yl)-benzoic acid 19.2 g (140 mmol) 4-amino-benzoic acid are refluxed for 20 hours together with 25.8 ml (180 mmol) ethyl 4-bromobutyrate in 100 ml DMF. After evaporation i. vac. the residue is combined with 100 ml of water and 50 ml petroleum ether and vigorously stirred for 50 minutes. The precipitate is filtered off, recrystallised from ethanol and dried at 80° C.

Yield: 9.36 g (33%)

$C_{11}H_{11}NO_3$ (205.22)

Mass spectrum: (M+H)⁺=206

(b) N-[(1S)-1-(5-chloro-1H-benzimidazol-2-yl)-ethyl]-4-(byrrolidin-2-on-1-yl)-benzamide Prepared analogously to Example 1f from 4-(pyrrolidin-2-on-1-yl)-benzoic acid, TBTU, DIPEA and (1S)-1-(5-chloro-1H-benzimidazol-2-yl)-ethylamine in THF and subsequent purification by washing the solution of the residue in ethyl acetate with water, dilute sodium hydrogen carbonate solution, water and sat. sodium chloride solution, drying over sodium sulphate and eliminating the solvent i. vac.

Yield: 61%

$R_f$ value: 0.50 (silica gel; dichloromethane/ethanol=9:1)

$C_{20}H_{19}ClN_4O_2$ (382.85)

Mass spectrum: (M+H)⁺=383/385 (chlorine isotope)

Example 12

3-chloro-N-[(1S)-1-(5-chloro-1H-benzimidazol-2-yl)-ethyl]-4-(4-N-methyl-[1,4]diazepan-1-yl)-benzamide

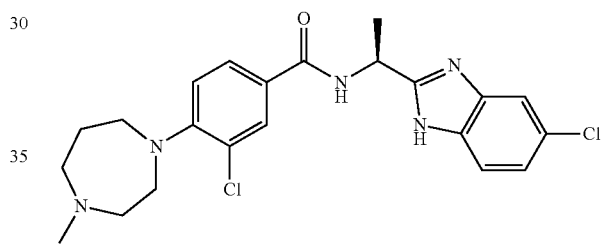

(a) 3-chloro-4-(4-N-methyl-[1,4]diazepan-1-yl)-benzonitrile

Prepared analogously to Example 1a from 3-chloro-4-fluoro-benzonitrile and 1-methyl-[1,4]diazepan in DIPEA with subsequent purification by chromatography on silica gel (eluting gradient: dichloromethane/ethanol 98:2->94:6).

Yield: 71%

$R_f$ value: 0.20 (silica gel; methylene chloride/ethanol=19:1)

$C_{13}H_{16}ClN_3$ (249.75)

Mass spectrum: (M+H)⁺=250/252 (chlorine isotope)

(b) 3-chloro-4-(4-N-methyl-[1,4]diazepan-1-yl)-benzoic acid

Prepared analogously to Example 1b from 3-chloro-4-(4-methyl-[1,4]diazepan-1-yl)-benzonitrile in 25% aqueous potassium hydroxide solution.

Yield: 99%

$C_{13}H_{17}ClN_2O_2$·HCl (268.74/305.21)

Mass spectrum: (M+H)⁺=269/271 (chlorine isotope)

(c) 3-chloro-N-[(1S)-1-(5-chloro-1H-benzimidazol-2-yl)-ethyl]-4-(4-N-methyl-[1,4]diazepan-1-yl)-benzamide Prepared analogously to Example 1f from 3-chloro-4-(4-methyl-[1,4]diazepan-1-yl)-benzoic acid, (S)-1-(5-chloro-1H-benzimidazol-2-yl)-ethylamine, TBTU and DIPEA in THF with subsequent purification by chromatography on silica gel (eluting gradient: petroleum ether/ethyl acetate 50:50->20:80).
Yield: 34%
$R_f$ value: 0.30 (silica gel; dichloromethane/ethanol=9:1+1% ammonia solution)
$C_{22}H_{25}Cl_2N_5O$ (446.38)
Mass spectrum: $(M+H)^+$=446/448/450 (chlorine isotope)

Example 13

3-chloro-N-[(1S)-1-(5-chloro-1H-benzimidazol-2-yl)-ethyl]-4-(2-methyl-pyrrolidin-1-yl)-benzamide

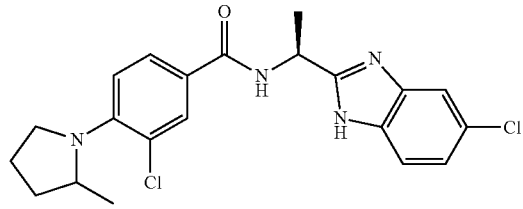 [SMILES: CC1CCCN1c1ccc(C(=O)N[C@@H](C)c2nc3cc(Cl)ccc3[nH]2)cc1Cl]

(a) 3-chloro-4-(2-methyl-pyrrolidin-1-yl]-benzonitrile 5.90 g (37.9 mmol) 3-chloro-4-fluoro-benzonitrile are dissolved in 65 ml DMF under a nitrogen atmosphere and combined with 5.45 g (39.5 mmol) potassium carbonate and 4.2 ml (3.5 g, 39.5 mmol) 2-methyl-pyrrolidine. After stirring for 2.5 days at 90° C. the reaction mixture is poured into 400 ml of water and extracted with ethyl acetate. The combined organic phases are washed several times with dilute and sat. sodium chloride solution, dried over magnesium sulphate and evaporated down i. vac. The residue remaining is further reacted without any more purification.
Yield: 7.90 g (94%)
$R_f$ value: 0.40 (silica gel; petroleum ether/ethyl acetate=9:1+0.5% ammonia solution)
$C_{12}H_{13}ClN_2$ (220.70)
Mass spectrum: $(M+H)^+$=221/223 (chlorine isotope)

(b) 3-chloro-4-(2-methyl-pyrrolidin-1-yl)-benzoic acid 8.0 g (40 mmol) of the product obtained in Example 13a are stirred in a mixture of 65 ml 10-molar sodium hydroxide solution and 65 ml of ethanol for 2.75 hours at 90° C. Then the reaction mixture is poured into ice water, combined with conc. hydrochloric acid and volatile organic constituents are evaporated down i. vac. The aqueous phase remaining is extracted with dichloromethane, combined with ice and adjusted to pH 4.5 with semiconcentrated hydrochloric acid and 2-normal potassium hydrogen sulphate solution. The resulting precipitate is stirred for another 10 minutes, then filtered off, washed with water and dried at 55° C.
Yield: 8.30 g (87%)
$R_f$ value: 0.55 (silica gel; petroleum ether/ethyl acetate=6:4+1% acetic acid)
$C_{12}H_{14}ClNO_2$ (238.72)
Mass spectrum: $(M+H)^+$=240/242 (chlorine isotope)

(c) 3-chloro-N-[(1S)-1-(5-chloro-1H-benzimidazol-2-yl)-ethyl)-4-(2-methyl-pyrrolidin-1-yl)-benzamide Prepared analogously to Example 1f from 3-chloro-4-(2-methyl-pyrrolidin-1-yl)-benzoic acid, (1S)-1-(5-chloro-1H-benzimidazol-2-yl)-ethylamine, TBTU and TEA in DMF, then precipitated by pouring into dilute sodium hydrogen carbonate solution, filtering and washing with water. Then the product is dried at 55° C.
Yield: 92%
$R_f$ value: 0.66 (silica gel; dichloromethane/ethanol=9:1)
$C_{21}H_{22}Cl_2N_4O$ (417.34)
Mass spectrum: $(M-H)^-$=415/417/419 (chlorine isotope)
The following compounds were prepared analogously:

| No. | structural formula Name | yield | mass peak(s) | $R_f$ value/$R_t$ value |
|---|---|---|---|---|
| 14 | ![structure] N-[(1S)-1-(5-chloro-1H-benzimidazol-2-yl)-ethyl]-3-chloro-4-(morpholin-4-yl)-benzamide | Σ: 11% | $(M + H)^+$ = 419/421/423 (chlorine isotope) | 0.55 (silica gel, petroleum ether/ $CH_3COOC_2H_5$ 19:1) |
| 15 | ![structure] | Σ: 19% | $(M + H)^+$ = 421/423 (chlorine isotope) | 0.30 (silica gel, petroleum ether/ $CH_3COOC_2H_5$ 1:1) |

-continued

| No. | structural formula Name | yield | mass peak(s) | $R_f$ value/$R_t$ value |
|---|---|---|---|---|
| | N-[(1S)-1-(5-chloro-1H-benzimidazol-2-yl)-ethyl]-3,5-difluoro-4-(morpholin-4-yl)-benzamide | | | |
| 16 | | Σ: 17% | $(M+H)^+$ = 483/485 (chlorine isotope) | 3.46 min |
| | N-[(1R)-1-(5-chloro-1H-benzimidazol-2-yl)-2-methoxy-ethyl]-3-trifluoromethyl-4-(morpholin-4-yl)-benzamide | | | |
| 17 | | Σ: 13% | $(M+H)^+$ = 465/467 (chlorine isotope) | 3.21 min |
| | 4-(azepan-1-yl)-N-[(1S)-1-(5-chloro-1H-benzimidazol-2-yl)-ethyl]-3-trifluoromethyl-benzamide | | | |
| 18 | | Σ: 20% | $(M+H)^+$ = 431/433/435 (chlorine isotope | 3.02 min |
| | 4-(azepan-1-yl)-3-chloro-N-[(1S)-1-(5-chloro-1H-benzimidazol-2-yl)-ethyl]-benzamide | | | |
| 19 | | Σ: 49% | $(M+H)^+$ = 417/419/421 (chlorine isotope) | 0.47 (silica gel, $CH_2Cl_2$/ isopropanol 19:1) |
| | 3-chloro-N-[(1S)-1-(5-chloro-1H-benzimidazol-2-yl)-ethyl]-4-(piperidin-1-yl)-benzamide | | | |
| 20 | | Σ: 6.2% | $(M+H)^+$ = 433/435/437 (chlorine isotope) | 2.61 min |
| | 3-chloro-N-[(1S)-1-(5-chloro-1H-benzimidazol-2-yl)-ethyl]-4-([1,4]oxazepan-4-yl)-benzamide | | | |

| No. | structural formula Name | yield | mass peak(s) | $R_f$-value/$R_t$ value |
|---|---|---|---|---|
| 37 | N-[(1S)-1-(5-chloro-1H-benzimidazol-2-yl)-ethyl]-4-(3,5-dimethylpiperidin-1-yl)-benzamide | Σ: 9.4% | (M + H)⁺ = 411/413 (chlorine/ isotope) | 0.53 (silica gel, CH₂Cl₂/CH₃OH 19:1) |
| 38 | 3-chloro-N-[(1S)-1-(5-chloro-1H-benzimidazol-2-yl)-ethyl]-4-(3,4-di-dehydro-piperidin-1-yl)-benzamide | Σ: 20% | (M − H)⁻ = 413/415/417 (chlorine isotope) | 2.84 min |
| 50 | 3-chloro-N-[(1S)-1-(5-chloro-1H-benzimidazol-2-yl)-ethyl]-4-[2-(4-methyl-piperazin-1-yl-methyl)-piperidin-1-yl]-benzamide | Σ: 1.2% | (M + H)⁺ = 529/531/533 (chlorine isotope) | 0.29 (silica gel, CH₂Cl₂/ CH₃OH 9:1) 2.38 min |

Example 21

N-[(1R)-1-(5-chloro-1H-benzimidazol-2-yl)-2-methoxy-ethyl]-4-(morpholin-3-on-4-yl)-3-trifluoromethyl-benzamide

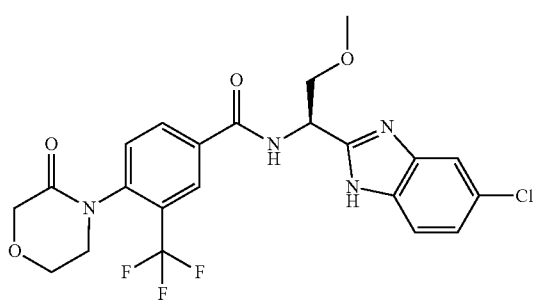 [SMILES: COC[C@H](NC(=O)c1ccc(N2CCOCC2=O)c(C(F)(F)F)c1)c1nc2cc(Cl)ccc2[nH]1]

(a) 4-(morpholin-3-on-4-yl)-3-trifluoromethyl-benzoic acid 1.00 g (3.63 mmol) 4-(morpholin-4-yl)-3-trifluoromethyl-benzoic acid (prepared by synthesis sequence analogously to Example 13a and 13b) is suspended in 40 ml of water and 150 mg (3.75 mmol) sodium hydroxide are added. Then 1.73 g (10.92 mmol) potassium permanganate are added and the mixture is stirred for 1.5 hours at 45° C. Then the reaction mixture is cooled in the ice bath and sodium thiosulphate is added until total decolorisation is obtained. After extraction 3 times with ethyl acetate the combined organic phases are dried over sodium sulphate evaporated down i. vac. After application of the residue to silica gel it is purified by chromatography on silica gel (eluant: dichloromethane/methanol 95:5).

Yield: 340 mg (32%)
C₁₂H₁₀F₃NO₄ (289.21)
Mass spectrum: (M+H)⁺=290

(b) N'-(2-amino-4-chloro-phenyl)-N-Boc-(S)-O-methyl-serinamide and N'-(2-amino-5-chloro-phenyl)-N-Boc-(S)-O-methyl-serinamide 30.0 g (137 mmol) N-Boc-(S)-O-methyl-serine are dissolved together with 21.9 g (154 mmol) 4-chloro-1,2-phenylenediamine in 658 ml THF, and 43.9 ml (316 mmol) triethylamine and 103 ml (173 mmol) of a 50% solution of PPA in ethyl acetate are added with stirring in the ice bath. After 15 minutes stirring in the ice bath the mixture is heated to ambient temperature, poured into water and the aqueous phase is extracted with ethyl acetate. The combined organic phases are washed with sat. sodium carbonate solution and water, dried over sodium sulphate and evaporated down i. vac. The residue is purified by chromatography on silica gel (eluting gradient: dichloromethane/methanol=30:1->9:1).

Yield: 33.47 g (72%) mixture of the two regioisomers
$C_{15}H_{22}ClN_3O_4$ (343.81)
Mass spectrum: (M−H)$^-$=342/344 (chlorine isotope)
$R_f$ value: 0.80 (silica gel; dichloromethane/methanol=9:1)

(c) (1R)-N-Boc-1-(5-chloro-1H-benzimidazol-2-yl)-2-methoxy-ethylamine 26.01 g (75.65 mmol) of the mixture obtained in Example 21b are dissolved in 1500 ml of toluene and 20.8 ml (364 mmol) acetic acid and 10.0 g molecular sieve, 4 Å, are added. The reaction mixture is stirred for 5 hours at 60° C. The reaction mixture is filtered, washed again with ethyl acetate and the organic phase is washed with semisat. sodium hydrogen carbonate solution, dried over sodium sulphate and evaporated down i. vac. The residue is stirred with diethyl ether and the crystals formed are suction filtered. The filtrate is evaporated down i. vac. and the residue is purified by three lots of chromatography on silica gel (eluting gradient: dichloromethane/methanol 80:1->50:1).

Yield: 13.85 g (56%)
$C_{15}H_{20}ClN_3O_3$ (325.79)
Mass spectrum: (M+H)$^+$=326/328 (chlorine isotope)
$R_f$ value: 0.29 (silica gel; dichloromethane/methanol=30:1)

(d) (1R)-1-(5-chloro-1H-benzimidazol-1-yl)-2-methoxy-ethylamine 0.50 g (1.54 mmol) (1R)-N-Boc-1-(5-chloro-1H-benzimidazol-2-yl)-2-methoxy-ethylamine in 1.5 ml dichloromethane are combined with 1.54 ml (20.0 mmol) TFA and stirred for 2 h at ambient temperature. The mixture is then poured into sat. sodium hydrogen carbonate solution and after thorough mixing the aqueous phase is extracted with dichloromethane and ethyl acetate. The combined organic phases are dried over sodium sulphate and purified by chromatography on silica gel (eluant: dichloromethane/methanol=9:1+ 1% conc. ammonia solution).

Yield: 0.35 g (quant.)
$C_{10}H_{12}ClN_3O$ (225.68)
Mass spectrum: (M−H)$^-$=224/226 (chlorine isotope)
$R_f$ value: 0.40 (silica gel, dichloromethane/methanol 9:1+ 1% conc. ammonia solution)

(e) N-[(1R)-1-(5-chloro-1H-benzimidazol-2-yl)-2-methoxy-ethyl]-4-(morpholin-3-on-4-yl)-3-trifluoromethyl-benzamide Prepared analogously to Example 1f from 4-(morpholin-3-on-4-yl)-3-trifluoromethyl-benzoic acid, (1R)-1-(5-chloro-1H-benzimidazol-2-yl)-2-methoxy-ethylamine, TBTU and NMM in DMF, then precipitation by pouring into water, filtering and drying i. vac.

Yield: 63%
$R_f$ value: 0.57 (silica gel; dichloromethane/methanol=9:1)
$C_{22}H_{20}ClF_3N_4O_4$ (496.88)
Mass spectrum: (M+H)$^+$=497/499 (chlorine isotope)
The following compounds were prepared analogously:

| No. | structural formula Name | Yield | mass peaks(s) | $R_f$ value or $R_t$ |
|---|---|---|---|---|
| 25 | 4-(azepan-2-on-1-yl)-3-chloro-N-[(1R)-1-(5-chloro-1H-benzimidazol-2-yl)-2-methoxy-ethyl]-benzamide | Σ: 2.0% | (M + H)$^+$ = 475/477/479 (chlorine isotope) | 2.57 min |
| 26 | 4-(azepan-2-on-1-yl)-N-[(1R)-1-(5-chloro-1H-benzimidazol-2-yl)-2-methoxy-ethyl]-3-trifluoromethyl-benzamide | Σ: 29% | (M + H)$^+$ = 509/511 (chlorine isotope) | 2.65 min |

-continued

| No. | structural formula Name | Yield | mass peaks(s) | $R_f$ value or $R_t$ |
|---|---|---|---|---|
| 44 | 3-chloro-N-[(1R)-1-(5-chloro-1H-benzimidazol-2-yl)-2-methoxy-ethyl]-4-([1,4]oxazepan-5-on-4-yl)-benzamide | Σ: 8.5% | $(M + H)^+$ = 477/479/481 (chlorine isotope) | 0.47 (silica gel, $CH_2Cl_2/CH_3OH$ 95:5) 2.37 min |
| 45 | 3-chloro-N-[(1R)-1-(5-chloro-1H-benzimidazol-2-yl)-2-methoxy-ethyl]-4-([1,4]oxazepan-3-on-4-yl)-benzamide | Σ: 2.2% | $(M + H)^+$ = 477/479/481 (chlorine isotope) | 0.45 (silica gel, $CH_2Cl_2/CH_3OH$ 95:5) 2.41 min |
| 52 | 3-chloro-N-[(1S)-1-(5-chloro-1H-benzimidazol-2-yl)-ethyl]-4-(morpholin-3-on-4-yl)-benzamide | Σ: 7.2% | $(M - H)^-$ = 431/433/435 (chlorine isotope) | 0.70 (silica gel, $CH_3COOC_2H_5/CH_3OH$ 9:1) |
| 81 | 3-chloro-N-[(1R)-1-(5-chloro-1H-benzimidazol-2-yl)-2-methoxy-ethyl]-4-(morpholin-3-on-4-yl)-benzamide | Σ: 2.9% | $(M + H)^+$ = 463/465/467 (chlorine isotope) | 0.44 (silica gel, $CH_3COOC_2H_5/CH_3OH$ 95:5 + $CH_3COOH$) |
| 97 | 3-bromo-N-[(1R)-1-(5-chloro-1H-benzimidazol-2-yl)-2-methoxy-ethyl]-4-(morpholin-3-on-4-yl)-benzamide | Σ: 1.0% | $(M - H)^-$ = 506/508/510 (bromine and chlorine isotope) | 2.36 min |

Example 22

N-[(1R)-1-(5-chloro-1H-benzimidazol-2-yl)-2-methoxy-ethyl]-3-methyl-4-(morpholin-3-on-4-yl)-benzamide

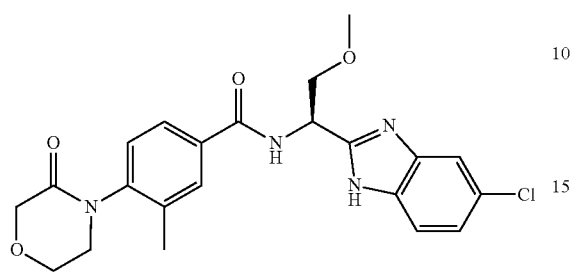

Prepared analogously to Example 1f from 3-methyl-4-(morpholin-3-on-4-yl)-benzoic acid (prepared by synthesis sequence analogously to Example 30a, 2d and 21a), (1R)-1-(5-chloro-1H-benzimidazol-2-yl)-2-methoxy-ethylamine, TBTU and NMM in DMF, then pouring into water, extracting with ethyl acetate, drying over sodium sulphate, evaporation i. vac. and purifying by chromatography on silica gel (eluting gradient: ethyl acetate/isopropanol/ethanol 9:1:0->9:0:1).

Yield: 99%

$R_f$ value: 0.13 (silica gel; dichloromethane/isopropanol=19:1)

$C_{22}H_{23}ClN_4O_4$ (442.91)

Mass spectrum: $(M+H)^+$=443/445 (chlorine isotope)

The following compounds were prepared analogously:

| No. | structural formula Name | Yield | mass peak(s) | $R_f$ value or $R_t$ |
|---|---|---|---|---|
| 23 | 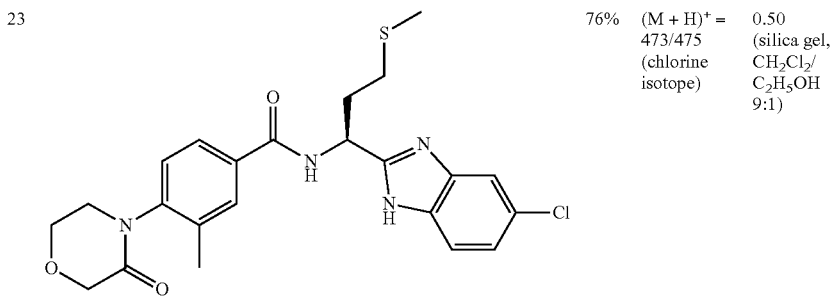<br>N-[(1S)-1-(5-chloro-1H-benzimidazol-2-yl)-3-methylsulphanyl-propyl]-3-methyl-4-(morpholin-3-on-4-yl)-benzamide | 76% | $(M+H)^+$ = 473/475 (chlorine isotope) | 0.50 (silica gel, CH$_2$Cl$_2$/ C$_2$H$_5$OH 9:1) |
| 24 | 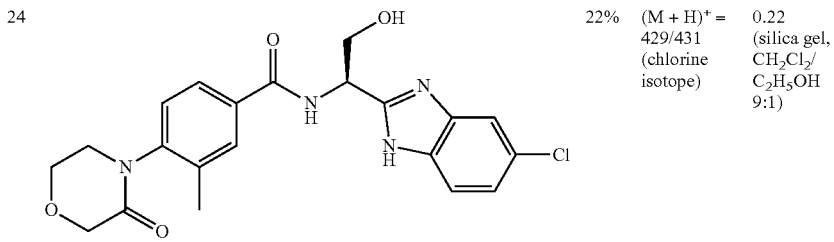<br>N-[(1R)-1-(5-chloro-1H-benzimidazol-2-yl)-2-hydroxy-ethyl]-3-methyl-4-(morpholin-3-on-4-yl)-benzamide | 22% | $(M+H)^+$ = 429/431 (chlorine isotope) | 0.22 (silica gel, CH$_2$Cl$_2$/ C$_2$H$_5$OH 9:1) |
| 49 | 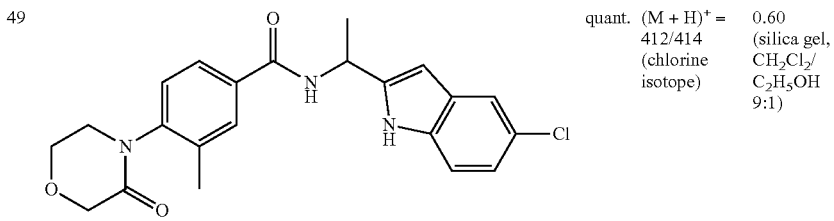<br>N-[1-(5-chloro-1H-indol-2-yl)-ethyl]-3-methyl-4-(morpholin-3-on-4-yl)-benzamide | quant. | $(M+H)^+$ = 412/414 (chlorine isotope) | 0.60 (silica gel, CH$_2$Cl$_2$/ C$_2$H$_5$OH 9:1) |

Example 27

N-[(1S)-1-(5-chloro-1H-benzimidazol-2-yl)-ethyl]-4-(morpholin-3-on-4-yl)-benzamide

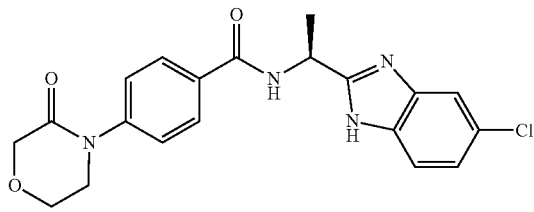 [SMILES: C[C@H](NC(=O)c1ccc(N2CCOCC2=O)cc1)c1nc2cc(Cl)ccc2[nH]1]

254 mg (1.15 mmol) 4-(morpholin-3-on-4-yl)-benzoic acid (prepared by synthesis sequence analogously to Example 30a, 2d and 21a) are placed in 5 ml DMF and 428 mg (1.0 mmol) PfTU and 514 µl (3.0 mmol) DIPEA are added. After stirring at ambient temperature for 10 minutes 232 mg (1.0 mmol) (1S)-1-(5-chloro-1H-benzimidazol-2-yl)-ethylamine-hydrochloride are added and the mixture is stirred for 16 hours at ambient temperature. Then the reaction mixture is filtered through basic aluminium oxide and evaporated down i. vac. The residue is purified by chromatography on silica gel (eluting gradient: dichloromethane/methanol 100:0->90:10), the corresponding fractions are evaporated down i. vac., the residue is dissolved in acetonitrile/water and lyophilised.

Yield: 77%
$C_{20}H_{19}ClN_4O_3$ (398.85)
Mass spectrum: (M+H)$^+$=399/401 (chlorine isotope)
The following compound is prepared analogously:

(a) 4-fluoro-3-methyl-benzoic acid chloride 14.00 g (90.8 mmol) 4-fluoro-3-methyl-benzoic acid are refluxed for 1 hour together with 50 ml of thionyl chloride and then evaporated down i. vac. The residue is further reacted without any more purification.

Yield: 15.70 g (quantitative)
$C_8H_8ClFO$ (172.59)

(b) 4-fluoro-3-methyl-benzamide 15.70 g (91.0 mmol) 4-fluoro-3-methyl-benzoic acid chloride dissolved in 30 ml THF are added dropwise to 300 ml of conc. ammonia solution and then stirred for 2 hours at ambient temperature. The precipitate formed is filtered off, washed with water and dried.

Yield: 10.00 g (72%)
$C_8H_8FNO$ (153.16)
$R_f$ value: 0.31 (aluminium oxide; dichloromethane/methanol=50:1)

(c) 4-fluoro-3-methyl-benzonitrile 10.00 g (65.29 mmol) 4-fluoro-3-methyl-benzoic acid amide are stirred together with 50 ml phosphorus oxychloride for 4 hours at 60° C. and then evaporated down i. vac. The residue is poured into ice water, the resulting precipitate is filtered off and washed with water. After being taken up in ethyl acetate the organic phase is washed with sat. potassium carbonate solution, dried over sodium sulphate and evaporated down completely i. vac.

Yield: 8.00 g (91%)
$C_8H_6FN$ (135.14)
$R_f$ value: 0.84 (silica gel; dichloromethane)

| No. | structural formula Name | Yield | mass peak(s) |
|---|---|---|---|
| 28 | 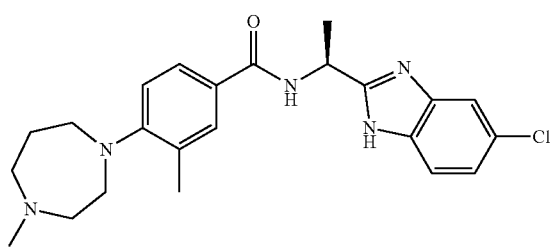<br>N-[(1S)-1-(5-chloro-1H-benzimidazol-2-yl)-ethyl]-3-methyl-4-(morpholin-3-on-4-yl)-benzamide | 80% | (M + H)$^+$ = 413/415 (chlorine isotope) |

Example 29

N-[(1S)-1-(5-chloro-1H-benzimidazol-2-yl)-ethyl]-3-methyl-4-(4-N-methyl-[1,4]diazepan-1-yl)-benzamide

(d) 3-methyl-4-(4-N-methyl-[1,4]diazepan-1-yl)-benzonitrile 7.00 g (51.8 mmol) 4-fluoro-3-methyl-benzonitrile are heated to 110° C. together with 1-N-methyl-[1,4]diazepan for 1 week with stirring. After evaporation i. vac. the residue is separated on aluminium oxide (eluant: dichloromethane) and the corresponding fractions are again purified on silica gel (eluting gradient: dichloromethane/methanol 100:1->9:1).

Yield: 1.70 g (14%)
$C_{14}H_{19}N_3$ (229.33)
Mass spectrum: (M+H)$^+$=230
$R_f$ value: 0.25 (silica gel; dichloromethane/methanol=9:1)

(e) 3-methyl-4-(4-N-methyl-[1,4]diazepan-1-yl)-benzoic acid

Prepared analogously to Example 1b from 3-methyl-4-(4-N-methyl-[1,4]diazepan-1-yl)-benzonitrile with 25% potassium hydroxide solution by refluxing for 36 hours. After evaporation i. vac. the residue is separated on aluminium oxide (eluant: dichloromethane) and the corresponding fractions are again purified on silica gel (eluting gradient: dichloromethane/methanol 100:1->9:1).

Yield: 14%
$C_{14}H_{19}N_2O_2$ (248.33)
Mass spectrum: $(M+H)^+$=249
$R_f$ value: 0.30 (RP-18; methanol/5% aqueous sodium chloride solution=6:4)

(f) 3-methyl-4-(4-N-methyl-[1,4]diazepan-1-yl)-benzoic acid chloride

Prepared analogously to Example 29a from 3-methyl-4-(4-N-methyl-[1,4]diazepan-1-yl)-benzoic acid and thionyl chloride.

Yield: quantitative
$C_{14}H_{19}ClN_2O \cdot HCl$ (266.77/303.23)

(g) N-[1S)-1-(5-chloro-1H-benzimidazol-2-yl)-ethyl]-3-methyl-4-(4-N-methyl-[1,4]diazepan-1-yl)-benzamide 489 mg (1.61 mmol) 3-methyl-4-(4-N-methyl-[1,4]diazepan-1-yl)-benzoic acid chloride are placed together with 400 mg (3.96 mmol) TEA in 10 ml THF at ambient temperature and a solution of 433 mg (1.61 mmol) (1S)-1-(5-chloro-1H-benzimidazol-2-yl)-ethyl amine is added dropwise with stirring. After 16 hours stirring at ambient temperature the mixture is evaporated down i. vac., the residue is combined with water and extracted with ethyl acetate. The combined organic phases are washed with sat. sodium chloride solution, dried over sodium sulphate and evaporated down i. vac. The residue is purified by chromatography on aluminium oxide (eluant: dichloromethane/methanol 100:1). The fractions evaporated down are treated with ethereal hydrochloric acid, after total concentration evaporated twice with ethyl acetate and diethyl ether and dried i. vac. at 70° C.

Yield: 120 mg (16%)
$C_{23}H_{28}ClN_5O \cdot HCl$ (462.43/425.96)
Mass spectrum: $(M+H)^+$=426/428 (chlorine isotope)
$R_f$ value: 0.47 (aluminium oxide; dichloromethane/methanol 19:1)

Example 30

N-[(1S)-1-(5-chloro-1H-benzimidazol-2-yl)-ethyl]-3-methyl-4-(piperazin-1-yl)-benzamide

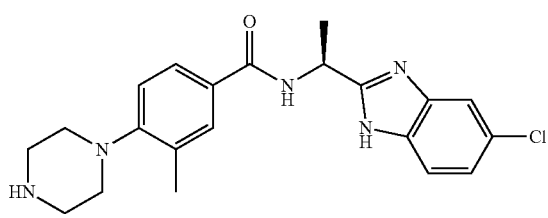 [SMILES: Cc1cc(C(=O)N[C@@H](C)c2nc3cc(Cl)ccc3[nH]2)ccc1N1CCNCC1]

(a) methyl 4-(N-Boc-piperazin-1-yl)-3-methyl-benzoate 4.00 g (17.5 mmol) 4-bromo-3-methyl-benzoate methyl are suspended together with 3.92 g (21.0 mmol) N-Boc-piperazine, 39.2 mg (175 μmol) palladium (II)acetate, 50.7 mg (175 μmol) tri-tert.-butyl-phosphonium-tetrafluoroborate and 11.12 g (52.4 mmol) potassium phosphate in 35 ml of toluene and under an argon atmosphere heated to 150° C. for 10 minutes in a microwave oven. Then the reaction mixture is poured into water, stirred vigorously and extracted 3 times with ethyl acetate. The combined organic phases are dried over sodium sulphate, applied to silica gel and purified by chromatography on silica gel (eluant: dichloromethane/methanol 80:1).

Yield: 1.42 g (24%)
$C_{18}H_{26}N_2O_4$ (334.42)
Mass spectrum: $(M+H)^+$=335
$R_f$ value: 0.52 (silica gel; dichloromethane/methanol=50:1)

(b) 4-(N-Boc-piperazin-1-yl)-3-methyl-benzoic acid 1.42 g (4.24 mmol) of methyl 4-(N-Boc-piperazin-1-yl)-3-methyl-benzoate are dissolved in 7 ml THF and 9.25 ml of water and 893 mg (21.3 mmol) lithium hydroxide-monohydrate are added. After stirring for 16 hours at ambient temperature the mixture is heated to 45° C. for 2 hours. Then another 893 mg (21.3 mmol) lithium hydroxide monohydrate are added and the mixture is stirred for 4 days at ambient temperature. Then it is neutralised with 1-molar hydrochloric acid and the reaction mixture is extracted with ethyl acetate. The combined organic phases are dried over sodium sulphate and evaporated down completely i. vac.

Yield: 1.29 g (95%)
$C_{17}H_{24}N_2O_4$ (320.39)
Mass spectrum: $(M+H)^+$=321
$R_f$ value: 0.29 (silica gel; dichloromethane/methanol=15:1)

(c) 4-(N-Boc-piperazin-1-yl)-N-[(1S)-1-(5-chloro-1H-benzimidazol-2-yl)-ethyl)-3-methyl-benzamide Prepared analogously to Example 1f from 4-(N-Boc-piperazin-1-yl)-3-methyl-benzoic acid, (1S)-1-(5-chloro-1H-benzimidazol-2-yl)-ethylamine, TBTU and NMM in DMF, then stirring into conc. sodium hydrogen carbonate solution, extraction with ethyl acetate, drying over sodium sulphate, evaporation i. vac. and purification of the residue by chromatography on silica gel (eluting gradient: dichloromethane/methanol 50:1->15:1).

Yield: 85%
$R_f$ value: 0.15 (silica gel; dichloromethane/methanol=30:1)
$C_{26}H_{32}ClN_5O_3$ (498.03)
Mass spectrum: $(M+H)^+$=498/500 (chlorine isotope)

(d) N-[(1S)-1-(5-chloro-1H-benzimidazol-2-yl)-ethyl]-3-methyl-4-(piperazin-1-yl)-benzamide Prepared analogously to Example 1g from 4-(N-Boc-piperazin-1-yl)-N-[(1S)-1-(5-chloro-1H-benzimidazol-2-yl)-ethyl)-3-methyl-benzamide and TFA in dichloromethane.

Yield: quantitative
$C_{21}H_{24}ClN_5O$ (397.91)
Mass spectrum: $(M+H)^+$=398/400 (chlorine isotope)
$R_f$ value: 0.14 (silica gel; dichloromethane/methanol=9:1)

The following compound is prepared analogously:

| No. | structural formula Name | Yield | mass peak(s) | $R_f$ value or $R_f$ |
|---|---|---|---|---|
| 65 | 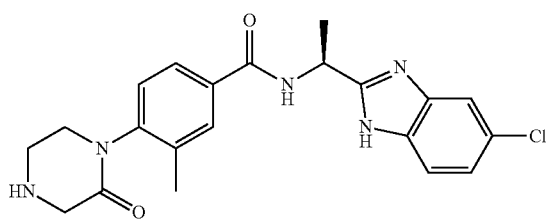<br>N-[(1R)-1-(5-chloro-1H-benzimidazol-2-yl)-2-methoxy-ethyl]-3-methyl-4-(piperazin-1-yl)-benzamide | Σ: 5.9% | $(M + H)^+$ = 428/430 (chlorine isotope) | 0.11 (silica gel, $CH_2Cl_2$/ $CH_3OH$ 9:1) |

Example 31

N-[(1S)-1-(5-chloro-1H-benzimidazol-2-yl)-ethyl]-3-methyl-4-(piperazin-2-on-1-yl)-benzamide

(a) methyl 4-(N-Boc-piperazin-2-on-1-yl)-3-methyl-benzoate 758 mg (3.31 mmol) methyl 4-bromo-3-methyl-benzoate are suspended together with 796 mg (21.0 mmol) 4-N-Boc-piperazin-2-one, 31.8 mg (167 μmol) copper (I)iodide, 35.1 μl (330 μmol) N,N'-dimethyl-ethylenediamine and 0.92 g (6.62 mmol) potassium carbonate in 6.6 ml of toluene and under an argon atmosphere heated to 140° C. in a microwave oven with stirring for 1.5 hours. Then the reaction mixture is poured into water, stirred vigorously and extracted 3 times with ethyl acetate. The combined organic phases are dried over sodium sulphate, applied to silica gel and purified by chromatography on silica gel (eluant: dichloromethane/methanol 50:1).

Yield: 679 mg (59%)
$C_{18}H_{24}N_2O_5$ (348.40)
Mass spectrum: $(M+H)^+$=349
$R_f$ value: 0.25 (silica gel; dichloromethane/methanol=50:1)

(b) 4-(N-Boc-piperazin-2-on-1-yl)-3-methyl-benzoic acid 775 mg (2.22 mmol) methyl 4-(N-Boc-piperazin-2-on-1-yl)-3-methyl-benzoate are dissolved in 3.7 ml THF and 4.9 ml of water as well as 468 mg (11.2 mmol) lithium hydroxide-monohydrate are added. After stirring for 16 hours at ambient temperature the mixture is neutralised with 1-molar hydrochloric acid and the reaction mixture is extracted with ethyl acetate. The combined organic phases are dried over sodium sulphate and evaporated down completely i. vac.

Yield: 664 mg (89%)
$C_{17}H_{22}N_2O_5$ (334.38)
Mass spectrum: $(M+H)^+$=335
$R_f$ value: 0.31 (silica gel; dichloromethane/methanol=15:1)

(c) 4-(N-Boc-piperazin-2-on-1-yl)-N-[(1S)-1-(5-chloro-1H-benzimidazol-2-yl)-ethyl)-3-methyl-benzamide Prepared analogously to Example 1f from 4-(N-Boc-piperazin-1-yl)-3-methyl-benzoic acid, (1S)-1-(5-chloro-1H-benzimidazol-2-yl)-ethylamine, TBTU and NMM in DMF, then stirring into conc. sodium hydrogen carbonate solution, extraction with ethyl acetate, drying over sodium sulphate, evaporation i. vac. and purification of the residue by chromatography on silica gel (eluant: dichloromethane/methanol 30:1).

Yield: 71%
$R_f$ value: 0.30 (silica gel; dichloromethane/methanol=15:1)
$C_{26}H_{30}ClN_5O_4$ (512.01)
Mass spectrum: $(M+H)^+$=512/514 (chlorine isotope)

(d) N-[(1S)-1-(5-chloro-1H-benzimidazol-2-yl)-ethyl]-3-methyl-4-(piperazin-2-on-1-yl)-benzamide Prepared analogously to Example 1g from 4-(N-Boc-piperazin-1-yl)-N-[(1S)-1-(5-chloro-1H-benzimidazol-2-yl)-ethyl]-3-methyl-benzamide and TFA in dichloromethane.

Yield: 36%
$C_{21}H_{22}ClN_5O_2$ (411.90)
Mass spectrum: $(M+H)^+$=412/414 (chlorine isotope)
$R_f$ value: 0.42 (silica gel; dichloromethane/methanol=9:1)

The following compounds were prepared analogously:

| No. | structural formula Name | Yield | mass peak(s) | $R_f$ value or $R_t$ |
|---|---|---|---|---|
| 66 | N-[(1R)-1-(5-chloro-1H-benzimidazol-2-yl)-2-methoxy-ethyl]-3-methyl-4-(piperazin-2-on-1-yl)-benzamide | Σ: 17% | $(M+H)^+ =$ 442/444 (chlorine isotope) | 0.18 (silica gel, $CH_2Cl_2$/ $CH_3OH$ 9:1) |
| 98 | N-[(1S)-1-(5-chloro-1H-benzimidazol-2-yl)-ethyl]-3-methyl-4-(7-oxo-[1,4]diazepan-1-yl)-benzamide | Σ: 0.11% | $(M+H)^+ =$ 426/428 (chlorine isotope) | |

Example 32

N-[(1S)-1-(5-chloro-1H-benzimidazol-2-yl)-ethyl]-3-methyl-4-(piperidin-2-on-1-yl)-benzamide

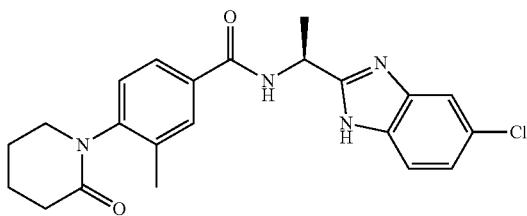 [SMILES: Cc1cc(C(=O)N[C@@H](C)c2nc3cc(Cl)ccc3[nH]2)ccc1N1CCCCC1=O]

(a) methyl 3-methyl-4-(piperidin-2-on-1-yl)-benzoate

Prepared analogously to Example 31a from methyl 4-bromo-3-methyl-benzoate and piperidin-2-one in the presence of copper (I)iodide, N,N'-dimethyl-ethylenediamine and potassium carbonate in toluene and dioxane under an argon atmosphere.
Yield: 34%
$C_{14}H_{17}NO_3$ (247.30)
Mass spectrum: $(M+H)^+ =248$
$R_f$ value: 0.21 (silica gel; petroleum ether/ethyl acetate=1:1)

(b) 3-methyl-4-(piperidin-2-on-1-yl)-benzoic acid

Prepared analogously to Example 2d from methyl 3-methyl-4-(piperidin-2-on-1-yl)-benzoate and 1-molar sodium hydroxide solution in methanol.
Yield: 83%
$C_{13}H_{15}NO_3$ (233.27)
Mass spectrum: $(M+H)^+ =234$
$R_f$ value: 0.51 (silica gel; ethyl acetate/ethanol=9:1+1% conc. ammonia solution)

(c) N-[(1S)-1-(5-chloro-1H-benzimidazol-2-yl)-ethyl)-3-methyl-4-(piperidin-2-on-1-yl)-benzamide Prepared analogously to Example 1f from 3-methyl-4-(piperidin-1-yl)-benzoic acid, (1S)-1-(5-chloro-1H-benzimidazol-2-yl)-ethylamine, TBTU and NMM in DMF, then stirring into ice water, combining with ammonia solution, filtering, taking up in dichloromethane, evaporation i. vac. and purification of the residue by chromatography on silica gel (eluting gradient: ethyl acetate/(methanol/conc. ammonia solution 19:1) 1:0->9:1).
Yield: 32%
$R_f$ value: 0.30 (silica gel; ethyl acetate/ethanol=9:1+1% acetic acid)
$C_{22}H_{23}ClN_4O_2$ (410.91)
Mass spectrum: $(M+H)^+ =411/413$ (chlorine isotope)

The following compounds were prepared analogously:

| No. | structural formula Name | Yield | mass peak(s) | $R_f$ value or $R_t$ |
|---|---|---|---|---|
| 55 | 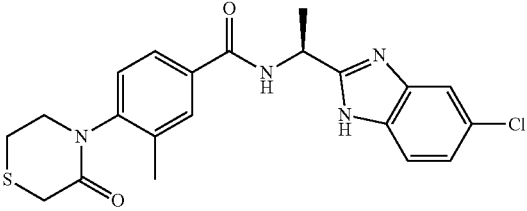 [SMILES: Cc1cc(C(=O)N[C@@H](C)c2nc3cc(Cl)ccc3[nH]2)ccc1N1CCSCC1=O] N-[(1S)-1-(5-chloro-1H-benzimidazol-2-yl)-ethyl]-3-methyl-4-(thiomorpholin-3-on-4-yl)-benzamide | Σ: 4.5% | $(M + H)^+$ = 429/431 (chlorine isotope) | 0.40 (silica gel, $CH_3COOC_2H_5$/ $C_2H_5OH$ 19:1 + 1% $NH_3$) |
| 56 | 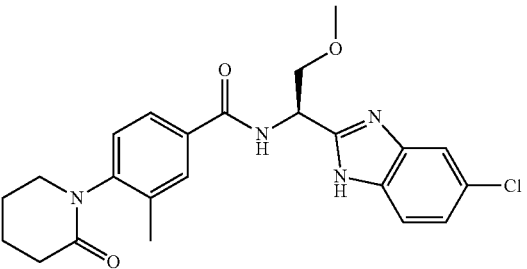 [SMILES: COC[C@H](NC(=O)c1ccc(N2CCCCC2=O)c(C)c1)c1nc2cc(Cl)ccc2[nH]1] N-[(1R)-1-(5-chloro-1H-benzimidazol-2-yl)-2-methoxy-ethyl]-3-methyl-4-(piperidin-2-on-1-yl)-benzamide | Σ: 16% | $(M + H)^+$ = 441/443 (chlorine isotope) | 0.30 (silica gel, $CH_3COOC_2H_5$/ $C_2H_5OH$ 9:1 + 1% $NH_3$) |
| 80 | 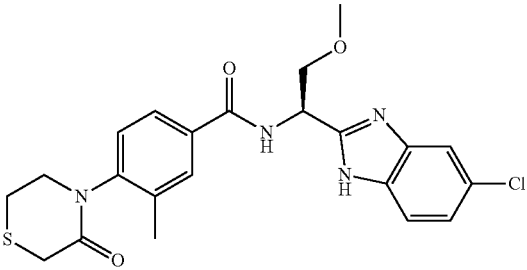 [SMILES: COC[C@H](NC(=O)c1ccc(N2CCSCC2=O)c(C)c1)c1nc2cc(Cl)ccc2[nH]1] N-[(1R)-1-(5-chloro-1H-benzimidazol-2-yl)-2-methoxy-ethyl]-3-methyl-4-(thiomorpholin-3-on-4-yl)-benzamide | Σ: 8.0% | $(M + H)^+$ = 459/461 (chlorine isotope) | 0.60 (silica gel, $CH_3COOC_2H_5$/ $C_2H_5OH$ 9:1 + 1% $NH_3$) |

Example 33

N-[(1S)-1-(5-chloro-1H-benzimidazol-2-yl)-ethyl]-4-(N-methyl-piperazin-1-yl)-3-trifluoromethyl-benzamide

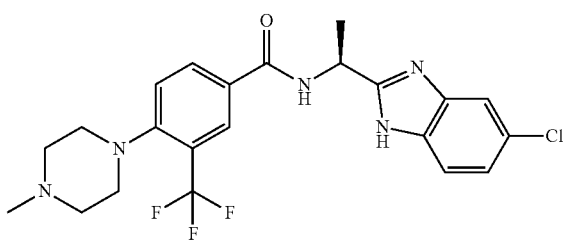 [SMILES: C[C@H](NC(=O)c1ccc(N2CCN(C)CC2)c(C(F)(F)F)c1)c1nc2cc(Cl)ccc2[nH]1]

170 mg (0.24 mmol) N-[(1S)-1-(5-chloro-1H-benzimidazol-2-yl)-ethyl]-4-(piperazin-1-yl)-3-trifluoromethyl-benzamide are suspended in 2 ml 1,2-dichloroethane and under a nitrogen atmosphere combined with 20 mg (0.67 mmol) paraformaldehyde and 76 mg (0.36 mmol) sodium triacetoxyborohydride. After the addition of 5 ml THF the reaction mixture is stirred for 6 hours at ambient temperature, then 100 mg (3.33 mmol) of paraformaldehyde and 100 mg (0.47 mmol) sodium triacetoxyborohydride are added and the mixture is stirred for a further 22 hours at ambient temperature. Then it is combined with sat. sodium hydrogen carbonate solution and extracted with ethyl acetate. The combined organic phases are dried over magnesium sulphate, evaporated down i. vac. and purified by chromatography on silica gel (eluting gradient: dichloromethane/(methanol/conc. ammonia solution 19:1) 100:0->92:8).

Yield: 70 mg (59%)

$C_{23}H_{25}ClF_3N_5O_2$ (495.94)

Mass spectrum: $(M+H)^+$=496/498 (chlorine isotope)

$R_f$ value: 0.25 (silica gel; dichloromethane/methanol=9:1+ 1% conc. ammonia solution)

Example 34

N-[(1S)-1-(5-chloro-1H-benzimidazol-2-yl)-3-methylsulphonyl-propyl]-3-methyl-4-(morpholin-3-on-4-yl)-benzamide

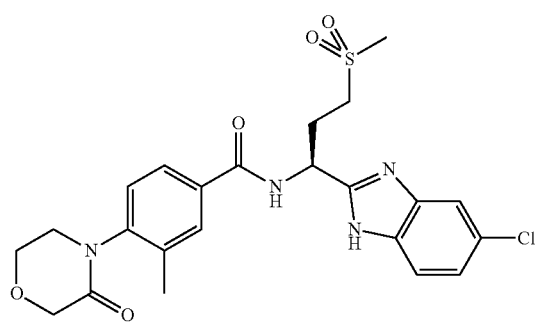 [SMILES: Cc1cc(C(=O)N[C@@H](CCS(C)(=O)=O)c2nc3cc(Cl)ccc3[nH]2)ccc1N1CCOCC1=O]

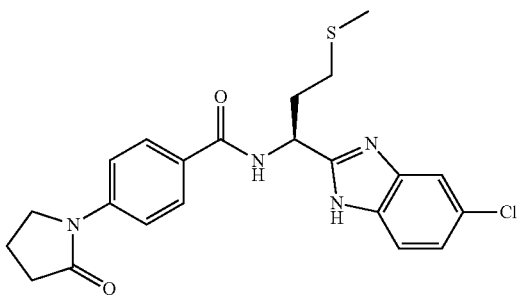 [SMILES: CSCC[C@H](NC(=O)c1ccc(N2CCCC2=O)cc1)c1nc2cc(Cl)ccc2[nH]1]

Prepared analogously to Example 27 from 4-(pyrrolidin-2-on-1-yl)-benzoic acid, (1S)-1-(5-chloro-1H-benzimidazol-2-yl)-3-methylsulphanyl-propylamine, PfTU and TEA in DMSO at ambient temperature and subsequent Boc cleaving with TFA analogously to Example 1g.

HPLC-MS results:

retention time: 3.69 min $C_{22}H_{23}ClN_4O_2S$ (442.97)

Mass spectrum: $(M+H)^+$=443/445 (chlorine isotope)

The following compound is prepared analogously:

| No. | structural formula / Name | mass peak(s) | retention time |
|---|---|---|---|
| 36 | <br>N-[1-(5-chloro-1H-benzimidazol-2-yl)-1-phenyl-methyl]-4-(pyrrolidin-2-on-1-yl)-benzamide | $(M + H)^+$ = 445/447 (chlorine isotope) | 3.80 min |

150 mg (0.32 mmol) N-[(1S)-1-(5-chloro-1H-benzimidazol-2-yl)-3-methylsulphanyl-prop-1-yl]-3-methyl-4-(morpholin-3-on-4-yl)-benzamide are dissolved in a mixture of 10 ml dichloromethane and 1 ml acetic acid at −15° C. and combined with 204 mg (0.89 mmol) 3-chloroperbenzoic acid. The mixture is then stirred for 30 minutes at −15 to −10° C., heated to ambient temperature and stirred for a further 16 hours. Then the reaction mixture is washed twice with 5% sodium hydrogen carbonate solution, dried over sodium sulphate, evaporated down i. vac. and purified by chromatography on silica gel (eluant: dichloromethane/ethanol 95:5).

Yield: 80 mg (50%)

$C_{23}H_{25}ClN_4O_5S$ (505.00)

Mass spectrum: $(M+H)^+$=505/507 (chlorine isotope)

$R_f$ value: 0.45 (silica gel; dichloromethane/ethanol=9:1)

Example 35

N-[(1S)-1-(5-chloro-1H-benzimidazol-2-yl)-3-methylsulphanyl-propyl]-4-(pyrrolidin-2-on-1-yl)-benzamide

Example 39

N-[(1S)-1-(5-chloro-1H-benzimidazol-2-yl)-ethyl]-3-methyl-4-([1,3]oxazepan-2-on-3-yl)-benzamide

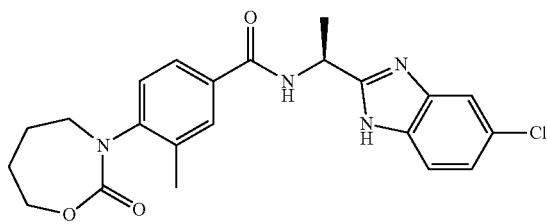 [SMILES: Cc1cc(C(=O)N[C@@H](C)c2nc3cc(Cl)ccc3[nH]2)ccc1N1CCCCOC1=O]

(a) methyl 4-isocyanato-3-methyl-benzoate 1.50 g (9.08 mmol) methyl 4-amino-3-methyl-benzoate are dissolved in 250 ml dioxane combined with 1.3 ml (10.7 mmol) trichloromethyl-chloroformate and refluxed for 5.5 hours with stirring. Then the mixture is evaporated down i. vac. and the residue is further reacted without any more purification.

Yield: 1.74 g (quantitative)
$C_{10}H_9NO_3$ (191.19)

(b) methyl 4-(N-[4-chlorobutoxycarbonyl]amino)-3-methyl-benzoate 1.74 g (9.08 mmol) 4 methyl-isocyanato-3-methyl-benzoate dissolved in 100 ml of toluene are combined with 1.07 ml (9.11 mmol) 85% m 4-chloro-butan-1-ol. The mixture is refluxed for 17 hours with stirring. After evaporation i. vac. the residue is purified by chromatography on silica gel (eluting gradient: petroleum ether/ethyl acetate 17:3->17:4).

Yield: 1.19 g (44%)
$C_{14}H_{18}ClNO_4$ (299.76)
Mass spectrum: (M−H)⁻=298/300 (chlorine isotope)
$R_f$ value: 0.45 (silica gel; petroleum ether/ethyl acetate=80:20)

(c) methyl 3-methyl-4-([1,3]oxazepan-2-on-3-yl)-benzoate 300 mg (1.00 mmol) methyl 4-(N-[4-chlorobutoxycarbonyl]-amino)-3-methyl-benzoate are dissolved in 10 ml DMF combined with 168 mg (1.50 mmol) potassium-tert.-butoxide and stirred for 3 hours at 60° C. The reaction mixture is mixed with water and extracted 3 times with ethyl acetate. The combined organic phases are dried over sodium sulphate and evaporated down i. vac. Then the residue is purified by chromatography on silica gel (eluant: petroleum ether/ethyl acetate 3:2).

Yield: 160 mg (61%)
$R_f$ value: 0.26 (silica gel; petroleum ether/ethyl acetate 3:2)

$C_{14}H_{17}NO_4$ (263.30)
Mass spectrum: (M+H)⁺=264

(d) 3-methyl-4-([1,3]oxazepan-2-on-3-yl)-benzoic acid 150 mg (0.57 mmol) methyl 3-methyl-4-([1,3]oxazepan-2-on-3-yl)-benzoate are suspended in 1 ml of ethanol and combined with 0.26 ml (0.87 mmol) 8% aqueous lithium hydroxide solution. The mixture is stirred for 3 hours at ambient temperature and then evaporated down i. vac. The aqueous residue is extracted twice with ethyl acetate, then acidified and extracted twice more with ethyl acetate. The combined organic phases are dried over sodium sulphate and evaporated down i. vac.

Yield: 122 mg (86%)
$C_{13}H_{15}NO_4$ (249.27)
Mass spectrum: (M+H)⁺=250
$R_f$ value: 0.14 (silica gel; dichloromethane/methanol=95:5)

(e) N-[(1S)-1-(5-chloro-1H-benzimidazol-2-yl)-ethyl]-3-methyl-4-([1,3]oxazepan-2-on-3-yl)-benzamide Prepared analogously to Example 1f from 3-methyl-4-([1,3]oxazepan-2-on-3-yl)-benzoic acid, (1S)-1-(5-chloro-1H-benzimidazol-2-yl)-ethylamine, TBTU and NMM in DMF, then acidifying with TFA and purification of the residue by chromatography (preparative HPLC).

Yield: 54%
$C_{22}H_{23}ClN_4O_3 \cdot 2CF_3COOH$ (654.96/426.90)
Mass spectrum: (M+H)⁺=427/429 (chlorine isotope)
$R_t$: 2.42 min The following compounds were prepared analogously:

| No. | structural formula / Name | Yield | mass peak(s) | $R_t$ |
|---|---|---|---|---|
| 43 | N-[(1R)-1-(5-chloro-1H-benzimidazol-2-yl)-2-methoxy-ethyl]-3-methyl-4-([1,3]oxazepan-2-on-3-yl)-benzamide | Σ: 12% | (M − H)⁻ = 455/457 (chlorine isotope) | 2.43 min |
| 51 | N-[(1S)-1-(5-chloro-1H-benzimidazol-2-yl)-ethyl]-3-methyl-4-(oxazolidin-2-on-3-yl)-benzamide | Σ: 2.6% | (M − H)⁻ = 397/399 (chlorine isotope) | 3.70 min |

| No. | structural formula Name | Yield | mass peak(s) | $R_f$ |
|---|---|---|---|---|
| 57 | N-[(1S)-1-(5-chloro-1H-benzimidazol-2-yl)-ethyl]-3-methyl-4-([1,3]-oxazinan-2-on-3-yl)-benzamide | Σ: 3.4% | $(M + H)^+ = 413/415$ (chlorine isotope) | 3.63 min |
| 58 | N-[(1R)-1-(5-chloro-1H-benzimidazol-2-yl)-2-methoxy-ethyl]-3-methyl-4-([1,3]-oxazinan-2-on-3-yl)-benzamide | Σ: 2.7% | $(M + H)^+ = 443/445$ (chlorine isotope) | 3.66 min |
| 68 | N-[(1R)-1-(5-chloro-1H-benzimidazol-2-yl)-2-methoxy-ethyl]-4-([1,3]oxazepan-2-on-3-yl)-3-trifluoromethyl-benzamide | Σ: 0.32% | $(M + H)^+ = 511/513$ (chlorine isotope) | 4.21 min |

Example 41

N-[(1S)-1-(5-chloro-1H-benzimidazol-2-yl)-3-methylsulphanyl-propyl]-4-(morpholin-3-on-4-yl)-3-nitro-benzamide

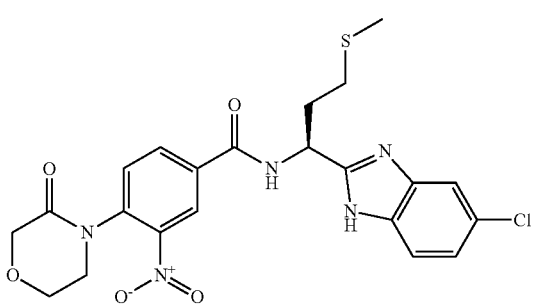 [SMILES: CSCC[C@H](NC(=O)c1ccc(N2CCOCC2=O)c([N+](=O)[O-])c1)c1nc2cc(Cl)ccc2[nH]1]

(a) methyl 4-(morpholin-3-on-4-yl)-3-nitro-benzoate 1.00 g (3.85 mmol) methyl 4-bromo-3-nitro-benzoate are dissolved in 6 ml dioxane with 389 mg (3.85 mmol) morpholin-3-one under a nitrogen atmosphere and 36.6 mg (40 μmol) tris-(dibenzylideneacetone)-dipalladium (0), 67.1 mg (116 μmol) xantphos and 1.75 g (5.38 mmol) caesium carbonate are added. Under a nitrogen atmosphere and with stirring, the reaction mixture is heated to 95° C. for 16 hours. Then it is filtered, the solution is evaporated down i. vac. and evaporated with ether. The residue is further reacted without any more purification. Yield: 1.31 g (quantitative)

$C_{12}H_{12}N_2O_6$ (280.24)

Mass spectrum: $(M+H)^+=281$ $R_f$ value: 0.47 (Reversed phase 8; methanol/5% sodium chloride solution=6:4)

(b) 4-(2-carboxymethoxy-ethylamino)-3-nitro-benzoic acid 400 mg (1.43 mmol) methyl 4-(morpholin-3-on-4-yl)-3-nitro-benzoate are dissolved in 15 ml of methanol and combined with 4.5 ml (4.5 mmol) 1-molar lithium hydroxide solution. The mixture is stirred for 2 hours at ambient temperature. Then it is evaporated down i. vac., the residue is diluted with water, cooled in the ice bath and acidified with 2-molar hydrochloric acid. After 10 minutes cooling in the ice bath the precipitate formed is filtered off, washed with water until neutral and dried at 50° C. in the drying cupboard.

Yield: 290 mg (72%)
$C_{11}H_{12}N_2O_7$ (284.23)
Mass spectrum: M+=284
$R_f$ value: 0.59 (Reversed phase 8; methanol/5% sodium chloride solution=6:4)

(c) 4-(morpholin-3-on-4-yl)-3-nitro-benzoic acid-chloride 290 mg (1.02 mmol) 4-(2-carboxymethoxy-ethylamino)-3-nitro-benzoic acid in 100 ml dichloromethane are combined with 0.186 ml (2.55 mmol) thionyl chloride and 2 drops of DMF and refluxed for one day. After evaporation of the solution i. vac. it is evaporated with toluene and the residue is further reacted without any more purification.

Yield: 290 mg (quant.)
$C_{11}H_9ClN_2O_5$ (284.66)

(d) N-[(1S)-1-(5-chloro-1H-benzimidazol-2-yl)-3-methylsulphanyl-propyl]-4-(morpholin-3-on-4-yl)-3-nitro-benzamide 237 mg (0.93 mmol) of (1S)-1-(5-chloro-1H-benzimidazol-2-yl)-3-methylsulphanyl-propylamine are dissolved with 0.257 ml TEA in 10 ml THF and a solution of 290 mg (1.02 mmol) 4-(morpholin-3-on-4-yl)-3-nitro-benzoic acid chloride in 10 ml THF is added dropwise. The reaction mixture is stirred for 16 hours at ambient temperature and then evaporated down i. vac. The residue is purified by chromatography on silica gel (eluting gradient: dichloromethane/ethanol 100:0->95:5).

Yield: 34%
$C_{22}H_{22}ClN_5O_5S$ (503.97)
Mass spectrum: (M-H)−=502/504 (chlorine isotope)
$R_f$ value: 0.46 (silica gel; dichloromethane/ethanol=9:1)

Example 42

3-chloro-N-[(1S)-1-(5-chloro-1H-benzimidazol-2-yl)-ethyl]-4-(tetrahydro-pyrimidin-2-on-1-yl)-benzamide

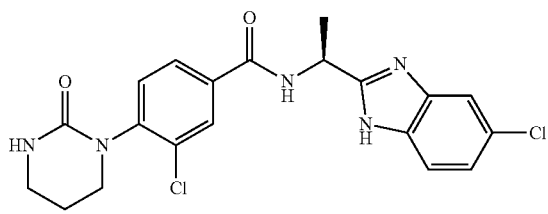 [SMILES: C[C@H](NC(=O)c1ccc(N2CCCNC2=O)c(Cl)c1)c1nc2cc(Cl)ccc2[nH]1]

(a) 4-(3-Boc-amino-propyl-amino)-3-chloro-benzonitrile 3.49 g (20 mmol) 3-Boc-amino-propylamine in 5 ml DMF are combined with 2.75 ml (25 mmol) NMM. After the addition of 3.11 g (20 mmol) 3-chloro-4-fluoro-benzonitrile the mixture is stirred for 3.5 hours at ambient temperature under a nitrogen atmosphere, heated to 105° C. for 20 minutes and extracted with ethyl acetate. The combined organic phases are washed with water and sat. sodium chloride solution, dried over magnesium sulphate and evaporated down i. vac. The residue is further reacted without any more purification.

Yield: 5.50 g (89%)
$C_{15}H_{20}N_3O_2$ (309.80)
Mass spectrum: (M+H)+=310/312 (chlorine isotope)
$R_f$ value: 0.40 (silica gel; petroleum ether/ethyl acetate=2:1)

(b) 4-(3-amino-propylamino)-3-chloro-benzonitrile 4.50 g (14.5 mmol) 4-(3-Boc-amino-propylamino)-3-chloro-benzonitrile are dissolved in 50 ml dioxane and combined with 200 ml 6-molar hydrochloric acid. The mixture is stirred for 2 hours at ambient temperature, then washed with ether and the aqueous phase is poured into 125 ml ice-cooled conc. ammonia solution. Then the mixture is extracted with ethyl acetate, the combined organic phases are washed with water and sat. sodium chloride solution, dried over magnesium sulphate and evaporated down i. vac. The residue is further reacted without any more purification.

Yield: 1.40 g (46%)
$C_{10}H_{12}ClN_3$ (209.68)
Mass spectrum: (M+H)+=210/212 (chlorine isotope)
$R_f$ value: 0.30 (silica gel; dichloromethane/methanol=9:1+1% conc. ammonia solution)

(c) 3-chloro-4-(tetrahydro-pyrimidin-2-on-1-yl)-benzonitrile

A solution of 349 mg (2.15 mmol) N,N'-carbonyl-diimidazole in 3 ml NMP is combined with 450 mg (2.15 mmol) 4-(3-amino-propylamino)-3-chloro-benzonitrile at ambient temperature with stirring and once fully dissolved heated for one hour to 145° C. and for 1.5 hours to 155° C. The reaction mixture is washed with water and extracted with ethyl acetate. The combined organic phases are washed with water and sat. sodium chloride solution, dried over magnesium sulphate and evaporated down i. vac. Then the residue is purified by chromatography on silica gel (eluting gradient: ethyl acetate/(methanol/conc. ammonia solution 19:1)=100:0->95:5).

Yield: 260 mg (51%)
$R_f$ value: 0.40 (silica gel; ethyl acetate/ethanol 9:1+1% conc. ammonia solution)
$C_{11}H_{10}ClN_3O$ (235.68)
Mass spectrum: (M+H)+=236/238 (chlorine isotope)

(d) 3-chloro-4-(tetrahydro-pyrimidin-2-on-1-yl)-benzoic acid 350 mg (1.49 mmol) 3-chloro-4-(tetrahydro-pyrimidin-2-on-1-yl)-benzonitrile are suspended in 5 ml of ethanol and combined with 2.0 ml of 10-molar aqueous sodium hydroxide solution. The mixture is stirred for one hour at 100° C. and then evaporated down i. vac. The aqueous residue is combined with ice, acidified with acetic acid and extracted with ethyl acetate. The combined organic phases are washed with water and sat. sodium chloride solution, dried over magnesium sulphate and evaporated down i. vac. The aqueous phase is acidified with 6-molar hydrochloric acid, extracted 5 times with ethyl acetate, the combined organic phases are washed with sat. sodium chloride solution, dried over magnesium sulphate and evaporated down i. vac.

Yield: 340 mg (90%)
$C_{11}H_{11}ClN_2O_3$ (254.68)
Mass spectrum: $(M+H)^+=255/257$ (chlorine isotope)
$R_f$ value: 0.35 (silica gel; dichloromethane/methanol=9:1+1% acetic acid)

(e) 3-chloro-N-[(1S)-1-(5-chloro-1H-benzimidazol-2-yl)-ethyl]-4-(tetrahydro-pyrimidin-2-on-1-yl)-benzamide Prepared analogously to Example 1f from 3-chloro-4-(tetrahydro-pyrimidin-2-on-1-yl)-benzoic acid, (1S)-1-(5-chloro-1H-benzimidazol-2-yl)-ethylamine, TBTU and NMM in DMF, then pouring into ice water, adding conc. ammonia solution, filtering, washing with water and purifying by chromatography on silica gel (eluting gradient ethyl acetate/(methanol/conc. ammonia solution 19:1)=98:2->90:10) with subsequent filtration through activated charcoal, trituration with ether and drying in the drying pistol at 70° C.
Yield: 32%
$C_{20}H_{19}Cl_2N_5O_2$ (432.31)
Mass spectrum: $(M+H)^+=432/434/436$ (chlorine isotope)
$R_f$ value: 0.40 (silica gel; dichloromethane/methanol=9:1+1% acetic acid)
The following compound is prepared analogously:

(a) methyl 3-chloro-4-(5-chloro-pentanoyl-amino)-benzoate

A solution of 696 µl (0.84 g, 5.39 mmol) 5-chloro-pentanoylchloride in 10 ml THF is slowly added dropwise to 1.00 g (5.39 mmol) methyl 4-amino-3-chloro-benzoate in 20 ml THF with 1 ml TEA with stirring in the ice bath. After stirring for 16 hours at ambient temperature, for 3 hours at 50° C. and for 3 hours at reflux temperature the mixture is poured into water and extracted with ethyl acetate. After the organic phases have been dried over sodium sulphate the mixture is evaporated down i. vac. and the residue remaining is purified by chromatography on silica gel (eluant: petroleum ether/ethyl acetate 85:15).
Yield: 300 mg (14.6%) 80% product
$C_{13}H_{15}Cl_2NO_3$ (304.18)
Mass spectrum: $(M+H)^+=304/306/308$ (chlorine isotope)
$R_t$ value: 3.29 min (b) methyl 3-chloro-4-(piperidin-2-on-1-yl)-benzoate 300 mg (0.79 mmol) of the product obtained in Example 46a is dissolved in 10 ml DMF and combined with 180 mg (1.60 mmol) potassium-tert.-butoxide and heated to 60° C. for 3 hours. Then the reaction mixture is poured into water

| No. | structural formula Name | Yield | mass peak(s) | $R_f$ value or $R_t$ |
|---|---|---|---|---|
| 114 | ![structure] 3-chloro-N-[(1R)-1-(5-chloro-1H-benzimidazol-2-yl)-2-methoxy-ethyl]-4-(tetrahydro-pyrimidin-2-on-1-yl)-benzamide | Σ: 5.4% | $(M + H)^+ =$ 462/464/466 (chlorine isotope) | 0.52 (ethyl acetate/ethanol = 8:2) |

Example 46

3-chloro-N-[(1R)-1-(5-chloro-1H-benzimidazol-2-yl)-2-methoxy-ethyl]-4-(piperidin-2-on-1-yl)-benzamide

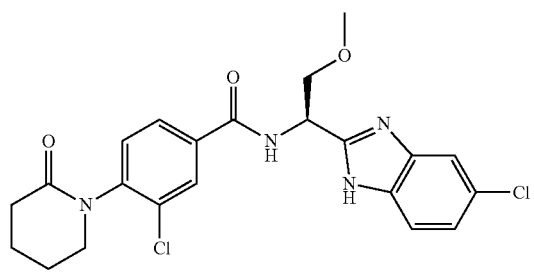 [SMILES: COC[C@H](NC(=O)c1ccc(N2CCCCC2=O)c(Cl)c1)c1nc2cc(Cl)ccc2[nH]1]

and extracted with ethyl acetate. The combined organic phases are dried over sodium sulphate, evaporated down i. vac. and the residue obtained is purified by chromatography on silica gel (eluant: dichloromethane/isopropanol 98:2).
Yield: 159 mg (75%)
$C_{13}H_{14}ClNO_3$ (267.71)
Mass spectrum: $(M+H)^+=268/270$ (chlorine isotope)
$R_f$ value: 0.18 (silica gel; dichloromethane/isopropanol=49:1)

(c) 3-chloro-4-(piperidin-2-on-1-yl)-benzoic acid

Prepared analogously to Example 39d from methyl 3-chloro-4-(piperidin-2-on-1-yl)-benzoate and 8% lithium hydroxide solution in ethanol.
Yield: 36%
$C_{12}H_{12}ClNO_3$ (247.30)
Mass spectrum: $(M+H)^+=252/254$ (chlorine isotope)
$R_f$ value: 0.27 (silica gel; dichloromethane/ethanol=9:1)

(d) 3-chloro-N-[(1R)-1-(5-chloro-1H-benzimidazol-2-yl)-2-methoxy-ethyl]-4-(piperidin-2-on-1-yl)-benzamide Prepared analogously to Example 1f from 3-chloro-4-(piperidin-2-on-1-yl)-benzoic acid, TBTU, NMM and (1R)-1-(5-chloro-1H-benzimidazol-2-yl)-2-methoxy-ethylamine in DMF and subsequent purification by chromatography on silica gel (eluting gradient: ethyl acetate/ethanol 95:5->90:10).
Yield: 70%
$C_{22}H_{22}Cl_2N_4O_3$ (461.35)
Mass spectrum: $(M-H)^-=459/461/463$ (chlorine isotope)
$R_f$-value: 0.19 (silica gel; dichloromethane/ethanol=19:1)
The following compound is prepared analogously:

| No. | structural formula Name | Yield | mass peak(s) | $R_f$-value or $R_t$ |
|---|---|---|---|---|
| 59 | N-[(1R)-1-(5-chloro-1H-benzimidazol-2-yl)-2-methoxy-ethyl]-4-(piperidin-2-on-1-yl)-3-trifluoromethyl-benzamide | Σ: 1.3% | $(M + H)^+$ = 495/497 (chlorine isotope) | 2.51 min |

Yield: 4.76 g (48%) mixture of the two regioisomers
$C_{14}H_{20}BrN_3O_4$ (374.24)
Mass spectrum: $(M+H)^+=374/376$ (bromine isotope)

(b) (1R)-N-Boc-1-(5-bromo-1H-benzimidazol-2-yl)-2-hydroxy-ethylamine 3.00 g (8.02 mmol) of the mixture obtained in 47a are dissolved in 30 ml acetic acid and stirred for 2 hours at 50° C. The reaction mixture is added dropwise to a 10% sodium hydroxide solution and extracted 3 times with ethyl acetate. The combined organic phases are dried over magnesium sulphate and evaporated down i. vac. and the residue is recrystallised from methanol.

Yield: 1.96 g (69%)
$C_{14}H_{18}BrN_3O_3$ (356.22)
$R_f$-value: 0.59 (silica gel; petroleum ether/ethyl acetate=1:1)

(c) (1R)-1-(5-bromo-1H-benzimidazol-2-yl)-2-hydroxy-ethylamine 2.00 g (5.62 mmol) (1R)-N-Boc-1-(5-bromo-1H-benzimidazol-2-yl)-2-hydroxy-ethylamine in 40 ml of ethyl acetate are combined with 8.0 ml 4-molar hydrochloric acid in dioxane while cooling in the ice bath and stirred for 16 hours at ambient temperature. The reaction mixture is evaporated down and the resulting precipitate is filtered off.
Yield: 1.11 g (67%)
$C_9H_{10}BrN_3O \cdot HCl$ (292.57/256.10)
Mass spectrum: $(M+H)^+=256/258$ (bromine isotope)

(d) N-[(1R)-1-(5-bromo-1H-benzimidazol-2-yl)-2-hydroxy-ethyl]-3-methyl-4-(morpholin-3-on-4-yl)-benzamide Prepared analogously to Example 1f from 3-methyl-4-(morpholin-3-on-4-yl)-benzoic acid, (1R)-1-(5-bromo-1H-benzimidazol-2-yl)-2-hydroxy-ethylamine, TBTU and NMM in DMF with subsequent purification by preparative HPLC.
Yield: 52%
$C_{21}H_{21}BrN_4O_4 \cdot CF_3COOH$ (587.35/473.32)
Mass spectrum: $(M+H)^+=473/475$ (bromine isotope)
$R_f$-value: 0.33 (silica gel; dichloromethane/methanol=19:1)

Example 47

N-[(1R)-1-(5-bromo-1H-benzimidazol-2-yl)-2-hydroxy-ethyl]-3-methyl-4-(morpholin-3-on-4-yl)-benzamide

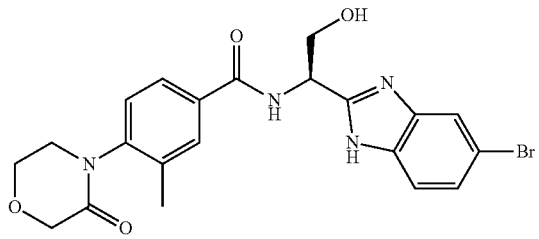 [SMILES: Cc1cc(C(=O)N[C@@H](CO)c2nc3cc(Br)ccc3[nH]2)ccc1N1CCOCC1=O]

(a) N'-(2-amino-4-bromo-phenyl)-N-Boc-(S)-serinamide and N'-(2-amino-5-bromo-phenyl)-N-Boc-(S)-serinamide 5.49 g (26.7 mmol) (S)-N-Boc-serine are dissolved with 5.00 g (26.7 mmol) 4-bromo-1,2-phenylenediamine in 125 ml THF and a solution of 5.52 g (26.7 mmol) N,N'-dicyclohexylcarbodiimide in 20 ml THF is added dropwise while cooling with ice. The reaction mixture is stirred for 16 hours at ambient temperature. After evaporation i. vac. the residue is purified by chromatography on silica gel (eluant: dichloromethane/methanol 98:2).

The following compounds were prepared analogously:

| No. | structural formula / Name | Yield | mass peak(s) | $R_f$ value or $R_t$ |
|---|---|---|---|---|
| 53 | N-[(1R,2S)-1-(5-chloro-1H-benzimidazol-2-yl)-2-methoxy-propyl]-3-methyl-4-(morpholin-3-on-4-yl)-benzamide | Σ: 6.6% | $(M + H)^+ =$ 457/459 (chlorine isotope) | 0.48 (silica gel, $CH_2Cl_2/C_2H_5OH$ 9:1) |
| 62 | 4-(azepan-2-on-1-yl)-N-[(1S)-1-(5-chloro-6-fluoro-1H-benzimidazol-2-yl)-ethyl]-3-methyl-benzamide | Σ: 34% | $(M - H)^- =$ 441/443 (chlorine isotope) | 0.40 (aluminium oxide, $CH_2Cl_2/C_2H_5OH$ 19:1) |
| 67 | N-[(1S)-1-(5-chloro-1H-benzimidazol-2-yl)-butyl]-3-methyl-4-(morpholin-3-on-4-yl)-benzamide | Σ: 38% | $(M + H)^+ =$ 441/443 (chlorine isotope) | 0.50 (silica gel, $CH_2Cl_2/C_2H_5OH$ 9:1) |
| 78 | N-[1-(5-chloro-1H-benzimidazol-2-yl)-1-(thiophen-3-yl)-methyl]-3-methyl-4-(morpholin-3-on-4-yl)-benzamide | Σ: 38% | $(M + H)^+ =$ 481/483 (chlorine isotope) | 0.51 (silica gel, $CH_2Cl_2/C_2H_5OH$ 9:1) |

| No. | structural formula / Name | Yield | mass peak(s) | $R_f$-value or $R_t$ |
|---|---|---|---|---|
| 79 | N-[(1R)-1-(5-chloro-1H-benzimidazol-2-yl)-2-methylsulphanyl-ethyl]-3-methyl-4-(morpholin-3-on-4-yl)-benzamide | Σ: 10.6% | $(M + H)^+$ = 459/461 (chlorine isotope) | 0.50 (silica gel, $CH_2Cl_2/C_2H_5OH$ 9:1) |
| 99 | N-[1-(5-chloro-1H-benzimidazol-2-yl)-1-(thiophen-2-yl)-methyl]-3-methyl-4-(morpholin-3-on-4-yl)-benzamide | Σ: 18% | $(M + H)^+$ = 481/483 (chlorine isotope) | 2.43 min |
| 101 | N-[(1R)-1-(5-bromo-1H-benzimidazol-2-yl)-2-hydroxy-ethyl]-3-methyl-4-([1,3]oxazepan-2-on-3-yl)-benzamide | Σ: 2.9% | $(M + H)^+$ = 487/489 (bromine isotope) | 2.31 min |

Example 48

N-[(1S)-1-(5-chloro-1H-benzimidazol-2-yl)-ethyl]-4-(1,1-dioxo-isothiazolidin-2-yl)-3-methyl-benzamide

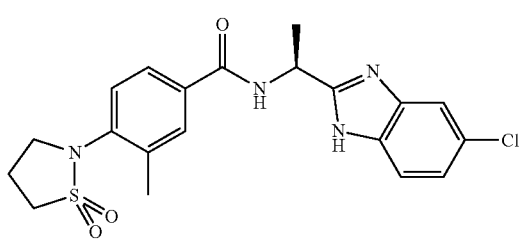 [SMILES: Cc1cc(C(=O)N[C@@H](C)c2nc3cc(Cl)ccc3[nH]2)ccc1N1CCCS1(=O)=O]

(a) methyl 4-(3-chloro-propyl-sulphonyl-amino)-3-methyl-benzoate 100 mg (0.61 mmol) methyl 4-amino-3-methyl-benzoate dissolved in 3 ml of pyridine are combined with 82 μl (0.67 mmol) 3-chloropropanesulphonic acid chloride and stirred for 16 hours at ambient temperature. The reaction solution is combined with water and ethyl acetate and then the aqueous phase is again extracted with ethyl acetate. The combined organic phases are dried over sodium sulphate and evaporated down i. vac. The residue is further reacted without any more purification.

Yield: 170 mg (92%)
$C_{12}H_{16}ClNO_4S$ (305.78)
Mass spectrum: $(M+H)^+$=306/308 (chlorine isotope)
$R_f$ value: 0.10 (silica gel; petroleum ether/ethyl acetate=8:2)

(b) methyl 4-(1,1-dioxo-isothiazolidin-2-yl)-3-methyl-benzoate 370 mg (0.85 mmol) 70% methyl 4-(3-chloropropane-sulphonylamino)-3-methyl-benzoate dissolved in 26 ml DMF are combined with 275 mg (2.45 mmol) potassium-tert.-butoxide and stirred for 16 hours at ambient temperature. The reaction mixture is combined with water and extracted with ethyl acetate. The combined organic phases are dried over sodium sulphate, evaporated down i. vac. and the residue is purified by chromatography on silica gel (eluant: dichloromethane/isopropanol 98:2).

Yield: 177 mg (47%)
$C_{12}H_{15}NO_4S$ (269.32)
Mass spectrum: $(M+H)^+=270$
$R_f$ value: 0.10 (silica gel; petroleum ether/ethyl acetate=7:3)

(c) 4-(1,1-dioxo-isothiazolidin-2-yl)-3-methyl-benzoic acid 170 mg (0.63 mmol) methyl 4-(1,1-dioxo-isothiazolidin-2-yl)-3-methyl-benzoate are stirred in 2 ml of ethanol at ambient temperature for 3 hours with 0.6 ml of 2-molar sodium hydroxide solution. Then the reaction solution is evaporated down i. vac., combined with water and 0.6 ml 2-molar hydrochloric acid and extracted with ethyl acetate. The combined organic phases are dried over sodium sulphate, evaporated down i. vac. and the residue is further reacted without any more purification.

Yield: 148 mg (92%)
$C_{11}H_{13}NO_4S$ (255.30)
Mass spectrum: $(M-H)^-=254$
retention time: 2.23 min

(d) N-[(1S)-1-(5-chloro-1H-benzimidazol-2-yl)-ethyl]-4-(1,1-dioxo-isothiazolidin-2-yl)-3-methyl-benzamide Prepared analogously to Example 1f from 4-(1,1-dioxo-isothiazolidin-2-yl)-3-methyl-benzoic acid, (1S)-1-(5-chloro-1H-benzimidazol-2-yl)-ethylamine, TBTU and NMM in DMF with subsequent extraction with ethyl acetate, drying over magnesium sulphate, activated charcoal and silica gel followed by purification on silica gel (eluant: dichloromethane/isopropanol 95:5).

Yield: 37%
$C_{20}H_{21}ClN_4O_3S$ (432.93)
Mass spectrum: $(M+H)^+=433/435$ (chlorine isotope)
$R_f$ value: 0.32 (silica gel; dichloromethane/isopropanol=19:1)

The following compounds were prepared analogously:

| No. | structural formula / Name | Yield | mass peak(s) | $R_f$ value or $R_t$ |
|---|---|---|---|---|
| 60 | N-[(1R)-1-(5-chloro-1H-benzimidazol-2-yl)-2-methoxy-ethyl]-4-(1,1-dioxo-[1,2]thiazinan-2-yl)-3-methyl-benzamide | Σ: 18% | $(M + H)^+ =$ 477/479 (chlorine isotope) | 2.46 min |
| 71 | N-[(1R)-1-(5-chloro-1H-benzimidazol-2-yl)-2-methoxy-ethyl]-4-(1,1-dioxo-[1,2,6]thiadiazinan-2-yl)-3-methyl-benzamide | Σ: 20% | $(M + H)^+ =$ 478/480 (chlorine isotope) | 2.58 min |
| 72 | N-[(1S)-1-(5-chloro-1H-benzimidazol-2-yl)-ethyl]-4-(1,1-dioxo-[1,2,6]thiadiazinan-2-yl)-3-methyl-benzamide | Σ: 19% | $(M + H)^+ =$ 448/450 (chlorine isotope) | 2.41 min |

-continued

| No. | structural formula / Name | Yield | mass peak(s) | $R_f$ value or $R_t$ |
|---|---|---|---|---|
| 100 | 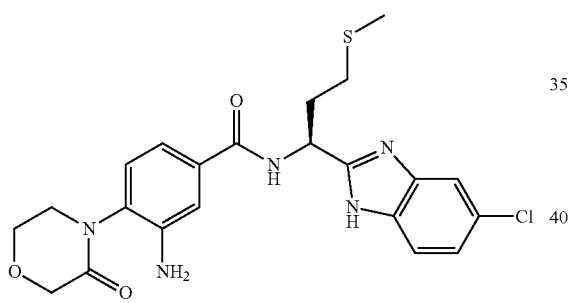 N-[(1R)-1-(5-bromo-1H-benzimidazol-2-yl)-2-hydroxy-ethyl]-4-(1,1-dioxo-[1,2]thiazinan-2-yl)-3-methyl-benzamide | Σ: 2.5% | $(M + H)^+ =$ 507/509 (bromine isotope) | 2.38 min |

Example 54

3-amino-N-[(1S)-1-(5-chloro-1H-benzimidazol-2-yl)-3-methylsulphanyl-propyl]-4-(morpholin-3-on-4-yl)-benzamide 65 mg (0.13 mmol) N-[(1S)-1-(5-chloro-1H-benzimidazol-2-yl)-3-methylsulphanyl-propyl]-4-(morpholin-3-on-4-yl)-3-nitro-benzamide dissolved in 2 ml of ethyl acetate are combined with 143 mg (0.63 mmol) tin (II)chloride-dihydrate and 130 mg (1.55 mmol) sodium hydrogen carbonate and refluxed for 2 hours. The reaction solution is combined with ice water, stirred for 10 minutes and then the precipitate formed is filtered off. After drying for 3 days the residue is purified by chromatography on silica gel (eluting gradient: dichloromethane/ethanol 100:0->91:9).

Yield: 5 mg (8.2%)

$C_{22}H_{24}ClN_5O_3S$ (473.99)

Mass spectrum: $(M+H)^+$=474/476 (chlorine isotope)

$R_f$ value: 0.48 (silica gel; dichloromethane/ethanol=9:1)

Example 61

N-[(1S)-1-(5-chloro-1H-benzimidazol-2-yl)-ethyl]-3-methyl-4-(5,6-didehydro-azepan-2-on-1-yl)-benzamide

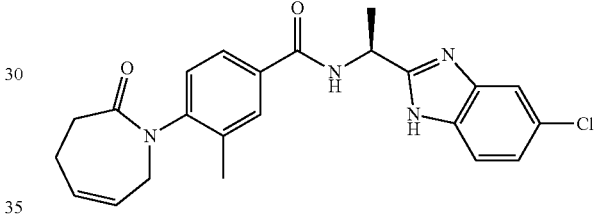

(a) methyl 3-methyl-4-(pent-4-en-1-oyl-amino)-benzoate

Prepared analogously to Example 46a from methyl 4-amino-3-methyl-benzoate and 4-pentene-1-acid-chloride in THF with TEA.

Yield: 46%

$C_{14}H_{17}NO_3$ (247.30)

Mass spectrum: $(M+H)^+$=248

$R_t$ value: 2.88 min (b) methyl 4-(allyl-pent-4-en-1-oyl-amino)-3-methyl-benzoate 1.00 g (4.04 mmol) methyl 3-methyl-4-(pent-4-en-1-oyl-amino)-benzoate dissolved in 5 ml DMF are combined with 500 mg (4.37 mmol) potassium-tert.-butoxide and at 40° C. 350 µl (489 mg, 4.04 mmol) allylbromide are slowly added with stirring. Then the mixture is heated to 70° C. for 3 hours. Then the reaction mixture is poured into water and extracted with ethyl acetate. The combined organic phases are dried over sodium sulphate, evaporated down i. vac., the residue is applied to silica gel and purified by chromatography on silica gel (eluant: petroleum ether/ethyl acetate 9:1).

Yield: 58%

$C_{17}H_{21}NO_3$ (287.36)

Mass spectrum: $(M+H)^+$=288

$R_f$ value: 0.46 (petroleum ether/ethyl acetate=9:1)

(c) methyl 4-(4,5-didehydro-azepan-2-on-1-yl)-3-methyl-benzoate 150 mg (0.52 mmol) methyl 4-(allyl-pent-4-en-1-oyl-amino)-3-methyl-benzoate are dissolved in 110 ml degassed dichloromethane and rinsed for 30 minutes with argon. Then 88 mg (104 µmol) benzylidene-[1,3-bis(2,4,6-trimethylphenyl)-2-imidazolidinylidene]-dichloro-(tricyclohexylphosphine)-ruthenium (2nd generation Grubbs Catalyst) are added and the mixture is refluxed for 4.5 hours. Then it is evaporated down i. vac., the residue is applied to silica gel and purified by chromatography on silica gel (eluant: petroleum ether/ethyl acetate 3:2).

Yield: 83 mg (61%)
$R_f$-value: 0.22 (silica gel, petroleum ether/ethyl acetate 3:2)
$C_{15}H_{17}NO_3$ (259.31)
Mass spectrum: $(M+H)^+=260$

(d) 4-(4,5-didehydro-azepan-2-on-1-yl)-3-methyl-benzoic acid

Prepared analogously to Example 39d from methyl 4-(4,5-didehydro-azepan-2-on-1-yl)-3-methyl-benzoate and 8% lithium hydroxide solution in ethanol.

Yield: 51%
$R_f$-value: 0.05 (silica gel; dichloromethane/methanol=19:1)
$C_{14}H_{15}NO_3$ (245.28)
Mass spectrum: $(M+H)^+=246$

(e) N-[(1S)-1-(5-chloro-1H-benzimidazol-2-yl)-ethyl]-4-(4,5-didehydro-azepan-2-on-1-yl)-3-methyl-benzamide Prepared analogously to Example 1f from 4-(4,5-didehydro-azepan-2-on-1-yl)-3-methyl-benzoic acid, TBTU, NMM and (1S)-1-(5-chloro-1H-benzimidazol-2-yl)-ethylamine in DMF and subsequent purification by preparative HPLC.

Yield: 32%
$R_f$-value: 0.44 (silica gel; dichloromethane/methanol=19:1)
$C_{23}H_{23}ClN_4O_2 \cdot CF_3COOH$ (536.94/422.91)
Mass spectrum: $(M+H)^+=423/425$ (chlorine isotope)

Example 63

N-[(1S)-1-(5-chloro-1H-benzimidazol-2-yl)-ethyl]-4-(1,3-dioxo-thiomorpholin-4-yl)-3-methyl-benzamide

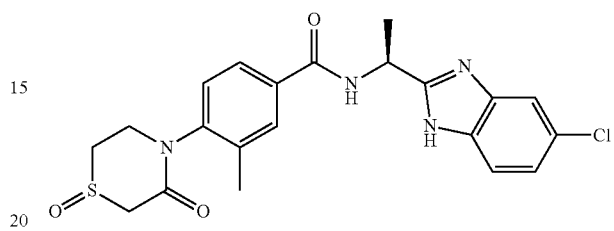

204 mg (0.48 mmol) N-[(1S)-1-(5-chloro-1H-benzimidazol-2-yl)-ethyl]-3-methyl-4-(thiomorpholin-3-on-4-yl)-benzamide are dissolved in a mixture of 12 ml dichloromethane and 1.2 ml acetic acid at −15° C. and combined with 110 mg (0.48 mmol) 3-chloroperbenzoic acid. The mixture is then stirred for one hour at −15 to −10° C., heated to ambient temperature and stirred for a further 3 hours. Then the reaction mixture is combined with semi-concentrated sodium hydrogen carbonate solution and extracted with a solvent mixture dichloromethane/methanol 19:1. The combined organic phases are washed with water, dried over magnesium sulphate, evaporated down i. vac. and purified by chromatography on silica gel (eluting gradient: ethyl acetate/(ethanol/conc. ammonia solution 19:1)=1:0->4:1).

Yield: 100 mg (47%)
$C_{21}H_{21}ClN_4O_3S$ (444.94)
Mass spectrum: $(M+H)^+=445/447$ (chlorine isotope)
$R_f$ value: 0.15 (silica gel; ethyl acetate/ethanol=4:1+1% conc. ammonia solution)

The following compound is prepared analogously:

| No. | structural formula / Name | Yield | mass peak(s) | $R_f$-value |
|---|---|---|---|---|
| 64 | N-[(1S)-1-(5-chloro-1H-benzimidazol-2-yl)-ethyl]-3-methyl-4-(1,1,3-trioxo-thiomorpholin-4-yl)-benzamide | Σ: 14% | $(M+H)^+ = $ 461/463 (chlorine isotope) | 0.70 (silica gel, $CH_3COOC_2H_5/C_2H_5OH$ 4:1 + 1% conc. ammonia solution) |

Example 69

N-[(1S)-1-(5-chloro-1H-benzimidazol-2-yl)-ethyl]-3-methoxy-4-(piperidin-2-on-1-yl)-benzamide

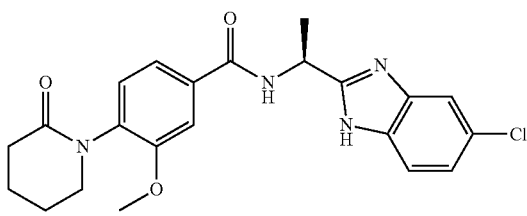 [SMILES: COc1cc(C(=O)N[C@@H](C)c2nc3cc(Cl)ccc3[nH]2)ccc1N1CCCCC1=O]

(a) methyl 4-(5-chloro-pentanoyl-amino)-3-methoxy-benzoate

Prepared analogously to Example 6a from methyl 4-amino-3-methoxy-benzoate and 5-chloro-pentanoic acid chloride in THF with TEA.
Yield: 99%
$C_{14}H_{18}ClNO_4$ (299.76)
Mass spectrum: $(M+H)^+=300/302$ (chlorine isotope)
$R_t$ value: 3.14 min (b) methyl 3-methoxy-4-(piperidin-2-on-1-yl)-benzoate 2.25 g (7.51 mmol) methyl 4-(5-chloro-pentanoyl-amino)-3-methoxy-benzoate dissolved in 60 ml DMF are combined with 1.26 g (11.2 mmol) potassium-tert.-butoxide and stirred for 2.5 hours at 60° C. Then the mixture is evaporated down i. vac., the residue is combined with water and extracted with ethyl acetate. The combined organic phases are dried over sodium sulphate, evaporated down i. vac. and the residue obtained is purified by chromatography on silica gel (eluting gradient: petroleum ether/ethyl acetate 3:2->0:1).
Yield: 0.99 g (50%)
$R_t$ value: 2.56 min
$C_{14}H_{17}NO_4$ (263.30)
Mass spectrum: $(M+H)^+=264$ (c) 3-methoxy-4-(piperidin-2-on-1-yl)-benzoic acid Prepared analogously to Example 39d from methyl 3-methoxy-4-(piperidin-2-on-1-yl)-benzoate and lithium hydroxide in ethanol.
Yield: 95%
$R_f$ value: 0.10 (silica gel; petroleum ether/ethyl acetate=1:2)
$C_{13}H_{15}NO_4$ (249.27)
Mass spectrum: $(M+H)^+=250$ (d) N-[(1S)-1-(5-chloro-1H-benzimidazol-2-yl)-ethyl]-3-methoxy-4-(piperidin-2-on-1-yl)-benzamide Prepared analogously to Example 1f from 3-methoxy-4-(piperidin-2-on-1-yl)-benzoic acid, TBTU, NMM and (1S)-1-(5-chloro-1H-benzimidazol-2-yl)ethylamine in DMF and subsequent purification by preparative HPLC.
Yield: 75%
$R_t$ value: 2.35 min
$C_{22}H_{23}ClN_4O_3 \cdot CF_3COOH$ (540.93/426.90)
Mass spectrum: $(M+H)^+=427/429$ (chlorine isotope)
The following compounds were prepared analogously:

| No. | structural formula / Name | Yield | mass peak(s) | $R_f$ value or $R_t$ |
|---|---|---|---|---|
| 70 | N-[(1R)-1-(5-chloro-1H-benzimidazol-2-yl)-2-methoxy-ethyl]-3-methoxy-4-(piperidin-2-on-1-yl)-benzamide | Σ: 31% | $(M+H)^+=$ 457/459 (chlorine isotope) | 2.31 min |
| 85 | N-[(1S)-1-(5-chloro-1H-benzimidazol-2-yl)-ethyl]-4-(piperidin-2-on-1-yl)-3-trifluoromethoxy-benzamide | Σ: 0.8% | $(M+H)^+=$ 481/483 (chlorine isotope) | 2.56 min |

| No. | structural formula / Name | Yield | mass peak(s) | $R_f$ value or $R_t$ |
|---|---|---|---|---|
| 86 | 3-bromo-N-[(1S)-1-(5-chloro-1H-benzimidazol-2-yl)-ethyl]-4-(piperidin-2-on-1-yl)-benzamide | Σ: 6.2% | $(M + H)^+ =$ 475/477/479 (bromine and chlorine isotope) | 2.57 min |
| 87 | 3-bromo-N-[(1R)-1-(5-chloro-1H-benzimidazol-2-yl)-2-methoxy-ethyl]-4-(piperidin-2-on-1-yl)-benzamide | Σ: 6.2% | $(M + H)^+ =$ 505/507/509 (bromine and chlorine isotope) | 2.57 min |

Example 73

N-[(1S)-1-(5-chloro-1H-benzimidazol-2-yl)-ethyl]-4-(1,1-dioxo-6-methyl-[1,2,6]thia-diazinan-2-yl)-3-methyl-benzamide

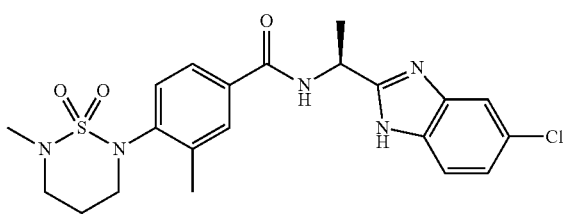 [SMILES: Cc1cc(C(=O)N[C@@H](C)c2nc3cc(Cl)ccc3[nH]2)ccc1N1CCCN(C)S1(=O)=O]

(a) methyl 4-(1,1-dioxo-6-methyl-[1,2,6]-thiadiazinan-2-yl)-3-methyl-benzoate 400 mg (1.41 mmol) methyl 4-(1,1-dioxo-[1,2,6]-thiadiazinan-2-yl)-3-methyl-benzoate dissolved in 4 ml DMF at 40° C. are combined with 240 mg (2.14 mmol) potassium-tert.-butoxide and 96 μl (1.54 mmol) methyl iodide and stirred for 5 hours at 40° C. The reaction solution is evaporated down i. vac., combined with water and the aqueous phase is extracted with ethyl acetate. The combined organic phases are dried over sodium sulphate and evaporated down i. vac.

Yield: 220 mg (52%)

$C_{13}H_{18}N_2O_4S$ (298.36)

Mass spectrum: $(M+H)^+=299$ $R_f$ value: 0.44 (silica gel; petroleum ether/ethyl acetate=3:2)

(b) 4-(1,1-dioxo-6-methyl-[1,2,6]thiadiazinan-2-yl)-3-methyl-benzoic acid

Prepared analogously to Example 39d from methyl 4-(1,1-dioxo-3-methyl-[1,2,6]thiadiazinan-2-yl)-3-methyl-benzoate and lithium hydroxide in ethanol.

Yield: (81%)

$C_{12}H_{16}N_2O_4S$ (284.34)

Mass spectrum: $(M+H)^+=285$ $R_f$ value: 0.07 (silica gel; dichloromethane/methanol=19:1)

(c) N-[(1S)-1-(5-chloro-1H-benzimidazol-2-yl)-ethyl]-4-(1,1-dioxo-6-methyl-[1,2,6]thiadiazinan-2-yl)-3-methyl-benzamide Prepared analogously to Example 1f from 4-(1,1-dioxo-3-methyl-[1,2,6]thiadiazinan-2-yl)-3-methyl-benzoic acid, (1S)-1-(5-chloro-1H-benzimidazol-2-yl)-ethylamine, TBTU and NMM in DMF with subsequent purification by preparative HPLC.

Yield: 55%

$C_{21}H_{24}ClN_5O_3S \cdot CF_3COOH$ (576.00/461.97)

Mass spectrum: $(M+H)^+=462/464$ (chlorine isotope)

$R_t$ value: 2.50 min

The following compound is prepared analogously:

| No. | structural formula | Name | Yield | mass peak(s) | $R_f$ value |
|---|---|---|---|---|---|
| 74 | | N-[(1R)-1-(5-chloro-1H-benzimidazol-2-yl)-2-methoxy-ethyl]-4-(1,1-dioxo-6-methyl-[1,2,6]thiadiazinan-2-yl)-3-methyl-benzamide | Σ: 20% | $(M+H)^+ =$ 492/494 (chlorine isotope) | 2.56 min |

Example 75

N-[(1R)-1-(5-bromo-1H-benzimidazol-2-yl)-2-methoxy-ethyl]-3-methyl-4-(morpholin-3-on-4-yl)-benzamide

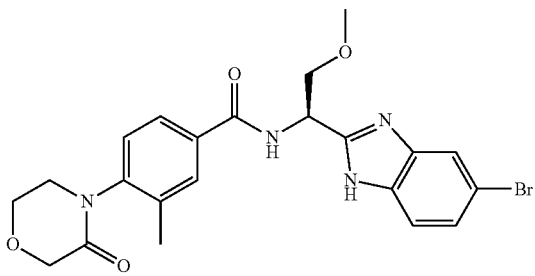 [SMILES: COC[C@H](NC(=O)c1ccc(N2CCOCC2=O)c(C)c1)c1nc2cc(Br)ccc2[nH]1]

(a) N'-(2-amino-4-bromo-phenyl)-N-Boc-(S)-O-methyl-serinamide and N'-(2-amino-5-bromo-phenyl)-N-Boc-(S)-O-methyl-serinamide 2.50 g (6.24 mmol) of the dicyclohexylammonium salt of N-Boc-(S)-O-methyl-serine are dissolved in 20 ml 5% citric acid, the aqueous phase is extracted 2× with 20 ml of ethyl acetate, the combined organic phases are dried over sodium sulphate and freed from solvent i. vac. The residue is dissolved together with 1.23 g (6.55 mmol) 4-bromo-1,2-phenylenediamine in 30 ml THF and 1.42 ml (14.0 mmol) triethylamine and 4.97 ml (7.80 mmol) of a 50% solution of PPA in ethyl acetate are added with stirring in the ice bath. After 5 minutes stirring in the ice bath the mixture is heated to ambient temperature and stirred for 23 hours at ambient temperature. The reaction mixture is poured into 100 ml of water and the aqueous phase is extracted with ethyl acetate. The combined organic phases are extracted with sat. sodium carbonate solution and water, dried over sodium sulphate and evaporated down i. vac.

Yield: 2.38 g (98%) mixture of the two regioisomers
$C_{15}H_{22}BrN_3O_4$ (388.26)
Mass spectrum: $(M+H)^+$=388/390 (bromine isotope)
$R_f$ value: 0.63/0.68 (silica gel; dichloromethane/ethanol=9:1)

(b) (1R)-N-Boc-1-(5-bromo-1H-benzimidazol-2-yl)-2-methoxy-ethylamine 2.38 g (6.13 mmol) of the mixture obtained in 75a are dissolved in 150 ml of toluene and 1.84 ml (30.7 mmol) acetic acid and 4.00 g molecular sieve, 3A, are added. The reaction mixture is stirred for 3 hours at 55° C. and then cooled for 15 minutes in the ice bath. The reaction mixture is filtered and poured into a mixture of 500 ml each of water and ethyl acetate. After vigorous mixing the organic phase is separated off, washed with sat. sodium chloride solution, dried over sodium sulphate and evaporated down i. vac. The residue is purified by chromatography on silica gel (eluting gradient: dichloromethane/ethanol 100:0->97:3).

Yield: 1.40 g (62%)
$C_{15}H_{20}BrN_3O_3$ (370.24)
Mass spectrum: $(M+H)^+$=370/372 (bromine isotope)
$R_f$ value: 0.81 (silica gel; dichloromethane/ethanol=9:1)

(c) (1R)-1-(5-bromo-1H-benzimidazole-1-yl)-2-methoxy-ethylamine

Prepared analogously to Example 1g from (1R)-N-Boc-1-(5-bromo-1H-benzimidazol-2-yl)-2-methoxy-ethylamine and TFA in dichloromethane.

Yield: 51%
$C_{10}H_{12}BrN_3O$ (270.13)
Mass spectrum: $(M+H)^+$=270/272 (bromine isotope)
$R_f$ value: 0.20 (silica gel, dichloromethane/ethanol 9:1)

(d) N-[(1R)-1-(5-bromo-1H-benzimidazol-2-yl)-2-methoxy-ethyl]-3-methyl-4-morpholin-3-on-4-yl)-benzamide Prepared analogously to Example 1f from 3-methyl-4-(morpholin-3-on-4-yl)-benzoic acid, (1R)-1-(5-bromo-1H-benzimidazol-2-yl)-2-methoxy-ethylamine, TBTU and DIPEA in THF with subsequent purification by chromatography on silica gel.

Yield: quant.
$C_{22}H_{23}BrN_4O_4$ (487.35)
Mass spectrum: $(M+H)^+$=487/489 (bromine isotope)
$R_f$ value: 0.56 (silica gel; dichloromethane/ethanol=9:1)

Example 76

N-[(1S)-1-(5-chloro-1H-benzimidazol-2-yl)-3-(1H-tetrazol-5-yl)-propyl]-3-methyl-4-(morpholin-3-on-4-yl)-benzamide

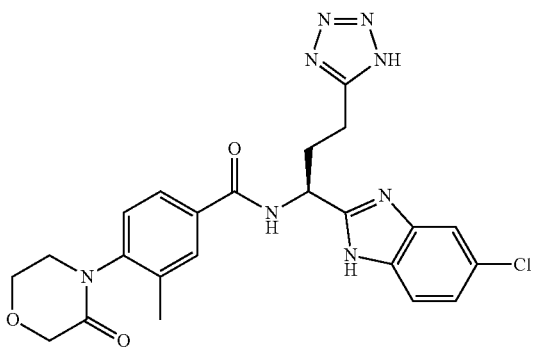 [SMILES: Cc1cc(C(=O)N[C@@H](CCc2nnn[nH]2)c2nc3cc(Cl)ccc3[nH]2)ccc1N1CCOCC1=O]

(a) ethyl (2S)-2-(benzyloxycarbonyl-amino)-4-cyano-butyrate 5.00 g (11.3 mmol) dicyclohexylammonium-(2S)-2-(benzyloxycarbonyl-amino)-4-cyano-butanoate are stirred into in 100 ml of 5% citric acid solution and then extracted with ethyl acetate. The combined organic phases are dried over sodium sulphate and the solvent is distilled off i. vac. The residue is dissolved in 70 ml THF, 4.35 g (13.5 mmol) TBTU and 6.35 ml (33.8 mmol) DIPEA are added and the mixture is stirred for 10 minutes at ambient temperature. Then 50 ml of ethanol are added and the mixture is refluxed for 16 hours. Then the reaction mixture is evaporated down i. vac., taken up in ethyl acetate, washed with semisaturated sodium hydrogen carbonate solution and water, dried over sodium sulphate and evaporated down i. vac.

Yield: 3.20 g (98%)
$C_{15}H_{18}N_2O_4$ (290.32)
Mass spectrum: $(M+NH_4)^+=308$
$R_f$ value: 0.80 (silica gel; dichloromethane/ethanol=9:1)

(b) ethyl (2S)-2-(benzyloxycarbonyl-amino)-4-(1H-tetrazol-5-yl)-butyrate 3.20 g (11.0 mmol) ethyl (2S)-2-(benzyloxycarbonyl-amino)-4-cyano-butyrate are dissolved in 40 ml of toluene and 1.08 g (16.5 mmol) sodium azide and 2.28 g (16.5 mmol) triethylamine-hydrochloride are added. The reaction mixture is heated to 85° C. for 24 hours, cooled to ambient temperature and extracted with water. The combined aqueous phases are acidified to pH 2 with semiconc. hydrochloric acid, the resulting precipitate is suction filtered, washed with water and dried at 50° C.

Yield: 2.90 g (79%)
$C_{15}H_{19}N_5O_4$ (333.34)
Mass spectrum: $(M+H)^+=334$
$R_f$ value: 0.50 (silica gel; dichloromethane/ethanol=9:1)

(c) (2S)-2-(benzyloxycarbonyl-amino)-4-(1H-tetrazol-5-yl)-butyric acid

Prepared analogously to Example 30b from ethyl (2S)-2-(benzyloxycarbonyl-amino)-4-(1H-tetrazol-5-yl)-butyrate and lithium hydroxide in a mixture of solvents from water and THF.

Yield: quant.
$C_{13}H_{15}N_5O_4$ (305.29)
Mass spectrum: $(M+H)^+=306$
$R_f$ value: 0.30 (silica gel; dichloromethane/ethanol=4:1)

(d) N'-(2-amino-4-chloro-phenyl)-(2S)-2-(benzyloxycarbonyl-amino)-4-(1H-tetrazol-5-yl)-butyric acid amide and N'-(2-amino-5-chloro-phenyl)-(2S)-2-(benzyloxycarbonyl-amino)-4-(1H-tetrazol-5-yl)-butyric acid amide Prepared analogously to Example 47a from (2S)-2-(benzyloxycarbonyl-amino)-4-(1H-tetrazol-5-yl)-butyric acid and 4-chloro-1,2-phenylenediamine with DCC in THF.

Yield: quant., mixture of the two regioisomers, slightly contaminated
$C_{19}H_{20}ClN_7O_3$ (429.86)
$R_f$ value: 0.20 (silica gel; dichloromethane/ethanol=9:1)

(e) (1S)-N-(benzyloxycarbonyl)-1-(5-chloro-1H-benzimidazol-2-yl)-3-(1H-tetrazol-5-yl)-propylamine Prepared analogously to Example 47b from the product obtained in Example 76d and acetic acid.

Yield: quant.
$C_{13}H_{18}ClN_7O_2 \cdot CH_3COOH$ (471.90/411.85)
$R_f$ value: 0.25 (silica gel; dichloromethane/ethanol/conc. ammonia=4:1:0.1)

(f) (1S)-1-(5-chloro-1H-benzimidazol-2-yl)-3-(1H-tetrazol-5-yl)-propylamine 2.10 g (4.45 mmol) (1S)-N-(benzyloxycarbonyl)-1-(5-chloro-1H-benzimidazol-2-yl)-3-(1H-tetrazol-5-yl)-propylamine in 30 ml dichloromethane are combined with 1.9 ml (13.4 mmol) iodo-trimethylsilane and stirred for 16 hours at ambient temperature. Then 20 ml of methanol are added, the mixture is stirred for a further 30 minutes at ambient temperature and the reaction mixture is evaporated down completely i. vac. The residue is purified by chromatography on silica gel (eluting gradient: dichloromethane/(ethanol/conc. ammonia 95:5)=70/30->60:40).

Yield: 690 mg (56%)
$C_{11}H_{12}ClN_7$ (277.71)
Mass spectrum: $(M+H)^+=278/280$ (chlorine isotope)
$R_f$ value: 0.15 (silica gel; dichloromethane/ethanol=3:2+1% conc. ammonia)

(g) N-[(1S)-1-(5-chloro-1H-benzimidazol-2-yl)-3-(1H-tetrazol-5-yl)-propyl]-3-methyl-4-(morpholin-3-on-4-yl)-benzamide Prepared analogously to Example 1f from 3-methyl-4-(morpholin-3-on-4-yl)-benzoic acid, (1S)-1-(5-chloro-1H-benzimidazol-2-yl)-3-(1H-tetrazol-5-yl)-propylamine, TBTU and DIPEA in THF with subsequent purification by chromatography on silica gel.

Yield: 33%
$C_{23}H_{23}ClN_8O_3$ (494.93)
Mass spectrum: $(M+H)^+=495/497$ (chlorine isotope)
$R_f$ value: 0.20 (silica gel; dichloromethane/ethanol=4:1)

Example 77

N-[(1S)-1-(5-chloro-1H-benzimidazol-2-yl)-3-methoxy-propyl]-3-methyl-4-(morpholin-3-on-4-yl)-benzamide

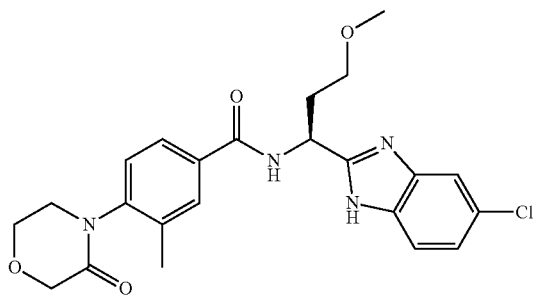

(a) N'-(2-amino-4-chloro-phenyl)-(2S)-2-(Boc-amino)-3-methoxy-propionic acid amide and N'-(2-amino-5-chloro-phenyl)-(2S)-2-(Boc-amino)-3-methoxy-propionic acid amide 4.90 g (21.0 mmol) (2S)-2-(Boc-amino)-3-methoxy-propionic acid are dissolved in 20 ml THF and combined with 13.57 g (42.0 mmol) TBTU and 5.76 ml (52.5 mmol) triethylamine and stirred for 30 minutes at ambient temperature. Then 3.00 g (21.0 mmol) 4-chloro-1,2-phenylenediamine in 20 ml THF are added and the mixture is stirred for 16 hours at ambient temperature. Then the reaction mixture is evaporated down i. vac., poured into water and extracted with ethyl acetate. The combined organic phases are washed with sat. sodium hydrogen carbonate solution, dried over sodium sulphate and evaporated down i. vac. The residue is purified by chromatography on silica gel (eluant: dichloromethane/methanol 99:1).

Yield: 5.60 g (75%) mixture of the two regioisomers
$C_{16}H_{24}ClN_3O_3$ (357.83)
Mass spectrum: $(M+H)^+$=358/360 (chlorine isotope)
$R_f$ value: 0.26 (silica gel; dichloromethane/methanol=99:1)

(b) (1S)-N-Boc-1-(5-chloro-1H-benzimidazol-2-yl)-3-methoxy-propylamine

Prepared analogously to Example 47b from the product obtained in Example 77a and acetic acid.
Yield: 96%
$C_{16}H_{22}ClN_3O_3$ (339.82)
Mass spectrum: $(M+H)^+$=340/342 (chlorine isotope)
$R_f$ value: 0.80 (silica gel; dichloromethane/methanol=19:1)

(c) (1S)-1-(5-chloro-1H-benzimidazol-2-yl)-3-methoxy-propylamine

Prepared analogously to Example 1g from (1S)-N-Boc-1-(5-chloro-1H-benzimidazol-2-yl)-3-methoxy-propylamine and TFA in dichloromethane.
Yield: 31%
$C_{11}H_{14}ClN_3O$ (239.70)
Mass spectrum: $(M+H)^+$=240/242 (chlorine isotope)
$R_f$ value: 0.10 (silica gel; dichloromethane/ethanol=9:1)

(d) N-[(1S)-1-(5-chloro-1H-benzimidazol-2-yl)-3-methoxy-propyl]-3-methyl-4-(morpholin-3-on-4-yl)-benzamide Prepared analogously to Example 1f from 3-methyl-4-(morpholin-3-on-4-yl)-benzoic acid, (1S)-1-(5-chloro-1H-benzimidazol-2-yl)-3-methoxy-propylamine, TBTU and DIPEA in THF with subsequent purification by chromatography on silica gel.
Yield: 59%
$C_{23}H_{25}ClN_4O_4$ (456.92)
Mass spectrum: $(M+H)^+$=457/459 (chlorine isotope)
$R_f$ value: 0.51 (silica gel; dichloromethane/ethanol=9:1)
The following compound is prepared analogously:

| No. | structural formula / Name | Yield | mass peak(s) | $R_f$ value or $R_t$ |
|---|---|---|---|---|
| 148 | N-[1-(5-chloro-1H-benzimidazol-2-yl)-1-methyl-ethyl]-3-methyl-4-(morpholin-3-on-4-yl)-benzamide | Σ: 57% | $(M+H)^+$ = 427/429 (chlorine isotope) | 0.5 (silica gel; dichloromethane/ ethanol = 9:1) |

| No. | structural formula | Name | Yield | mass peak(s) | $R_f$ value or $R_t$ |
|---|---|---|---|---|---|
| 88 | 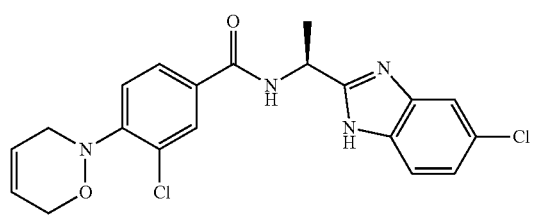 N-[1-(5-chloro-1H-benzimidazol-2-yl)-1-(furan-2-yl)-methyl]-3-methyl-4-(morpholin-3-on-4-yl)-benzamide | | Σ: 3.6% | $(M+H)^+ =$ 465/467 (chlorine isotope) | 2.38 min |

Example 82

3-chloro-N-[(1S)-1-(5-chloro-1H-benzimidazol-2-yl)-ethyl]-4-(3,6-dihydro-[1,2]oxazin-2-yl)-benzamide

(a) methyl 3-chloro-4-nitroso-benzoate 8.00 g (29.6 mmol) potassium peroxodisulphate are added to 6.0 ml of conc. sulphuric acid with stirring, stirred for 30 minutes at ambient temperature under a nitrogen atmosphere, the mixture is stirred into 50 g ice and neutralised with 14 g sodium carbonate. The solution obtained is combined with a suspension of 2.78 g (15.0 mmol) methyl 4-amino-3-chlorobenzoate in 300 ml of water and stirred for 16 hours at ambient temperature. The reaction mixture is suction filtered, the filter cake is washed with water, dried in the air and purified by chromatography on silica gel (eluant: petroleum ether/ethyl acetate 9:1).

Yield: 1.00 g (33%)

$C_8H_6ClNO_3$ (199.59)

Mass spectrum: $(M+H)^+=199/201$ (chlorine isotope)

$R_f$ value: 0.55 (silica gel; petroleum ether/ethyl acetate=4:1)

(b) methyl 3-chloro-4-(3,6-dihydro-[1,2]oxazin-2-yl)-benzoate 1.00 g (5.01 mmol) methyl 3-chloro-4-nitroso-benzoate are placed in 10 ml chloroform and a freshly prepared solution of 1.10 g (20.3 mmol) butadiene in 6 ml chloroform is added dropwise with stirring at 0° C. The reaction mixture is stirred for 30 minutes at 0-10° C. and for 16 hours at ambient temperature, evaporated down i. vac. and purified by chromatography on silica gel (eluant: petroleum ether/ethyl acetate=19:1).

Yield: 1.00 g (79%)

$C_{12}H_{12}ClNO_3$ (253.68)

Mass spectrum: $(M+H)^+=254/256$ (chlorine isotope)

$R_f$ value: 0.50 (silica gel; petroleum ether/ethyl acetate=4:1)

(c) 3-chloro-4-(3,6-dihydro-[1,2]oxazin-2-yl)-benzoic acid

Prepared analogously to Example 2d from methyl 3-chloro-4-(3,6-dihydro-[1,2]oxazin-2-yl)-benzoate and sodium hydroxide in a solvent mixture of water and ethanol.

Yield: 90%

$C_{11}H_{10}ClNO_3$ (239.66)

Mass spectrum: $(M-H)^-=238/240$ $R_f$ value: 0.20 (silica gel; petroleum ether/ethyl acetate=4:1)

(d) 3-chloro-N-[(1S)-1-(5-chloro-1H-benzimidazol-2-yl)-ethyl]-4-(3,6-dihydro-[1,2]oxazin-2-yl)-benzamide Prepared analogously to Example 1f from 3-chloro-4-(3,6-dihydro-[1,2]oxazin-2-yl)-benzoic acid, (1S)-1-(5-chloro-1H-benzimidazol-2-yl)-ethylamine, TBTU and NMM in DMF.

Yield: 88%

$C_{20}H_{18}Cl_2N_4O_2$ (417.29)

Mass spectrum: $(M+H)^+=417/419/421$ (chlorine isotope)

$R_f$ value: 0.35 (silica gel; petroleum ether/ethyl acetate=1:1)

Example 83

3-chloro-N-[(1R)-1-(5-chloro-1H-benzimidazol-2-yl)-2-methoxy-ethyl]-4-(1,1-dioxo-[1,2]thiazinan-2-yl)-benzamide

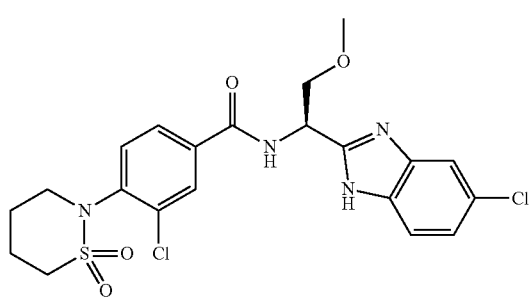 [SMILES: COC[C@H](NC(=O)c1ccc(N2CCCCS2(=O)=O)c(Cl)c1)c1nc2cc(Cl)ccc2[nH]1]

(a) 2-chloro-N-(4-chlorbutyl-sulphonyl)-4-methyl-aniline 1.30 ml (10.7 mmol) 2-chloro-4-methyl-aniline are placed in 30 ml of pyridine, combined with 2.67 g (10.5 mmol) 75% m 4-chlorobutyl-sulphonic acid chloride and stirred for 16 hours at ambient temperature. The reaction mixture is poured into water and extracted with ethyl acetate. The combined organic phases are washed with 6-molar hydrochloric acid, dried over sodium sulphate and evaporated down i. vac. The residue is purified by chromatography on silica gel (eluting gradient: petroleum ether/ethyl acetate=9:1->7:3).

Yield: 1.27 g (40%)
$C_{11}H_{15}Cl_2NO_2S$ (296.21)
Mass spectrum: $(M+H)^+$=296/298/300 (chlorine isotope)
$R_f$ value: 0.42 (silica gel; petroleum ether/ethyl acetate=4:1)

(b) 3-chloro-4-(1,1-dioxo-[1,2]thiazinan-2-yl)-toluene 1.27 g (4.29 mmol) 2-chloro-N-(4-chlorbutyl-sulphonyl)-4-methyl-aniline are stirred together with 722 mg (6.43 mmol) potassium-tert.-butoxide in 50 ml DMF for 16 hours at 60° C. Then the reaction mixture is poured into water and extracted with ethyl acetate. The combined organic phases are dried over sodium sulphate and evaporated down i. vac. The residue is purified by chromatography on silica gel (eluant: petroleum ether/ethyl acetate=3:2).

Yield: 850 mg (76%)
$C_{11}H_{14}ClNO_2S$ (259.75)
Mass spectrum: $(M+H)^+$=260/262 (chlorine isotope)
$R_f$ value: 0.27 (silica gel; petroleum ether/ethyl acetate=4:1)

(c) 3-chloro-4-(1,1-dioxo-[1,2]thiazinan-2-yl)-benzoic acid 250 mg (0.96 mmol) 3-chloro-4-(1,1-dioxo-[1,2]thiazinan-2-yl)-toluene are suspended in 10 ml of water and combined with 456 mg (2.89 mmol) potassium permanganate and 39 mg (0.98 mmol) sodium hydroxide. The reaction mixture is refluxed for 4 hours. After cooling to ambient temperature sodium thiosulphate is added to decolorise the mixture which is then extracted with ethyl acetate. The combined organic phases are dried over sodium sulphate and evaporated down i. vac. The residue is purified by chromatography on silica gel (eluant: dichloromethane/methanol=19:1).

Yield: 50 mg (18%)
$C_{11}H_{12}ClNO_4S$ (289.74)
Mass spectrum: $(M+H)^+$=290/292
$R_t$ value: 2.50 min

(d) 3-chloro-N-[(1R)-1-(5-chloro-1H-benzimidazol-2-yl)-2-methoxy-ethyl]-4-(1,1-dioxo-[1,2]thiazinan-2-yl)-benzamide Prepared analogously to Example 1f from 3-chloro-4-(1,2-dioxo-[1,2]thiazinan-2-yl)-benzoic acid, (1R)-1-(5-chloro-1H-benzimidazol-2-yl)-2-methoxy-ethylamine, TBTU and NMM in DMF with subsequent purification by preparative HPLC.

Yield: 34%
$C_{21}H_{22}Cl_2N_4O_4S$ (497.40)
Mass spectrum: $(M+H)^+$=497/499/501 (chlorine isotope)
$R_t$ value: 2.53 min

Example 84

N-[(1R)-1-(5-chloro-1H-benzimidazol-2-yl)-2-methoxy-ethyl]-4-(1,1-dioxo-[1,2]thiazepan-2-yl)-3-methyl-benzamide

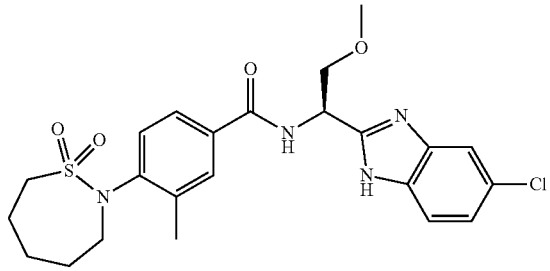 [SMILES: COC[C@H](NC(=O)c1ccc(N2CCCCCS2(=O)=O)c(C)c1)c1nc2cc(Cl)ccc2[nH]1]

(a) methyl 4-(5-chloropentyl-sulphonyl-amino)-3-methyl-benzoate

Prepared analogously to Example 83a from methyl 4-amino-3-methyl-benzoate and 5-chloropentyl-sulphonic acid chloride in pyridine. Yield: 43%

$C_{14}H_{20}ClNO_4S$ (333.83)
Mass spectrum: $(M+H)^+$=334/336 (chlorine isotope)
$R_f$ value: 0.72 (silica gel; petroleum ether/ethyl acetate=7:3)

(b) methyl 4-(1,1-dioxo-[1,2]thiazepan-2-yl)-3-methyl-benzoate

Prepared analogously to Example 83b from methyl 4-(5-chloropentyl-sulphonyl-amino)-3-methyl-benzoate and potassium-tert.-butoxide in DMF.

Yield: 19%
$C_{14}H_{19}NO_4S$ (297.37)
Mass spectrum: $(M+H)^+$=298
$R_t$ value: 0.30 (silica gel; petroleum ether/ethyl acetate=4:1)

(c) 4-(1,1-dioxo-[1,2]thiazepan-2-yl)-3-methyl-benzoic acid

Prepared analogously to Example 39d from methyl 4-(1,1-dioxo-[1,2]thiazepan-2-yl)-3-methyl-benzoate and lithium hydroxide in a solvent mixture of water and ethanol.

Yield: 60%

$C_{13}H_{17}NO_4S$ (283.34)

Mass spectrum: (M+H)$^+$=284

$R_t$ value: 2.60 min

(d) N-[(1R)-1-(5-chloro-1H-benzimidazol-2-yl)-2-methoxy-ethyl]-4-(1,1-dioxo-[1,2]thiazepan-2-yl)-3-methyl-benzamide Prepared analogously to Example 1f from 4-(1,2-dioxo-[1,2]thiazepan-2-yl)-3-methyl-benzoic acid, (1R)-1-(5-chloro-1H-benzimidazol-2-yl)-2-methoxy-ethylamine, TBTU and NMM in DMF with subsequent purification by chromatography on silica gel.

Yield: 75%

$C_{23}H_{27}ClN_4O_4S$ (491.00)

Mass spectrum: (M+H)$^+$=491/493 (chlorine isotope)

$R_t$ value: 2.60 min

Example 89

3-chloro-N-[(1S)-1-(5-chloro-1H-benzimidazol-2-yl)-ethyl]-4-([1,2]oxazinan-2-yl)-benzamide

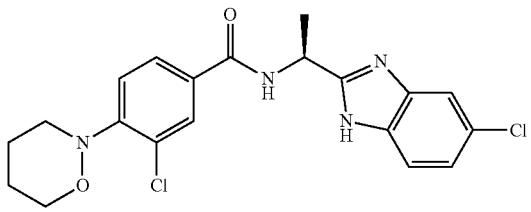

209 mg (0.50 mmol) 3-chloro-N-[(1S)-1-(5-chloro-1H-benzimidazol-2-yl)-ethyl]-4-(3,6-dihydro-[1,2]oxazin-2-yl)-benzamide together with 100 mg 10% palladium charcoal in 5 ml of ethyl acetate for 7 minutes are hydrogenated at ambient temperature at 5 bar under a hydrogen atmosphere. Then the mixture is suction filtered, the filtrate is evaporated down i. vac. and evaporated again with ether.

Yield: 200 mg (95%)

$C_{20}H_{20}Cl_2N_4O_2$ (419.30)

Mass spectrum: (M+H)$^+$=419/421/423 (chlorine isotope)

$R_f$ value: 0.40 (silica gel; petroleum ether/ethyl acetate=1:1)

Example 90

N-[(1R)-1-(5-chloro-1H-benzimidazol-2-yl)-2-methoxy-ethyl]-3-methyl-4-(5-oxo-[1,4]oxazepan-4-yl)-benzamide

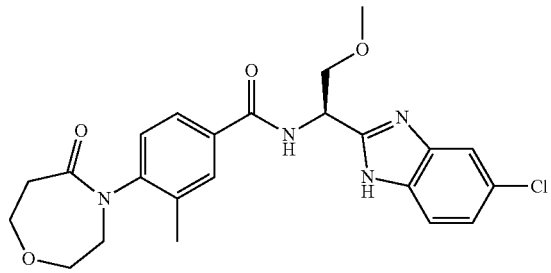 [SMILES: COC[C@H](NC(=O)c1ccc(N2CCOCCC2=O)c(C)c1)c1nc2cc(Cl)ccc2[nH]1]

(a) ethyl 3-(2-benzyloxy-ethoxy)-propionate 8.53 ml (60.0 mmol) benzyloxy-ethanol are combined with 13 mg (0.57 mmol) sodium in 40 ml THF, then when it has dissolved 5.95 ml (54.7 mmol) ethyl acrylate are added under an argon atmosphere and stirred for 20 hours at ambient temperature. After neutralising with 0.6 ml 1-molar hydrochloric acid the reaction mixture is evaporated down i. vac., the residue is taken up in sat. sodium chloride solution and extracted with ethyl acetate. The combined organic phases are washed with sat. sodium chloride solution, dried over sodium sulphate and evaporated down i. vac. The residue is purified by chromatography on silica gel (eluant: petroleum ether/ethyl acetate=4:1).

Yield: 3.73 g (25%)

$C_{14}H_{20}O_4$ (252.31)

Mass spectrum: (M+H)$^+$=253

$R_f$ value: 0.48 (silica gel; petroleum ether/ethyl acetate=4:1)

(b) ethyl 3-(2-hydroxy-ethoxy)-propionate 3.73 g (14.8 mmol) ethyl 3-(2-benzyloxy-ethoxy)-propionate are hydrogenated together with 665 mg 10% palladium charcoal in 70 ml of ethanol for 44 minutes at ambient temperature under a hydrogen atmosphere at 3 bar. Then the mixture is suction filtered and the filtrate is evaporated down i. vac.

Yield: 2.26 g (94%)

$C_7H_{14}O_4$ (162.18)

Mass spectrum: (M+H)$^+$=163

(c) ethyl 3-(2-chloro-ethoxy)-propionate 2.26 g (13.9 mmol) ethyl 3-(2-hydroxy-ethoxy)-propionate are suspended in 5 ml (68.5 mmol) thionyl chloride and 20 µl (0.27 mmol) DMF are added. The reaction mixture is refluxed for 4 hours and then evaporated down i. vac. The product is further reacted without any more purification.

Yield: quant.

$C_7H_{13}O_3$ (180.63)

Mass spectrum: (M+H)$^+$=181/183 (chlorine isotope)

(d) 3-(2-chloro-ethoxy)-propionic acid 2.00 g (11.1 mmol) ethyl 3-(2-chloro-ethoxy)-propionate are suspended in 8 ml of ethanol and 4.96 ml (16.6 mmol) of 8% lithium hydroxide solution are added. The mixture is stirred for 4 hours at ambient temperature, then evaporated down i. vac., acidified with 2-molar hydrochloric acid, combined with diethyl ether and dried over sodium sulphate. Then it is filtered off and evaporated down i. vac.

Yield: 1.51 g (89%)
$C_5H_9ClO_3$ (152.58)
Mass spectrum: $(M-H)^-=151/153$ (chlorine isotope)

(e) 3-(2-chloro-ethoxy)-propionic acid-chloride

Prepared analogously to Example 90c from 3-(2-chloro-ethoxy)-propionic acid and thionyl chloride with DMF.
Yield: 91%
$C_5H_8Cl_2O_2$ (171.02)

(f) methyl 4-[3-(2-chloro-ethoxy)-propionyl-amino]-3-methyl-benzoate 1.70 g (10.3 mmol) methyl 4-amino-3-methyl-benzoate in 10 ml THF are combined with 2.84 ml (20.6 mmol) triethylamine and stirred for 20 minutes at ambient temperature. Then a solution of 1.78 g (10.4 mmol) 3-(2-chloro-ethoxy)-propionic acid-chloride in 25 ml THF is added dropwise and the mixture is stirred for a further 2.5 hours at ambient temperature. Then water is added and the mixture is extracted with ethyl acetate. The combined organic phases are dried over sodium sulphate and evaporated down completely i. vac. The residue is purified by chromatography on silica gel (eluting gradient: petroleum ether/ethyl acetate=7:3->6:4).

Yield: 1.25 g (41%)
$C_{14}H_{18}ClNO_4$ (299.75)
Mass spectrum: $(M+H)^+=300/302$ (chlorine isotope)
$R_f$ value: 0.15 (silica gel; petroleum ether/ethyl acetate=7:3)

(g) methyl 3-methyl-4-(5-oxo-[1,4]oxazepan-4-yl)-benzoate 900 mg (3.00 mmol) 4-[3-(2-chloro-ethoxy)-propionyl-amino]-3-methyl-benzoate methyl are stirred in 40 ml DMF together with 520 mg (4.63 mmol) potassium tert.-butoxide and 12 mg (80 µmol) sodium iodide for 3 hours at 60° C. After evaporation i. vac. the residue is combined with water, extracted with ethyl acetate and the combined organic phases are dried over sodium sulphate and evaporated down i. vac. The residue is purified by chromatography on silica gel (eluant: petroleum ether/ethyl acetate=11:9).

Yield: 310 mg (39%)
$C_{14}H_{17}NO_4$ (263.29)
Mass spectrum: $(M+H)^+=264$

(h) 3-methyl-4-(5-oxo-[1,4]oxazepan-4-yl)-benzoic acid

Prepared analogously to Example 39d from methyl 3-methyl-4-(5-oxo-[1,4]oxazepan-4-yl)-benzoate and lithium hydroxide in a solvent mixture of water and ethanol.
Yield: 69%
$C_{13}H_{15}NO_4$ (249.26)
Mass spectrum: $(M+H)^+=250$
$R_t$ value: 2.06 min

(i) N-[(1R)-1-(5-chloro-1H-benzimidazol-2-yl)-2-methoxy-ethyl]-3-methyl-4-(5-oxo-[1,4]oxazepan-4-yl)-benzamide Prepared analogously to Example 1f from 3-methyl-4-(5-oxo-[1,4]oxazepan-4-yl)-benzoic acid, (1R)-1-(5-chloro-1H-benzimidazol-2-yl)-2-methoxy-ethylamine, TBTU and NMM in DMF with subsequent purification by preparative HPLC.

Yield: 83%
$C_{23}H_{25}ClN_4O_4$ (456.92)
Mass spectrum: $(M+H)^+=457/459$ (chlorine isotope)
$R_t$ value: 2.23 min

Example 91

N-[(1S)-1-(5-chloro-1H-benzimidazol-2-yl)-ethyl]-4-(4,4-dimethyl-2-oxo-imidazolidin-1-yl)-3-methyl-benzamide

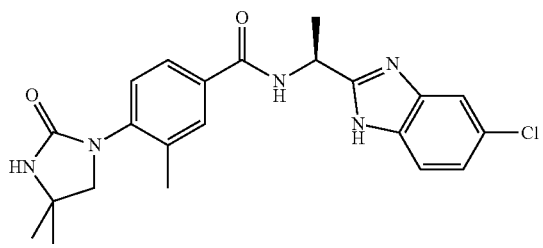 [SMILES: Cc1cc(C(=O)N[C@@H](C)c2nc3cc(Cl)ccc3[nH]2)ccc1N1CC(C)(C)NC1=O]

(a) methyl 4-(3-[1,1-dimethyl-2-hydroxy-ethyl]ureido)-3-methyl-benzoate 5.70 g (29.8 mmol) methyl 4-isocyanato-3-methyl-benzoate are dissolved in 100 ml THF and a solution of 2.86 ml (30.0 mmol) 2-amino-2-methyl-propan-1-ol in 25 ml THF is added dropwise. The mixture is stirred for 2 hours at ambient temperature and then evaporated down i. vac. The residue is further reacted without any more purification.

Yield: 8.40 g (quant.)
$C_{14}H_{20}N_2O_4$ (280.32)
Mass spectrum: $(M-H)^-=279$
$R_f$ value: 0.20 (silica gel; dichloromethane/ethanol=19:1)

(b) methyl 4-(4,4-dimethyl-2-oxo-imidazolidin-1-yl)-3-methyl-benzoate 7.00 g (25.0 mmol) methyl 4-(3-[1,1-dimethyl-2-hydroxy-ethyl]-ureido)-3-methyl-benzoate are dissolved in 400 ml THF at 0° C. and combined with 6.73 g (60.0 mmol) potassium-tert.-butoxide. After stirring for 15 minutes at 0° C. a solution of 5.72 g (30.0 mmol) p-toluenesulphonic acid in 50 ml THF is added dropwise. After another 10 minutes stirring at 0° C. 300 ml of water are added, the mixture is neutralised with 1-molar hydrochloric acid and the THF is removed i. vac. The residue is extracted with dichloromethane. The combined organic phases are dried over sodium sulphate and evaporated down i. vac. Then the residue is purified by chromatography on silica gel (eluting gradient: dichloromethane/ethanol=100:0->97:3).

Yield: 2.50 g (38%)
C$_{14}$H$_{18}$N$_2$O$_3$ (262.30)
Mass spectrum: (M+H)$^+$=263
R$_f$ value: 0.30 (silica gel; dichloromethane/ethanol=19:1)

(c) 4-(4,4-dimethyl-2-oxo-imidazolidin-1-yl)-3-methyl-benzoic acid 2.70 g (10.3 mmol) methyl 4-(4,4-dimethyl-2-oxo-imidazolidin-1-yl)-3-methyl-benzoate are suspended in 75 ml of methanol and combined with a solution of 1.68 g (30.0 mmol) potassium hydroxide in 10 ml of water. It is stirred for 3 hours at ambient temperature and then evaporated down i. vac. The aqueous residue is diluted with water, acidified with 1-molar hydrochloric acid and the precipitate obtained is suction filtered, washed with water and dried.

Yield: 2.30 g (90%)
C$_{13}$H$_{16}$N$_2$O$_3$ (248.28)
Mass spectrum: (M+H)$^+$=249
R$_f$ value: 0.50 (silica gel; dichloromethane/methanol=9:1)

(d) N-[(1S)-1-(5-chloro-1H-benzimidazol-2-yl)-ethyl]-3-methyl-4-([1,3]oxazepan-2-on-3-yl)-benzamide Prepared analogously to Example 1f from 4-(4,4-dimethyl-2-oxo-imidazolidin-1-yl)-3-methyl-benzoic acid, (1S)-1-(5-chloro-1H-benzimidazol-2-yl)-ethylamine, TBTU and DIPEA in THF and purification of the residue by chromatography on silica gel.

Yield: 59%
C$_{22}$H$_{24}$ClN$_5$O$_2$ (425.91)
Mass spectrum: (M+H)$^+$=426/428 (chlorine isotope)
R$_f$ value: 0.40 (silica gel; dichloromethane/methanol=9:1)
The following compound is prepared analogously:

Example 93

3-chloro-N-[(1S)-1-(5-chloro-1H-benzimidazol-2-yl)-ethyl]-4-(4-methyl-2-oxo-oxazolidin-3-yl)-benzamide

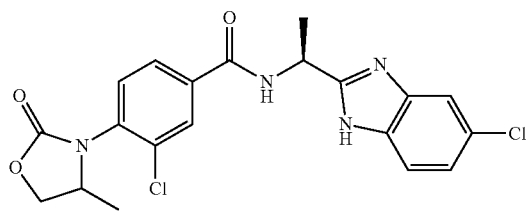 [SMILES: CC1COC(=O)N1c1ccc(C(=O)N[C@@H](C)c2nc3cc(Cl)ccc3[nH]2)cc1Cl]

(a) 3-chloro-4-(2-hydroxy-1-methyl-ethylamino)-benzonitrile 4.00 g (25.7 mmol) 3-chloro-4-fluoro-benzonitrile are heated to 60° C. in 20 ml DMSO with 8.00 g (106.5 mmol) 2-amino-1-propanol with stirring for 2 hours. Then the reaction mixture is poured into water and extracted with ethyl acetate. The combined organic phases are washed with water and sat. sodium chloride solution, dried over sodium sulphate and evaporated down i. vac.

Yield: 5.20 g (96%)
C$_{10}$H$_{11}$ClN$_2$O (210.66)
Mass spectrum: (M+H)$^+$=211/213 (chlorine isotope)
R$_f$ value: 0.27 (silica gel; dichloromethane/methanol=19:1)

| No. | structural formula / Name | Yield | mass peak(s) | R$_f$ value |
|---|---|---|---|---|
| 92 | N-[(1R)-1-(5-chloro-1H-benzimidazol-2-yl)-2-methoxy-ethyl]-4-(4,4-dimethyl-2-oxo-imidazolidin-1-yl)-3-methyl-benzamide | Σ: 29% | (M + H)$^+$ = 456/458 (chlorine isotope) | 0.45 (silica gel, CH$_2$Cl$_2$/C$_2$H$_5$OH 9:1) |

(b) 3-chloro-4-(2-hydroxy-1-methyl-ethylamino)-benzoic acid 5.20 g (24.7 mmol) 3-chloro-4-(2-hydroxy-1-methyl-ethylamino)-benzonitrile are refluxed for 6 hours in 50 ml of conc. hydrochloric acid with stirring. Then the mixture is evaporated down i. vac., made basic with conc. ammonia solution and extracted with ethyl acetate. After acidification of the aqueous phase with acetic acid the mixture is extracted with ethyl acetate, the combined organic phases are washed with water and sat. sodium chloride solution, dried over sodium sulphate and evaporated down i. vac.

Yield: 5.00 g (88%)
$C_{10}H_{12}ClNO_3$ (229.66)
Mass spectrum: $(M+H)^+$=230/232 (chlorine isotope)
$R_f$ value: 0.44 (silica gel; dichloromethane/methanol=9:1)

(c) ethyl 3-chloro-4-(2-hydroxy-1-methyl-ethylamino)-benzoate 5.00 g (21.8 mmol) 3-chloro-4-(2-hydroxy-1-methyl-ethylamino)-benzoic acid are stirred for 16 hours in 100 ml sat. ethanolic hydrochloric acid at ambient temperature and then evaporated down i. vac. The residue is combined with water and conc. ammonia solution and extracted with ethyl acetate. The combined organic phases are washed with water and sat. sodium chloride solution, dried over sodium sulphate and evaporated down i. vac. The residue is purified by chromatography on silica gel (eluant: dichloromethane/methanol=50:1).

Yield: 3.40 g (61%)
$C_{12}H_{16}ClNO_3$ (257.71)
Mass spectrum: $(M+H)^+$=258/260 (chlorine isotope)
$R_f$ value: 0.34 (silica gel; dichloromethane/methanol=19:1)

(d) ethyl 3-chloro-4-(4-methyl-2-oxo-oxazolidin-3-yl)-benzoate 0.50 g (1.94 mmol) ethyl 3-chloro-4-(2-hydroxy-1-methyl-ethylamino)-benzoate are placed in 30 ml THF together with 0.22 g (2.20 mmol) triethylamine and 1.10 ml (2.08 mmol) 20% phosgene solution in toluene is added with stirring at ambient temperature. The mixture is stirred for 1 hour at ambient temperature, then 1 ml of water is added and the mixture is stirred for another 10 minutes. The mixture is then evaporated down i. vac., combined with water and extracted with ethyl acetate. The combined organic phases are washed with water and sat. sodium chloride solution, dried over sodium sulphate and evaporated down i. vac.

Yield: 0.54 g (98%)
$C_{13}H_{14}ClNO_4$ (283.71)
Mass spectrum: $(M+H)^+$=284/286 (chlorine isotope)
$R_f$ value: 0.71 (silica gel; dichloromethane/methanol=19:1)

(e) 3-chloro-4-(4-methyl-2-oxo-oxazolidin-3-yl)-benzoic acid 0.90 g (3.17 mmol) ethyl 3-chloro-4-(4-methyl-2-oxo-oxazolidin-3-yl)-benzoate are stirred for 1 hour in 50 ml of methanol with 10 ml 1-molar aqueous lithium hydroxide solution at ambient temperature. The mixture is then evaporated down to 20 ml i. vac., acidified with conc. hydrochloric acid and extracted with ethyl acetate. The combined organic phases are washed with sat. sodium chloride solution, dried over sodium sulphate and evaporated down i. vac. The residue is crystallised from a little diethyl ether and suction filtered.

Yield: 0.45 g (56%)
$C_{11}H_{10}ClNO_4$ (255.65)
Mass spectrum: $(M+H)^+$=256/258 (chlorine isotope)
$R_f$ value: 0.26 (silica gel; dichloromethane/methanol=9:1)

(f) 3-chloro-N-[(1S)-1-(5-chloro-1H-benzimidazol-2-yl)-ethyl]-4-(4-methyl-2-oxo-oxazolidin-3-yl)-benzamide Prepared analogously to Example 1f from 3-chloro-(4-methyl-2-oxo-oxazolidin-3-yl)-benzoic acid, (1S)-1-(5-chloro-1H-benzimidazol-2-yl)-ethylamine, TBTU and DIPEA in THF and purification of the residue by chromatography on aluminium oxide.

Yield: 45%
$C_{20}H_{18}Cl_2N_4O_3$ (433.29)
Mass spectrum: $(M+H)^+$=433/435/437 (chlorine isotope)
$R_f$ value: 0.65 (silica gel; dichloromethane/methanol=9:1)
The following compounds were prepared analogously:

| No. | structural formula / Name | Yield | mass peak(s) | $R_f$ value or $R_t$ |
|---|---|---|---|---|
| 94 | 3-chloro-N-[(1R)-1-(5-chloro-1H-benzimidazol-2-yl)-2-methoxy-ethyl]-4-(4-methyl-2-oxo-oxazolidin-3-yl)-benzamide | Σ: 18% | $(M+H)^+$ = 463/465/467 (chlorine isotope) | 0.60 (silica gel, $CH_2Cl_2$/$CH_3OH$ 19:1) |

-continued

| No. | structural formula / Name | Yield | mass peak(s) | $R_f$-value or $R_t$ |
|---|---|---|---|---|
| 102 | N-[(1R)-1-(5-chloro-1H-benzimidazol-2-yl)-2-methoxy-ethyl]-3-methyl-4-((4S)-4-methyl-2-oxo-oxazolidin-3-yl)-benzamide | Σ: 18% | $(M + H)^+$ = 443/445 (chlorine isotope) | 0.20 (silica gel, $CH_2Cl_2$/ $CH_3OH$ 19:1) |
| 103 | 3-chloro-N-[(1R)-1-(5-chloro-1H-benzimidazol-2-yl)-2-methoxy-ethyl]-4-(4,4-dimethyl-2-oxo-oxazolidin-3-yl)-benzamide | Σ: 9.4% | $(M + H)^+$ = 477/479/481 (chlorine isotope) | 0.30 (silica gel, $CH_2Cl_2$/ $CH_3OH$ 19:1) |
| 104 | N-[(1R)-1-(5-chloro-1H-benzimidazol-2-yl)-2-methoxy-ethyl]-3-methyl-4-((4R)-4-methyl-2-oxo-oxazolidin-3-yl)-benzamide | Σ: 13% | $(M + H)^+$ = 443/445 (chlorine isotope) | 0.80 (silica gel, $CH_2Cl_2$/ $CH_3OH$ 19:1) |
| 105 | 3-chloro-N-[(1R)-1-(5-chloro-1H-benzimidazol-2-yl)-2-methoxy-ethyl]-4-((4R)-4-ethyl-2-oxo-oxazolidin-3-yl)-benzamide | Σ: 18% | $(M + H)^+$ = 477/479/481 (chlorine isotope) | 0.65 (silica gel, $CH_2Cl_2$/ $CH_3OH$ 19:1) |

Example 95

N-[1-(5-chloro-1H-benzimidazol-2-yl)-1-phenyl-methyl]-3-methyl-4-(morpholin-3-on-4-yl)-benzamide

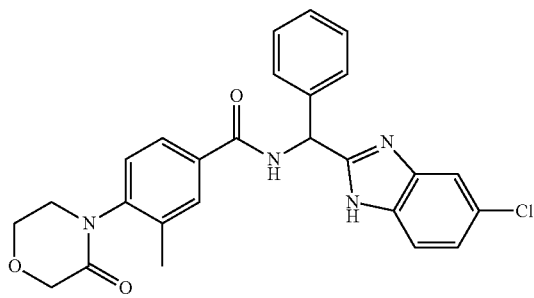 [SMILES: Cc1cc(C(=O)NC(c2ccccc2)c2nc3cc(Cl)ccc3[nH]2)ccc1N1CCOCC1=O]

(a) N'-(2-amino-4-chloro-phenyl)-N-Boc-phenyl-glycinamide and N'-(2-amino-5-chloro-phenyl)-N-Boc-phenyl-glycinamide Prepared analogously to Example 47a from N-Boc-phenyl-glycine, 4-chloro-1,2-phenylenediamine and DCC in THF.

Yield: quant. mixture of the two regioisomers
$C_{19}H_{22}ClN_3O_3$ (375.85)
Mass spectrum: $(M+H)^+=376/378$ (chlorine isotope)
$R_f$ value: 0.41 (silica gel; dichloromethane/ethanol=19:1)

(b) N-acetyl-1-(5-chloro-1H-benzimidazol-2-yl)-1-phenyl-methylamine 3.65 g (9.71 mmol) of the mixture obtained in 95a are dissolved in 8 ml acetic acid and refluxed for 6 hours with stirring. The reaction mixture is evaporated down i. vac. and the residue is purified by chromatography on silica gel (eluting gradient: dichloromethane/ethanol=100:0->94:6).

Yield: 1.34 g (46%)
$C_{16}H_{14}ClN_3O$ (299.76)
Mass spectrum: $(M+H)^+=300/302$ (chlorine isotope)
$R_f$ value: 0.19 (silica gel; dichloromethane/ethanol=19:1)

(c) 1-(5-chloro-1H-benzimidazol-2-yl)-1-phenyl-methylamine 1.34 g (4.47 mmol) N-acetyl-1-(5-chloro-1H-benzimidazol-2-yl)-1-phenyl-methylamine in 9 ml of ethanol are combined with 18 ml of conc. hydrochloric acid and heated to 50° C. for 2 days. The reaction mixture is evaporated down i. vac. and twice taken up in ethanol and evaporated down again.

Yield: 1.26 g (96%)
$C_{14}H_{12}ClN_3 \cdot HCl$ (294.18/257.72)
Mass spectrum: $(M+H)^+=258/260$ (chlorine isotope)

(d) N-[1-(5-chloro-1H-benzimidazol-2-yl)-1-phenyl-methyl]-3-methyl-4-(morpholin-3-on-4-yl)-benzamide Prepared analogously to Example 1f from 3-methyl-4-(morpholin-3-on-4-yl)-benzoic acid, 1-(5-chloro-1H-benzimidazol-2-yl)-1-phenyl-methylamine, TBTU and DIPEA in THF.

Yield: 89%
$C_{26}H_{23}ClN_4O_3$ (474.94)
Mass spectrum: $(M+H)^+=475/477$ (chlorine isotope)
$R_f$ value: 0.68 (silica gel; dichloromethane/ethanol=9:1)

The following compound is prepared analogously:

| No. | structural formula / Name | Yield | mass peak(s) | $R_f$ value or $R_t$ |
|---|---|---|---|---|
| 108 | N-[1-(1S)-(5-chloro-1H-benzimidazol-2-yl)-2-cyano-ethyl]-3-methyl-4-(morpholin-3-on-4-yl)-benzamide | Σ: 12% | $(M+H)^+=$ 437/439 (chlorine isotope) | 0.51 (silica gel, $CH_2Cl_2$/ethanol = 9:1) |
| 140 | N-[1-(5-chloro-1H-benzimidazol-2-yl)-3-methyl-butyl]-3-methyl-4-(morpholin-3-on-4-yl)-benzamide | Σ: 2.9% | $(M+H)^+=$ 455/457 (chlorine isotope) | 0.60 (silica gel, $CH_2Cl_2$/$C_2H_5OH$ 9:1) |

Example 96

N-[(1S)-1-(5-chloro-1H-benzimidazol-2-yl)-propyl]-3-methyl-4-(morpholin-3-on-4-yl)-benzamide

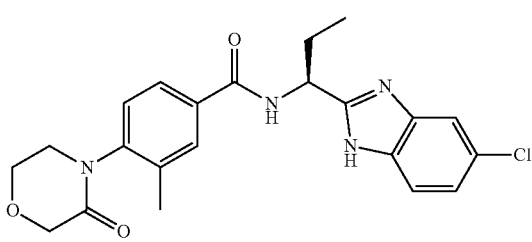 [SMILES: CC[C@H](NC(=O)c1ccc(N2CCOCC2=O)c(C)c1)c1nc2cc(Cl)ccc2[nH]1]

(a) N'-(2-amino-4-chloro-phenyl)-(2S)-2-(Boc-amino)-butyric acid amide and N'-(2-amino-5-chloro-phenyl)-(2S)-2-(Boc-amino)-butyric acid amide Prepared analogously to Example 47a from (2S)-2-(Boc-amino)-butyric acid, 4-chloro-1,2-phenylenediamine and DCC in THF.
Yield: 89% mixture of the two regioisomers
$C_{15}H_{22}ClN_3O_3$ (327.81)
Mass spectrum: $(M+H)^+=328/330$ (chlorine isotope)
$R_f$ value: 0.63 (silica gel; dichloromethane/ethanol=19:1)

(b) (1S)-N-Boc-1-(5-chloro-1H-benzimidazol-2-yl)-propylamine

Prepared analogously to Example 47b from the mixture obtained in 95a and acetic acid and purification of the residue by chromatography on silica gel.
Yield: 94%
$C_{15}H_{20}ClN_3O_2$ (309.79)
Mass spectrum: $(M+H)^+=310/312$ (chlorine isotope)
$R_f$ value: 0.63 (silica gel; dichloromethane/ethanol=19:1)

(c) (1S)-1-(5-chloro-1H-benzimidazol-2-yl)-1-phenyl-methylamine

Prepared analogously to Example 75c from (1S)-N-Boc-1-(5-chloro-1H-benzimidazol-2-yl)-propylamine and trifluoroacetic acid in dichloromethane.
Yield: quant.
$C_{10}H_{12}ClN_3 \cdot 2\ CF_3COOH$ (437.72/209.68)
Mass spectrum: $(M+H)^+=210/212$ (chlorine isotope)

(d) N-[(1S)-1-(5-chloro-1H-benzimidazol-2-yl)-propyl]-3-methyl-4-(morpholin-3-on-4-yl)-benzamide Prepared analogously to Example 1f from 3-methyl-4-(morpholin-3-on-4-yl)-benzoic acid, (1S)-1-(5-chloro-1H-benzimidazol-2-yl)-propylamine, TBTU and DIPEA in THF.
Yield: 17%
$C_{22}H_{23}ClN_4O_3$ (426.90)
Mass spectrum: $(M+H)^+=427/429$ (chlorine isotope)
$R_f$ value: 0.45 (silica gel; dichloromethane/ethanol=9:1)
The following compounds were prepared analogously:

| No. | structural formula / Name | Yield | mass peak(s) | $R_f$ value or $R_t$ |
|---|---|---|---|---|
| 107 | N-[1-(5-chloro-1H-benzimidazol-2-yl)-1-(1H-pyrazol-3-yl)-methyl]-3-methyl-4-(morpholin-3-on-4-yl)-benzamide | Σ: 4.0% | $(M+H)^+$ = 465/467 (chlorine isotope) | 0.15 (silica gel, $CH_2Cl_2$/ $CH_3OH$ 9:1) |
| 141 | N-[(1R)-1-(5-chloro-1H-benzimidazol-2-yl)-2-benzyloxy-ethyl]-3-methyl-4-(morpholin-3-on-4-yl)-benzamide | Σ: 62% | $(M-H)^-$ = 519/521 (chlorine isotope) | 0.54 (silica gel, $CH_2Cl_2$/ $C_2H_5OH$ 9:1) |

-continued

| No. | structural formula Name | Yield | mass peak(s) | $R_f$ value or $R_t$ |
|---|---|---|---|---|
| 149 | N-[3-(5-chloro-1H-benzimidazol-2-yl)-tetrahydrofuran-3-yl]-3-methyl-4-(morpholin-3-on-4-yl)-benzamide | Σ: 54% | (M − H)⁻ = 453/455 (chlorine isotope) | 0.55 (silica gel, $CH_2Cl_2$/ $C_2H_5OH$ 9:1) |

Example 106

N-[(1R)-1-(5-chloro-1H-benzimidazol-2-yl)-2-methoxy-ethyl]-3-fluoro-4-(morpholin-3-on-4-yl)-benzamide

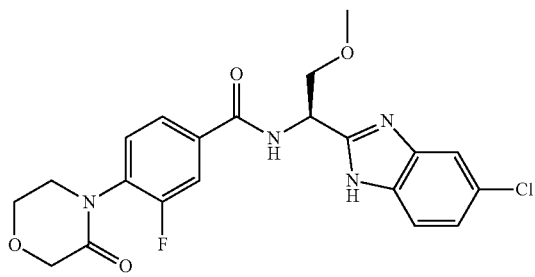

(a) ethyl 4-[(2-chloro-ethoxy)-acetyl-amino]-3-fluoro-benzoate

Prepared analogously to Example 46a from (2-chloro-ethoxy)-acetylchloride and ethyl 4-amino-3-fluoro-benzoate with TEA in THF.
Yield: 44%
$C_{13}H_{15}ClFNO_4$ (303.71)
Mass spectrum: (M+H)⁺=304/306 (chlorine isotope)
$R_f$ value: 0.29 (silica gel; dichloromethane)

(b) 4-(2-carboxymethoxy-ethylamino)-3-fluoro-benzoic acid 580 mg (1.91 mmol) ethyl 4-[(2-chloro-ethoxy)-acetyl-amino]-3-fluoro-benzoate in 6 ml dioxane are combined with 3.82 ml (7.64 mmol) 2-molar potassium hydroxide solution and 2 ml of water. Then the mixture is heated to 70° C. for 2 h, then diluted with water and acidified with 6-molar hydrochloric acid. After the addition of dichloromethane the precipitate formed is suction filtered and dried in the drying cupboard at 50° C.
Yield: 390 mg (79%)
$C_{11}H_{12}FNO_5$ (257.22)
Mass spectrum: (M+H)⁺=258
$R_f$ value: 0.66 (reversed phase RP-8; methanol/5% NaCl solution=6:4)

(c) 3-fluoro-4-(morpholin-3-on-4-yl)-benzoic acid-chloride

Prepared analogously to Example 41c from 4-(2-carboxymethoxy-ethylamino)-3-fluoro-benzoic acid and thionylchloride in dichloromethane with DMF.
Yield: quant.
$C_{11}H_9ClFNO_3$ (257.65)

(d) N-[(1R)-1-(5-chloro-1H-benzimidazol-2-yl)-2-methoxy-ethyl]-3-fluoro-4-(morpholin-3-on-4-yl)-benzamide Prepared analogously to Example 41d from 3-fluoro-4-(morpholin-3-on-4-yl)-benzoic acid-chloride and (1R)-1-(5-chloro-1H-benzimidazol-2-yl)-2-methoxy-ethylamine with TEA in THF.
Yield: 47%
$C_{21}H_{20}ClFN_4O_4$ (446.86)
Mass spectrum: (M+H)⁺=447/449 (chlorine isotope)
$R_f$ value: 0.40 (silica gel; dichloromethane/ethanol=9:1)

Example 109

N-[1-(5-chloro-1H-benzimidazol-2-yl)-1-(pyridin-3-yl)-methyl]-3-methyl-4-(morpholin-3-on-4-yl)-benzamide

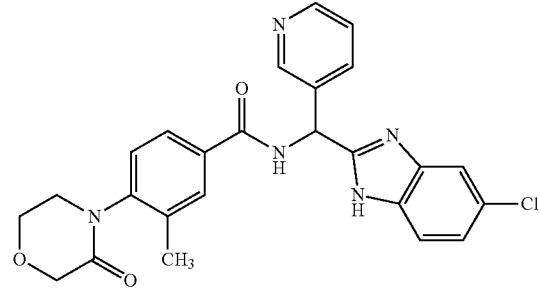 [SMILES: Cc1cc(C(=O)NC(c2cccnc2)c2nc3cc(Cl)ccc3[nH]2)ccc1N1CCOCC1=O]

(a) N'-(2-amino-4-chloro-phenyl)-2-(Boc-amino)-2-(pyridin-3-yl)-acetic acid amide and N'-(2-amino-5-chloro-phenyl)-2-(Boc-amino)-2-(pyridin-3-yl)-acetic acid amide 1.00 g (3.96 mmol) N-Boc-amino-2-(pyridin-3-yl)-acetic acid are placed together with 0.59 g (4.16 mmol) 4-chloro-1, 2-phenylenediamine at 0° C. in 20 ml THF and 2.92 ml (4.96 mmol) 50% PPA solution in ethyl acetate and 1.24 ml (8.92 mmol) TEA are added. After stirring for 30 min at 0° C. the mixture is stirred for 5 h at ambient temperature stirred and then evaporated down completely i. vac. The residue is purified by chromatography on silica gel (eluting gradient: dichloromethane/ethanol=10:0->9:1).

Yield: 1.32 g (88%) mixture of the two regioisomers
$C_{18}H_{21}ClN_4O_3$ (376.84)
Mass spectrum: $(M+H)^+$=377/379 (chlorine isotope)
$R_f$ value: 0.40 (silica gel; dichloromethane/ethanol=9:1)

(b) N-Boc-1-(5-chloro-1H-benzimidazol-2-yl)-1-(pyridin-3-yl)-methylamine

Prepared analogously to Example 47b from the product obtained in Example 111a and acetic acid.
Yield: 81%
$C_{18}H_{19}ClN_4O_2$ (358.82)
Mass spectrum: $(M+H)^+$=359/361 (chlorine isotope)
$R_f$ value: 0.51 (silica gel; dichloromethane/ethanol=9:1)

(c) 1-(5-chloro-1H-benzimidazol-2-yl)-1-(pyridin-3-yl)-methylamine

Prepared analogously to Example 1g from N-Boc-1-(5-chloro-1H-benzimidazol-2-yl)-1-(pyridin-3-yl)-methylamine and trifluoroacetic acid in dichloromethane.
Yield: 66%
$C_{13}H_{11}ClN_4$ (258.71)
Mass spectrum: $(M+H)^+$=259/261 (chlorine isotope)
$R_f$ value: 0.62 (silica gel; dichloromethane/ethanol=9:1)

(d) N-[1-(5-chloro-1H-benzimidazol-2-yl)-1-(pyridin-3-yl)-methyl]-3-methyl-4-(morpholin-3-on-4-yl)-benzamide Prepared analogously to Example 1f from 3-methyl-4-(morpholin-3-on-4-yl)-benzoic acid and 1-(5-chloro-1H-benzimidazol-2-yl)-1-(pyridin-3-yl)-methylamine with TBTU and DIPEA in THF.
Yield: 84%
$C_{25}H_{22}ClN_5O_3$ (475.93)
Mass spectrum: $(M+H)^+$=476/478 (chlorine isotope)
$R_f$ value: 0.31 (silica gel; dichloromethane/ethanol=9:1)

Example 110

N-[1-(5-chloro-1H-benzimidazol-2-yl)-1-(1-methyl-pyrazol-3-yl)-methyl]-3-methyl-4-(morpholin-3-on-4-yl)-benzamide

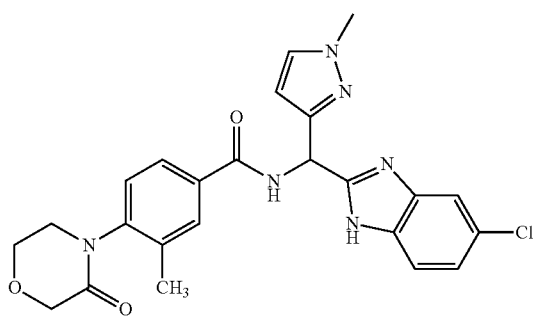 [SMILES: Cc1cc(C(=O)NC(c2ccn(C)n2)c2nc3cc(Cl)ccc3[nH]2)ccc1N1CCOCC1=O]

(a) methyl ethoxycarbonyl-methoxyimino-(1-methyl-pyrazol-3-yl)-acetate 5.00 g (20.7 mmol) ethoxycarbonyl-methoxyimino-(pyrazol-3-yl)-acetic acid are placed in 20 ml DMF together with 5.73 g (41.5 mmol) potassium carbonate at ambient temperature, stirred until the development of gas has ended, then 2.58 ml (41.5 mmol) of methyl iodide are added and the mixture is stirred for 2 h at 50° C. After evaporation of the reaction mixture i. vac. the residue is combined with water and ethyl acetate, the organic phase is washed with water, dried over magnesium sulphate and evaporated down completely i. vac. The residue is purified by chromatography on silica gel (eluting gradient: petroleum ether/ethyl acetate=80:20->65:35).

Yield: 2.61 g (26%) in admixture with regioisomers
$C_{11}H_{15}N_3O_5$ (269.25)
Mass spectrum: $(M+H)^+$=270
$R_f$ value: 0.25 (silica gel; petroleum ether/ethyl acetate=1:1)

(b) methyl 2-amino-2-(1-methyl-pyrazol-3-yl)-acetate 2.61 g (9.69 mmol) methyl ethoxycarbonyl-methoxyimino-(1-methyl-pyrazol-3-yl)-acetate are hydrogenated in 60 ml of ethanol with 1.1 g 5% palladium charcoal for 16 h at 50° C. under 3.4 bars pressure in a hydrogen atmosphere. Then the mixture is suction filtered and the filtrate is evaporated down completely i. vac.

Yield: 1.90 g (quant.), slightly contaminated
$C_7H_{11}N_3O_2$ (169.18)
Mass spectrum: $(M+H)^+$=170
$R_f$ value: 0.30 (silica gel; dichloromethane/ethanol=9:1)

(c) methyl N-Boc-2-amino-2-(1-methyl-pyrazol-3-yl)-acetate

Prepared analogously to Example 1d from methyl 2-amino-2-(1-methyl-pyrazol-3-yl)-acetate and di-tert. butyl pyrocarbonate with TEA in dichloromethane.
Yield: 81%
$C_{12}H_{19}N_3O_4$ (269.30)
Mass spectrum: $(M+H)^+$=270

(d) N-Boc-2-amino-2-(1-methyl-pyrazol-3-yl)-acetic acid 1.16 g (4.31 mmol) methyl N-Boc-2-amino-2-(1-methyl-pyrazol-3-yl)-acetate in 16 ml THF are combined with 10 ml of water and 10 ml of 1-molar lithium hydroxide solution are added. After stirring at ambient temperature for 2 h the mixture is evaporated down i. vac., the residue is combined with water, filtered and the filtrate is adjusted to pH 5 with potassium hydrogen sulphate solution. After total evaporation i. vac. the residue is treated with dichloromethane and a little ethanol, suction filtered and the filtrate is evaporated down completely i. vac.

Yield: 0.92 g (84%)
$C_{11}H_{17}N_3O_4$ (255.27)
Mass spectrum: $(M+H)^+$=256
$R_f$ value: 0.15 (silica gel; dichloromethane/ethanol=8:2)

(e) N'-(2-amino-4-chloro-phenyl)-2-(Boc-amino)-2-(1-methyl-pyrazol-3-yl)-acetic acid amide and N'-(2-amino-5-chloro-phenyl)-2-(Boc-amino)-2-(1-methyl-pyrazol-3-yl)-acetic acid amide Prepared analogously to Example 111a from N-Boc-2-amino-2-(1-methyl-pyrazol-3-yl)-acetic acid and 4-chloro-1,2-phenylenediamine with PPA in ethyl acetate and NMM in dichloromethane.

Yield: 55% mixture of the two regioisomers $C_{17}H_{22}ClN_5O_3$ (379.84)

$R_f$ value: 0.61 (silica gel; dichloromethane/ethanol=9:1)

(f) N-Boc-1-(5-chloro-1H-benzimidazol-2-yl)-1-(1-methyl-pyrazol-3-yl)-methylamine Prepared analogously to Example 47b from the product obtained in Example 112e and acetic acid.

Yield: 81%

$C_{17}H_{20}ClN_5O_2$ (361.83)

Mass spectrum: $(M+H)^+=362/364$ (chlorine isotope)

$R_f$ value: 0.60 (silica gel; dichloromethane/ethanol=9:1)

(g) 1-(5-chloro-1H-benzimidazol-2-yl)-1-(1-methyl-pyrazol-3-yl)-methylamine

Prepared analogously to Example 1g from N-Boc-1-(5-chloro-1H-benzimidazol-2-yl)-1-(1-methyl-pyrazol-3-yl)-methylamine and trifluoroacetic acid in dichloromethane.

Yield: 77%

$C_{12}H_{12}ClN_5$ (261.71)

Mass spectrum: $(M-NH_3+H)^+=245/247$ (chlorine isotope)

$R_f$ value: 0.30 (silica gel; dichloromethane/ethanol/conc. ammonia solution=9:1:0.1)

(h) N-[1-(5-chloro-1H-benzimidazol-2-yl)-1-(1-methyl-pyrazol-3-yl)-methyl]-3-methyl-4-(morpholin-3-on-4-yl)-benzamide Prepared analogously to Example 1f from 3-methyl-4-(morpholin-3-on-4-yl)-benzoic acid and 1-(5-chloro-1H-benzimidazol-2-yl)-1-(1-methyl-pyrazol-3-yl)-methylamine with TBTU and DIPEA in THF.

Yield: 38%

$C_{24}H_{23}ClN_6O_3$ (478.93)

Mass spectrum: $(M+H)^+=479/481$ (chlorine isotope)

$R_f$ value: 0.50 (silica gel; dichloromethane/ethanol=9:1)

Example 111

3-chloro-N-[(1R)-1-(5-chloro-1H-benzimidazol-2-yl)-2-methoxy-ethyl]-4-(5-methyl-morpholin-3-on-4-yl)-benzamide

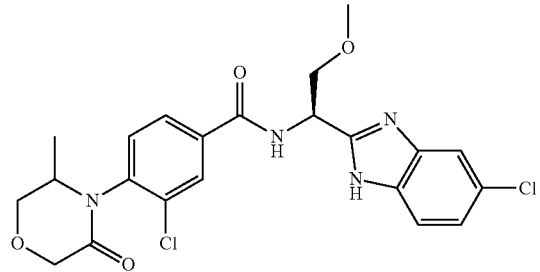 [SMILES: COC[C@H](NC(=O)c1ccc(N2C(=O)COCC2C)c(Cl)c1)c1nc2cc(Cl)ccc2[nH]1]

(a) ethyl 4[2-(tert.-butoxycarbonyl-methoxy)-1-methyl-ethylamino]-3-chloro-benzoate 1.12 g (4.35 mmol) ethyl 3-chloro-4-(2-hydroxy-1-methyl-ethylamino)-benzoate are combined in 10 ml DMF with 0.21 g (4.78 mmol) 55% sodium hydride dispersion and stirred for 5 min at ambient temperature. Then 0.67 ml tert.-butyl bromoacetate are added and the mixture is stirred for a further 16 h at ambient temperature. Then the reaction mixture is poured into water and extracted with ethyl acetate. The combined organic phases are washed with water and sat. sodium chloride solution, dried over sodium sulphate and evaporated down completely i. vac. The residue is purified by chromatography on silica gel (eluting gradient: petroleum ether/ethyl acetate=95:5->80:20)

Yield: 230 mg (14%)

$C_{18}H_{26}ClNO_5$ (371.86)

Mass spectrum: $(M+H)^+=372/374$ (chlorine isotope)

$R_f$ value: 0.65 (silica gel; petroleum ether/ethyl acetate=7:3)

(b) ethyl 3-chloro-4-[2-(hydroxycarbonyl-methoxy)-1-methyl-ethylamino]-benzoate Prepared analogously to Example 1g from ethyl 4[2-(tert.-butoxycarbonyl-methoxy)-1-methyl-ethylamino]-3-chloro-benzoate and trifluoroacetic acid in dichloromethane.

Yield: 87%

$C_{14}H_{18}ClNO_5$ (315.75)

Mass spectrum: $(M+H)^+=316/318$ $R_f$ value: 0.40 (silica gel; dichloromethane/ethanol=9:1)

(c) ethyl 3-chloro-4-(5-methyl-momholin-3-on-4-yl)-benzoate

Prepared analogously to Example 41c from ethyl 3-chloro-4-[2-(hydroxycarbonyl-methoxy)-1-methyl-ethylamino]-benzoate and thionyl chloride with DMF in dichloromethane.

Yield: 69% (contaminated)

$C_{14}H_{16}ClNO_4$ (297.73)

Mass spectrum: $(M+H)^+=298/300$ (chlorine isotope)

$R_f$ value: 0.40 (silica gel; dichloromethane/ethanol=19:1)

(d) 3-chloro-4-(5-methyl-morpholin-3-on-4-yl)-benzoic acid

Prepared analogously to Example 31b from ethyl 3-chloro-4-(5-methyl-morpholin-3-on-4-yl)-benzoate with lithium hydroxide in THF and water.
Yield: 91%
$C_{12}H_{12}ClNO_4$ (269.68)
$R_f$ value: 0.30 (silica gel; dichloromethane/ethanol=9:1)

(e) 3-chloro-N-[(1R)-1-(5-chloro-1H-benzimidazol-2-yl)-2-methoxy-ethyl]-4-(5-methyl-morpholin-3-on-4-yl)-benzamide Prepared analogously to Example 1f from 3-chloro-4-(5-methyl-morpholin-3-on-4-yl)-benzoic acid and (1R)-1-(5-chloro-1H-benzimidazol-2-yl)-2-methoxy-ethylamine with TBTU and TEA in DMF.
Yield: 28%
$C_{22}H_{22}Cl_2N_4O_4$ (477.34)
Mass spectrum: $(M-H)^-$=475/477/479 (chlorine isotope)
$R_f$ value: 0.50 (silica gel; dichloromethane/ethanol=9:1)

Example 112

3-chloro-N-[(1S)-1-(5-chloro-1H-benzimidazol-2-yl)-ethyl]-4-(3-dimethylamino-pyrrolidin-1-yl)-benzamide

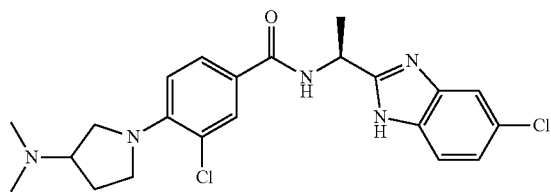 [SMILES: C[C@H](NC(=O)c1ccc(N2CCC(N(C)C)C2)c(Cl)c1)c1nc2cc(Cl)ccc2[nH]1]

(a) 3-chloro-4-(3-dimethylamino-pyrrolidin-1-yl)-benzonitrile 0.75 g (4.82 mmol) 3-chloro-4-fluoro-benzonitrile together with 0.65 ml (0.58 g, 5.06 mmol) 3-dimethylamino-pyrrolidine in 12 ml DMF are combined with 231 mg (5.30 mmol) 55% sodium hydride dispersion at ambient temperature with stirring and under an argon atmosphere. After stirring at ambient temperature for 3.5 h the reaction mixture is poured into water and extracted with ethyl acetate after thorough mixing. The combined organic phases are washed with sat. sodium chloride solution, dried over magnesium sulphate and evaporated down completely i. vac.
Yield: 1.11 g (92%)
$C_{13}H_{16}ClN_3$ (249.74)
Mass spectrum: $(M+H)^+$=250/252 (chlorine isotope)
$R_f$ value: 0.42 (silica gel; petroleum ether/ethyl acetate=1:1)

(b) 3-chloro-4-(3-dimethylamino-pyrrolidin-1-yl)-benzoic acid

Prepared analogously to Example 13b from 3-chloro-4-(3-dimethylamino-pyrrolidin-1-yl)-benzonitrile with 10-molar sodium hydroxide solution and ethanol.
Yield: 27%
$C_{13}H_{17}ClN_2O_2$ (268.74)
Mass spectrum: $(M+H)^+$=269/271 (chlorine isotope)

(c) 3-chloro-N-[(1S)-1-(5-chloro-1H-benzimidazol-2-yl)-ethyl]-4-(3-dimethylamino-pyrrolidin-1-yl)-benzamide Prepared analogously to Example 1f from 3-chloro-4-(3-dimethylamino-pyrrolidin-1-yl)-benzoic acid and (1S)-1-(5-chloro-1H-benzimidazol-2-yl)-ethylamine with TBTU and TEA in DMF.
Yield: 74%, slightly contaminated
$C_{22}H_{25}Cl_2N_5O$ (446.37)
Mass spectrum: $(M+H)^+$=446/448/450 (chlorine isotope)
$R_f$ value: 0.65 (silica gel; dichloromethane/methanol=8:2+0.5% conc. ammonia solution)

Example 113

N-[(1S)-1-(5-chloro-1H-benzimidazol-2-yl)-ethyl]-4-(pyrazolidin-3-on-1-yl)-3-trifluoromethyl-benzamide

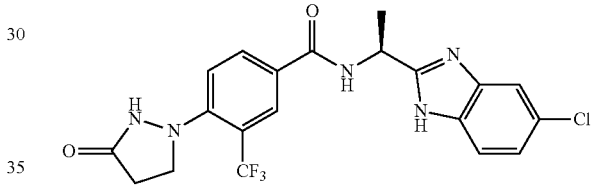

(a) 4-(pyrazolidin-3-on-1-yl)-3-trifluoromethyl-benzonitrile 1.00 g (5.29 mmol) 4-fluoro-3-trifluoromethyl-benzonitrile are stirred together with 1.35 g (12.0 mmol) potassium-tert.-butoxide in 4 ml DMSO at ambient temperature under an argon atmosphere for 35 min and then 1.00 g (8.16 mmol) pyrazolidin-3-on-hydrochloride in 3 ml DMSO are added. After stirring at ambient temperature for 68 h the reaction mixture is poured into semisat. sodium chloride solution and extracted with ethyl acetate. The combined organic phases are dried over magnesium sulphate and evaporated down completely i. vac.
Yield: 0.58 g (43%)
$C_{11}H_8F_3N_3O$ (255.20)
Mass spectrum: $(M+H)^+$=256
$R_f$ value: 0.15 (silica gel; dichloromethane+0.5% conc. ammonia solution)

(b) 4-(pyrazolidin-3-on-1-yl)-3-trifluoromethyl-benzoic acid

Prepared analogously to Example 13b from 3-chloro-4-(3-dimethylamino-pyrrolidin-1-yl)-benzonitrile with 10-molar sodium hydroxide solution and ethanol.
Yield: 56%
$C_{11}H_9F_3N_2O_3$ (274.20)

$R_f$ value: 0.60 (silica gel; dichloromethane/ethanol=8:2+ 0.5% acetic acid)

(c) N-[(1S)-1-(5-chloro-1H-benzimidazol-2-yl)-ethyl]-4-(pyrazolidin-3-on-1-yl)-3-trifluoromethyl-benzamide Prepared analogously to Example 1f from the 4-(pyrazolidin-3-on-1-yl)-3-trifluoromethyl-benzoic acid and (1S)-1-(5-chloro-1H-benzimidazol-2-yl)-ethylamine with TBTU and TEA in DMF.
Yield: 12%, contaminated
$C_{20}H_{17}ClF_3N_5O_2 \cdot 2\ CF_3COOH$ (679.88/451.83)
Mass spectrum: $(M+H)^+=452/454$ (chlorine isotope)
$R_f$ value: 0.58 (silica gel; dichloromethane/methanol=8:2+ 0.5% conc. ammonia solution)

Example 127

N-[(1S)-1-(7-chloro-imidazo[1,2a]pyridin-2-yl)-3-methyl-butyl]-3-methyl-4-(morpholin-3-on-4-yl)-benzamide

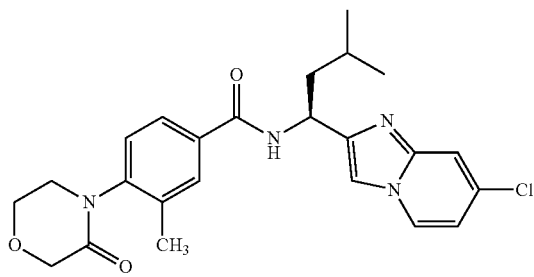 [SMILES: Cc1cc(C(=O)N[C@@H](CC(C)C)c2cn3ccc(Cl)cc3n2)ccc1N1CCOCC1=O]

(a) (1S)-N-Boc-147-chloro-imidazo[1,2a]pyridin-2-yl)-3-methyl-butylamine 1.68 g (6.37 mmol) tert.-butyl [1-(2-chloro-acetyl)-3-methyl-butyl]-carbamate in 15 ml of methanol are combined with 819 mg (6.37 mmol) 2-amino-4-chloro-pyridine at ambient temperature with stirring and the mixture is refluxed for 3 days. After evaporation i. vac. the residue is combined with 5% sodium hydrogen carbonate solution and stirred for 20 h at ambient temperature. Then it is extracted with dichloromethane, the combined organic phases are dried over sodium sulphate and evaporated down completely i. vac. The residue is purified by chromatography on silica gel (eluting gradient: dichloromethane/ethanol=100:0->94:6).
Yield: 180 mg (8%)
$C_{17}H_{24}ClN_3O_2$ (337.85)
Mass spectrum: $(M+H)^+=338/340$ (chlorine isotope)
$R_f$ value: 0.61 (silica gel; dichloromethane/ethanol=9:1)

(b) (1S)-147-chloro-imidazo[1,2a]pyridin-2-yl)-3-methyl-butylamine

Prepared analogously to Example 1g from (1S)-N-Boc-1-(7-chloro-imidazo[1,2a]pyridin-2-yl)-3-methyl-butylamine with trifluoroacetic acid in dichloromethane.
Yield: quant.
$C_{12}H_{16}ClN_3 \cdot 2\ CF_3CO_2H$ (465.78/237.73)
Mass spectrum: $(M+H)^+=238/240$ (chlorine isotope)

(c) N-[(1S)-1-(5-chloro-imidazo[1,2a]pyridin-2-yl)-3-methyl-butyl]-3-methyl-4-morpholin-3-on-4-yl)-benzamide Prepared analogously to Example 1f from 3-methyl-4-(morpholin-3-on-4-yl)-benzoic acid and (1S)-1-(5-chloro-imidazo[1,2a]pyridin-2-yl)-3-methyl-butylamine with TBTU and DIPEA in THF.
Yield: quant.
$C_{24}H_{27}ClN_4O_3$ (454.95)
Mass spectrum: $(M+H)^+=455/457$ (chlorine isotope)
$R_f$ value: 0.54 (silica gel; dichloromethane/ethanol=9:1)

The Examples that follow describe the preparation of some pharmaceutical formulations which contain as active substance any desired compound of general formula I:

Example I

Dry ampoule containing 75 mg of active substance per 10 ml
Composition:

| | |
|---|---|
| Active substance | 75.0 mg |
| Mannitol | 50.0 mg |
| water for injections | ad 10.0 ml |

Preparation:
Active substance and mannitol are dissolved in water. After packaging the solution is freeze-dried. To produce the solution ready for use for injections, the product is dissolved in water.

Example II

Dry ampoule containing 35 mg of active substance per 2 ml
Composition:

| | |
|---|---|
| Active substance | 35.0 mg |
| Mannitol | 100.0 mg |
| water for injections | ad 2.0 ml |

Preparation:
Active substance and mannitol are dissolved in water. After packaging, the solution is freeze-dried.
To produce the solution ready for use for injections, the product is dissolved in water.

Example III

Tablet containing 50 mg of active substance
Composition:

| | | |
|---|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:
(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example IV

Tablet containing 350 mg of active substance
Composition:

| | | |
|---|---|---|
| (1) Active substance | 350.0 mg | |
| (2) Lactose | 136.0 mg | |
| (3) Maize starch | 80.0 mg | |
| (4) Polyvinylpyrrolidone | 30.0 mg | |
| (5) Magnesium stearate | 4.0 mg | |
| | 600.0 mg | |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example V

Capsules containing 50 mg of active substance
Composition:

| | | |
|---|---|---|
| (1) Active substance | 50.0 mg | |
| (2) Dried maize starch | 58.0 mg | |
| (3) Powdered lactose | 50.0 mg | |
| (4) Magnesium stearate | 2.0 mg | |
| | 160.0 mg | |

Preparation:

(1) is triturated with (3). This trituration is added to the mixture of (2) and (4) with vigorous mixing.

This powder mixture is packed into size 3 hard gelatine capsules in a capsule filling machine.

Example VI

Capsules containing 350 mg of active substance
Composition:

| | | |
|---|---|---|
| (1) Active substance | 350.0 mg | |
| (2) Dried maize starch | 46.0 mg | |
| (3) Powdered lactose | 30.0 mg | |
| (4) Magnesium stearate | 4.0 mg | |
| | 430.0 mg | |

Preparation:

(1) is triturated with (3). This trituration is added to the mixture of (2) and (4) with vigorous mixing.

This powder mixture is packed into size 0 hard gelatine capsules in a capsule filling machine.

Example VII

Suppositories containing 100 mg of active substance
1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:
1. A compound of the formula

(I)

wherein
A denotes a group of the formula wherein
m denotes the number 1 or 2,
$R^{6a}$ independently of one another denotes a hydrogen, fluorine, chlorine or bromine atom or a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and
$R^{6b}$ independently of one another may be a hydrogen atom, a $C_{1-4}$-alkyl, $C_{1-4}$-alkylcarbonyl, $C_{1-4}$-alkyloxycarbonyl or $C_{1-3}$-alkylsulphonyl group, with the proviso that
in the above-mentioned substituted 7-membered groups A the heteroatoms optionally introduced as substituents are not separated from another heteroatom by precisely one carbon atom, or a group of the formula

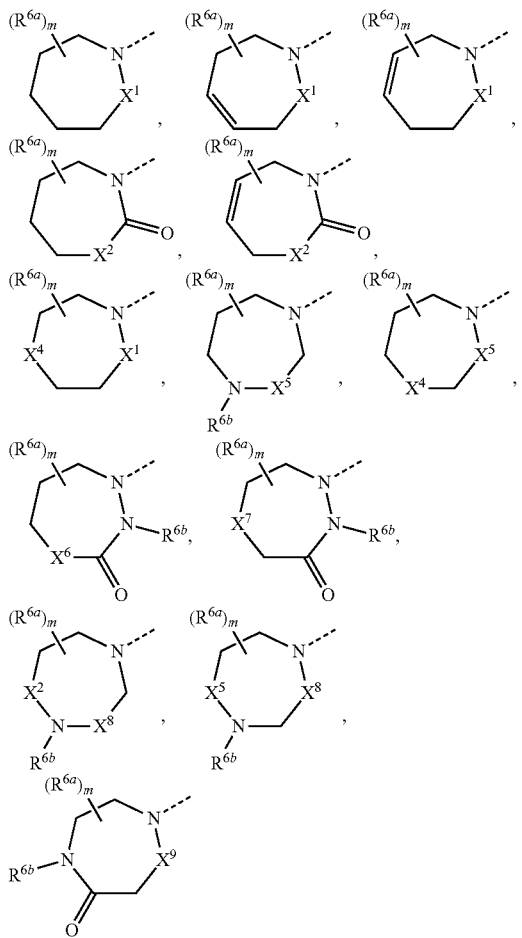

wherein
m denotes the number 1 or 2,
$X^1$ denotes an oxygen atom or a methylene, —$NR^{6b}$—, carbonyl or sulphonyl group,
$X^2$ denotes an oxygen atom or a —$NR^{6b}$ group,
$X^3$ denotes a methylene, carbonyl or sulphonyl group,
$X^4$ denotes an oxygen or sulphur atom, a —$NR^{6b}$ or carbonyl group,
$X^5$ denotes a carbonyl or sulphonyl group,
$X^6$ denotes an oxygen atom, a —$NR^{6b}$ or methylene group,
$X^7$ denotes an oxygen or sulphur atom or a —$NR^{6b}$ group,
$X^8$ denotes a methylene or carbonyl group,
$X^9$ denotes a —$NR^{6b}$ or carbonyl group,
$X^{10}$ denotes a sulphinyl or sulphonyl group and
$R^{6a}$ independently of one another denote a hydrogen, fluorine, chlorine or bromine atom or a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and
$R^{6b}$ independently of one another may be a hydrogen atom, a $C_{1-4}$-alkyl, $C_{1-4}$-alkylcarbonyl, $C_{1-4}$-alkoxycarbonyl or $C_{1-3}$-alkylsulphonyl group, with the proviso that
in the above-mentioned substituted 7-membered groups A the heteroatoms optionally introduced as substituents are not separated from another heteroatom by precisely one carbon atom, $R^1$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, nitro, amino, $C_{1-3}$-alkoxy, a mono-, di- or trifluoromethoxy group, $R^2$ denotes a hydrogen, fluorine, chlorine or bromine atom or a $C_{1-3}$-alkyl group, $R^3$ denotes a hydrogen atom, a $C_{2-3}$-alkenyl or $C_{2-3}$-alkynyl group or a straight-chain or branched $C_{1-6}$-alkyl group wherein the hydrogen atoms may be wholly or partly replaced by fluorine atoms, and which is optionally substituted by a nitrile, hydroxy, a $C_{1-5}$-alkyloxy group wherein the hydrogen atoms may be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, mercapto, $C_{1-3}$-alkylsulphanyl, $C_{1-3}$-alkylsulphinyl, $C_{1-3}$-alkylsulphonyl, $C_{1-3}$-alkylcarbonylamino-$C_{1-3}$-alkylsulphanyl, $C_{1-3}$-alkylcarbonylamino-$C_{1-3}$-alkylsulphinyl, $C_{1-3}$-alkylcarbonylamino-$C_{1-3}$-alkylsulphonyl, carboxy, $C_{1-3}$-alkyloxycarbonyl, allyloxycarbonyl, propargyloxycarbonyl, benzyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-5}$-alkylcarbonylamino, $C_{1-3}$-alkylsulphonylamino, N-($C_{1-3}$-alkylsulphonyl)-$C_{1-3}$-alkylamino, $C_{3-6}$-cycloalkylcarbonylamino, aminocarbonylamino, $C_{1-3}$-alkylaminocarbonylamino, di-($C_{1-3}$-alkyl)-aminocarbonylamino, a 4- to 7-membered cycloalkyleneiminocarbonylamino, benzyloxycarbonylamino, phenylcarbonylamino or guanidino group, a carboxy, aminocarbonyl, $C_{1-4}$-alkylaminocarbonyl, $C_{3-6}$-cycloalkylaminocarbonyl, di-($C_{1-3}$-alkyl)-aminocarbonyl, $C_{1-4}$-alkoxycarbonyl, $C_{4-6}$-cycloalkyleneiminocarbonyl group, a phenyl or heteroaryl, phenylcarbonyl-$C_{1-3}$-alkyl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, benzyloxy, carboxy-$C_{1-3}$-alkyloxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4-to 7-membered cycloalkyleneiminocarbonyl-$C_{1-3}$-alkoxy, carboxy, $C_{1-3}$-alkyloxycarbonyl or $C_{1-3}$-alkyloxy-carbonylamino group, a 3- to 7-membered cycloalkyl, cycloalkyleneimino, cycloalkyl-$C_{1-3}$-alkyl or cycloalkyleneimino-$C_{1-3}$-alkyl group wherein in the cyclic moiety a methylene group may be replaced by an —NH— group optionally substituted by a $C_{1-3}$-alkyl or $C_{1-3}$-alkylcarbonyl group or by an oxygen atom and wherein additionally a methylene group adjacent to the —NH—, —N($C_{1-3}$-alkylcarbonyl)- or —N($C_{1-3}$-alkyl)- group may be replaced in each case by a carbonyl or sulphonyl group, with the proviso that a cycloalkyleneimino group as hereinbefore defined wherein two nitrogen atoms are separated from one another by precisely one —$CH_2$— group is excluded, $R^4$ denotes a hydrogen atom or a $C_{1-3}$-alkyl group or $R^3$ and $R^4$ together with the carbon atom to which they are bound, denote a $C_{3-7}$-cycloalkyl group, while
one of the methylene groups of the $C_{3-7}$-cycloalkyl group may be replaced by an imino, $C_{1-3}$-alkylimino, acylimino or sulphonylimino group, $R^5$ denotes a hydrogen atom or a $C_{1-3}$-alkyl group, B denotes a group of formula

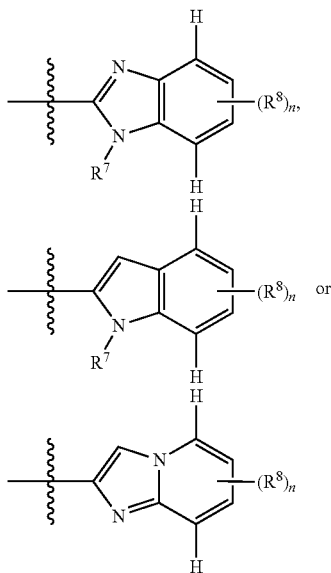

wherein
n denotes the number 1 or 2,
$R^7$ denotes a hydrogen atom or a $C_{1-3}$-alkyl, hydroxy, $C_{1-5}$-alkyloxycarbonyl, carboxy-$C_{1-3}$-alkyl, $C_{1-3}$-alkyloxycarbonyl-$C_{1-3}$-alkyl, amino or $C_{1-3}$-alkylamino group and $R^8$ independently of one another denote a hydrogen, fluorine, chlorine, bromine or iodine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy, amino, nitro or nitrile group, while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a $C_{1-3}$-alkyl, phenyl or phenyl-$C_{1-3}$-alkyl group, an oxygen or sulphur atom or
an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group or an oxygen or sulphur atom and additionally a nitrogen atom or
an imino group optionally substituted by a $C_{1-3}$-alkyl or phenyl-$C_{1-3}$-alkyl group and two or three nitrogen atoms,
and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

2. A compound of the formula I according to claim 1, wherein

A denotes a group of the formula

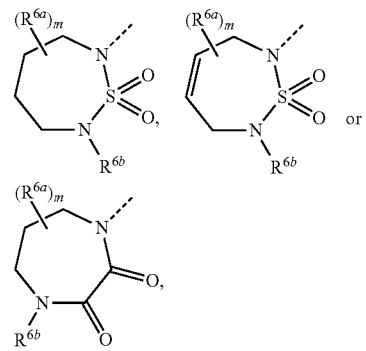

wherein m denotes the number 1 or 2, $R^{6a}$ independently of one another denote a hydrogen or fluorine atom, a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and $R^{6b}$ independently of one another may be a hydrogen atom, a $C_{1-4}$-alkyl, $C_{1-4}$-alkylcarbonyl, $C_{1-4}$-alkoxycarbonyl or $C_{1-3}$-alkylsulphonyl group, with the proviso that
in the above-mentioned substituted 7-membered groups A the heteroatoms optionally introduced as substituents are not separated from another heteroatom by precisely one carbon atom, or a group of the formula

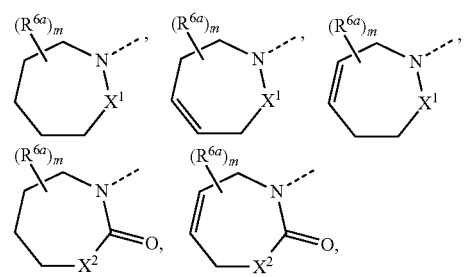

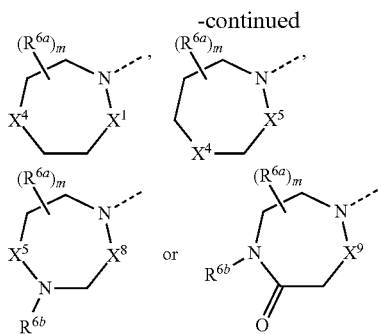

wherein m denotes the number 1 or 2, $X^1$ denotes a methylene, —$NR^{6b}$—, carbonyl or sulphonyl group, $X^2$ denotes an oxygen atom or a —$NR^{6b}$ group, $X^3$ denotes a methylene, carbonyl or sulphonyl group, $X^4$ denotes an oxygen or sulphur atom, a —$NR^{6b}$ or carbonyl group, $X^5$ denotes a carbonyl or sulphonyl group, $X^8$ denotes a carbonyl group, $X^9$ denotes a carbonyl group, $R^{6a}$ independently of one another denote a hydrogen or fluorine atom, a $C_{1-3}$-alkyl, hydroxy, amino, $C_{1-3}$-alkylamino, di-($C_{1-3}$-alkyl)-amino, aminocarbonyl, $C_{1-3}$-alkylaminocarbonyl, di-($C_{1-3}$-alkyl)-aminocarbonyl or $C_{1-3}$-alkylcarbonylamino group and $R^{6b}$ independently of one another may be a hydrogen atom, a $C_{1-4}$-alkyl, $C_{1-4}$-alkylcarbonyl, $C_{1-4}$-alkoxycarbonyl or $C_{1-3}$-alkylsulphonyl group, with the proviso that in the above-mentioned substituted 7-membered cyclic groups A the heteroatoms introduced as substituents are not separated from another heteroatom by precisely one carbon atom, $R^1$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, nitro, amino, $C_{1-3}$-alkoxy, a mono-, di- or trifluoromethoxy group, $R^2$ denotes a hydrogen, fluorine, chlorine or bromine atom or a $C_{1-3}$-alkyl group, $R^3$ denotes a $C_{2-3}$-alkenyl or $C_{2-3}$-alkynyl group or a straight-chain or branched $C_{1-6}$-alkyl group wherein the hydrogen atoms may be wholly or partly replaced by fluorine atoms, and which is optionally substituted by a nitrile, hydroxy, a $C_{1-5}$-alkyloxy group wherein the hydrogen atoms may be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxy-carbonyl-$C_{1-3}$-alkyloxy, $C_{1-8}$-alkyloxycarbonylamino, mercapto, $C_{1-3}$-alkylsulphanyl, $C_{1-3}$-alkylsulphinyl, $C_{1-3}$-alkylsulphonyl, $C_{1-3}$-alkylcarbonylamino-$C_{1-3}$-alkylsulphanyl, $C_{1-3}$-alkylcarbonylamino-$C_{1-3}$-alkylsulphinyl, $C_{1-3}$-alkylcarbonylamino-$C_{1-3}$-alkylsulphonyl, carboxy, $C_{1-3}$-alkyloxycarbonyl, allyloxycarbonyl, propargyloxycarbonyl, benzyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-5}$-alkylcarbonylamino, $C_{1-3}$-alkylsulphonylamino, N-($C_{1-3}$-alkylsulphonyl)-$C_{1-3}$-alkylamino, $C_{3-6}$-cycloalkylcarbonylamino, aminocarbonylamino, $C_{1-3}$-alkylaminocarbonylamino, di-($C_{1-3}$-alkyl)-aminocarbonylamino, a 4- to 7-membered cycloalkyleneiminocarbonylamino, benzyloxycarbonylamino, phenylcarbonylamino or guanidino group, a carboxy, aminocarbonyl, $C_{1-4}$-alkylaminocarbonyl, $C_{3-6}$-cycloalkylaminocarbonyl, di-($C_{1-3}$-alkyl)-aminocarbonyl, $C_{1-4}$-alkoxycarbonyl, $C_{4-6}$-cycloalkyleneiminocarbonyl group, a phenyl or heteroaryl, phenylcarbonyl-$C_{1-3}$-alkyl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, benzyloxy, carboxy-$C_{1-3}$-alkyloxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4- to 7-membered cycloalkyleneiminocarbonyl-$C_{1-3}$-alkoxy, carboxy, $C_{1-3}$-alkyloxycarbonyl or $C_{1-3}$-alkyloxy-carbonylamino group, a 3- to 7-membered cycloalkyl, cycloalkyleneimino, cycloalkyl-$C_{1-3}$-alkyl or cycloalkyleneimino-$C_{1-3}$-alkyl group wherein in the cyclic moiety a methylene group may be replaced by a —NH— group optionally substituted by a $C_{1-3}$-alkyl or $C_{1-3}$-alkylcarbonyl group or by an oxygen atom and wherein additionally a methylene group adjacent to the —NH—, —N($C_{1-3}$-alkylcarbonyl)- or —N($C_{1-3}$-alkyl)- group may be replaced in each case by a carbonyl or sulphonyl group, with the proviso that a cycloalkyleneimino group as hereinbefore defined wherein two nitrogen atoms are separated from one another by precisely one —$CH_2$— group is excluded, $R^4$ denotes a hydrogen atom or a $C_{1-3}$-alkyl group, $R^5$ denotes a hydrogen atom or a $C_{1-3}$-alkyl group, B denotes a group of the formula

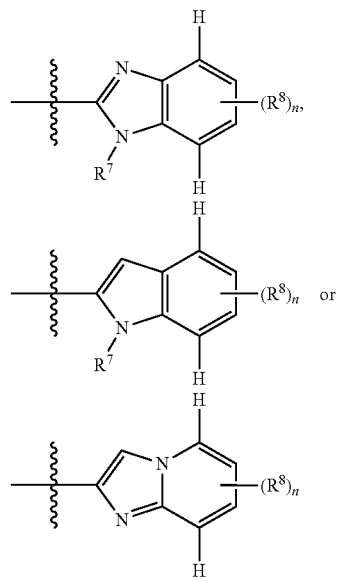

wherein
n denotes the number 1 or 2,
R$^7$ denotes a hydrogen atom, a C$_{1-3}$-alkyl, hydroxy, C$_{1-5}$-alkyloxycarbonyl, carboxy-C$_{1-3}$-alkyl, C$_{1-3}$-alkyloxycarbonyl-C$_{1-3}$-alkyl, amino or C$_{1-3}$-alkylamino group and
R$^8$ independently of one another denote a hydrogen, fluorine, chlorine, bromine or iodine atom, a C$_{1-3}$-alkyl group wherein the hydrogen atoms may be wholly or partly replaced by fluorine atoms, a C$_{2-3}$-alkenyl or C$_{2-3}$-alkynyl, a hydroxy, C$_{1-3}$-alkoxy, trifluoromethoxy, amino, nitro or nitrile group, while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a C$_{1-3}$-alkyl, phenyl or phenyl-C$_{1-3}$-alkyl group, an oxygen or sulphur atom or
an imino group optionally substituted by a C$_{1-3}$-alkyl, phenyl, amino-C$_{2-3}$-alkyl, C$_{1-3}$-alkylamino-C$_{2-3}$-alkyl, di-(C$_{1-3}$-alkyl)-amino-C$_{2-3}$-alkyl, a 4- to 7-membered cycloalkyleneimino-C$_{1-3}$-alkyl or phenyl-C$_{1-3}$-alkyl group or an oxygen or sulphur atom and additionally a nitrogen atom or
an imino group optionally substituted by a C$_{1-3}$-alkyl or phenyl-C$_{1-3}$-alkyl group and two or three nitrogen atoms,
and moreover a phenyl ring optionally substituted by a fluorine, chlorine or bromine atom, a C$_{1-3}$-alkyl, hydroxy, C$_{1-3}$-alkyloxy group, amino, C$_{1-3}$-alkylamino,
di-(C$_{1-3}$-alkyl)-amino or C$_{3-6}$-cycloalkyleneimino group may be fused to the above-mentioned monocyclic heteroaryl groups via two adjacent carbon atoms
and the bond is effected via a nitrogen atom or a carbon atom of the heterocyclic moiety or a fused-on phenyl ring,
while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
or a tautomer or salt thereof.

3. A compound of the formula I according to claim 1, wherein
A denotes a group of the formula

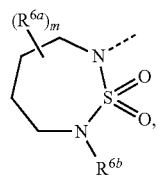

wherein m denotes the number 1 or 2,
R$^{6a}$ independently of one another denote a hydrogen or fluorine atom, a C$_{1-3}$-alkyl, hydroxy, amino, C$_{1-3}$-alkylamino, di-(C$_{1-3}$-alkyl)-amino, aminocarbonyl, C$_{1-3}$-alkylaminocarbonyl, di-(C$_{1-3}$-alkyl)-aminocarbonyl or C$_{1-3}$-alkylcarbonylamino group and
R$^{6b}$ independently of one another may be a hydrogen atom, a C$_{1-4}$-alkyl, C$_{1-4}$-alkylcarbonyl, C$_{1-4}$-alkoxycarbonyl or C$_{1-3}$-alkylsulphonyl group, with the proviso that
in the above-mentioned substituted 7-membered groups A the heteroatoms optionally introduced as substituents are not separated from another heteroatom by precisely one carbon atom, or
a group of the formula

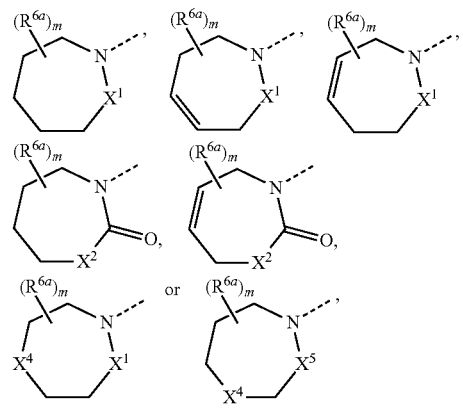

wherein
m denotes the number 1 or 2,
X$^1$ denotes a methylene, —NR$^{6b}$—, carbonyl or sulphonyl group,
X$^2$ denotes an oxygen atom or a —NR$^{6b}$ group,
X$^3$ denotes a methylene, carbonyl or sulphonyl group,
X$^4$ denotes an oxygen or sulphur atom or a —NR$^{6b}$ group,
X$^5$ denotes a carbonyl or sulphonyl group,
R$^{6a}$ independently of one another denote a hydrogen or fluorine atom, a C$_{1-3}$-alkyl, hydroxy, amino, C$_{1-3}$-alkylamino, di-(C$_{1-3}$-alkyl)-amino, aminocarbonyl, C$_{1-3}$-alkylaminocarbonyl, di-(C$_{1-3}$-alkyl)-aminocarbonyl or C$_{1-3}$-alkylcarbonylamino group and
R$^{6b}$ independently of one another may be a hydrogen atom, a C$_{1-4}$-alkyl, C$_{1-4}$-alkylcarbonyl, C$_{1-4}$-alkoxycarbonyl or C$_{1-3}$-alkylsulphonyl group, with the proviso that
in the above-mentioned substituted 7-membered cyclic groups A the heteroatoms introduced as substituents are not separated from another heteroatom by precisely one carbon atom,
R$^1$ denotes a fluorine, chlorine or bromine atom, a C$_{1-3}$-alkyl group wherein the hydrogen atoms may be wholly or partly replaced by fluorine atoms, a nitro, C$_{1-3}$-alkoxy, a mono-, di- or trifluoromethoxy group,
R$^2$ denotes a hydrogen atom,
R$^3$ denotes a straight-chain or branched C$_{1-6}$-alkyl group wherein the hydrogen atoms may be wholly or partly replaced by fluorine atoms, and which is optionally substituted by a nitrile, hydroxy, benzyloxy, a C$_{1-5}$-alkyloxy group wherein the hydrogen atoms may be wholly or partly replaced by fluorine atoms, an allyloxy, C$_{1-5}$-alkylcarbonyloxy, C$_{1-5}$-alkyloxycarbonyloxy, carboxy-C$_{1-3}$-alkyloxy, C$_{1-5}$-alkyloxycarbonyl-C$_{1-3}$-alkyloxy, C$_{1-8}$-alkyloxycarbonylamino, C$_{1-3}$-alkylsulphanyl, C$_{1-3}$-alkylsulphonyl, carboxy, C$_{1-3}$-alkyloxycarbonyl, $C_{1-3}$-alkylaminocarbonyl, di-($C_{1-3}$-alkyl)-aminocarbonyl, $C_{3-6}$-cycloalkyleneiminocarbonyl, aminocarbonylamino, $C_{1-3}$-alkylaminocarbonylamino or di-($C_{1-3}$-alkyl)-aminocarbonylamino group, an aminocarbonyl, $C_{1-4}$-alkylaminocarbonyl, $C_{3-6}$-cycloalkylaminocarbonyl or di-($C_{1-3}$-alkyl)-aminocarbonyl group, a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, carboxy, or $C_{1-3}$-alkyloxycarbonyl group, a 3- to 7-membered cycloalkyl group wherein in the cyclic moiety a methylene group may be replaced by a —NH— group optionally substituted by a $C_{1-3}$-alkyl or $C_{1-3}$-alkylcarbonyl group, or an oxygen atom, $R^4$ denotes a hydrogen atom, $R^5$ denotes a hydrogen atom, B denotes a group of the formula

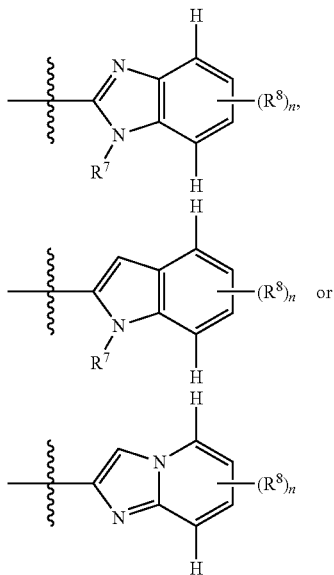

wherein n denotes the number 1, $R^7$ denotes a hydrogen atom and $R^8$ denotes a hydrogen, fluorine, chlorine, bromine or iodine atom, a methyl, $C_{2-3}$-alkynyl, or methoxy group, wherein the hydrogen atoms may be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

4. A compound of the formula I according to claim 3, wherein

A, $R^1$, $R^2$, $R^4$, $R^5$ and B are defined as in claim 3 and $R^3$ denotes a straight-chain or branched $C_{1-6}$-alkyl group wherein the hydrogen atoms may be wholly or partly replaced by fluorine atoms, and which is optionally substituted by a nitrile, hydroxy, benzyloxy, a $C_{1-5}$-alkyloxy group wherein the hydrogen atoms may be wholly or partly replaced by fluorine atoms, an allyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, $C_{1-3}$-alkylsulphanyl, $C_{1-3}$-alkylsulphonyl, carboxy, $C_{1-3}$-alkyloxycarbonyl, $C_{1-3}$-alkylaminocarbonyl, di-($C_{1-3}$-alkyl)-aminocarbonyl, $C_{3-6}$-cycloalkyleneiminocarbonyl, aminocarbonylamino, $C_{1-3}$-alkylaminocarbonylamino or di-($C_{1-3}$-alkyl)-aminocarbonylamino group, an aminocarbonyl, $C_{1-4}$-alkylaminocarbonyl, $C_{3-6}$-cycloalkylaminocarbonyl or di-($C_{1-3}$-alkyl)-aminocarbonyl group, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

5. A compound of the formula I according to claim 3, wherein

A, $R^1$, $R^2$, $R^4$, $R^5$ are defined as in claim 3 and $R^3$ denotes a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, carboxy, or $C_{1-3}$-alkyloxycarbonyl group, a 3- to 7-membered cycloalkyl group wherein in the cyclic moiety a methylene group may be replaced by a —NH— group optionally substituted by a $C_{1-3}$-alkyl or $C_{1-3}$-alkylcarbonyl group, or by an oxygen atom, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

6. A compound of the formula I according to claim 1, wherein

A denotes a group of the formula

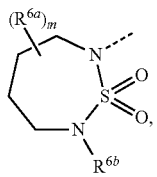

wherein m denotes the number 1 or 2, $R^{6a}$ independently of one another denote a hydrogen or fluorine atom or a $C_{1-3}$-alkyl group and $R^{6b}$ may be a hydrogen atom or a $C_{1-3}$-alkyl group, with the proviso that in the above-mentioned substituted 7 membered groups A the heteroatoms optionally introduced as substituents are not separated from another heteroatom by precisely one carbon atom, or a group of the formula

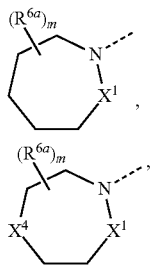 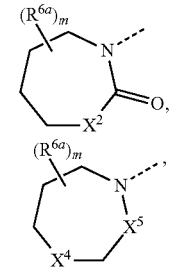

wherein m denotes the number 1 or 2, $X^1$ denotes a methylene, —$NR^{6b}$—, carbonyl or sulphonyl group, $X^2$ denotes an oxygen atom or a —$NR^{6b}$ group, $X^3$ denotes a methylene, carbonyl or sulphonyl group, $X^4$ an oxygen or sulphur atom or a —$NR^{6b}$ group, $X^5$ denotes a carbonyl or sulphonyl group, $R^{6a}$ independently of one another denote a hydrogen or fluorine atom or a $C_{1-3}$-alkyl group and $R^{6b}$ independently of one another may be a hydrogen atom or a $C_{1-3}$-alkyl group, with the proviso that in the above-mentioned substituted 7-membered cyclic groups A the heteroatoms introduced as substituents are not separated from another heteroatom by precisely one carbon atom, $R^1$ denotes a chlorine or bromine atom, a methyl or methoxy group, wherein the hydrogen atoms may be wholly or partly replaced by fluorine atoms, or a nitro group, $R^2$ denotes a hydrogen atom, $R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group, a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, $C_{1-4}$-alkyloxy, mono-, di- or trifluoromethoxy, carboxy, or $C_{1-3}$-alkyloxycarbonyl group, $R^4$ denotes a hydrogen atom, $R^5$ denotes a hydrogen atom and B denotes a group of formula

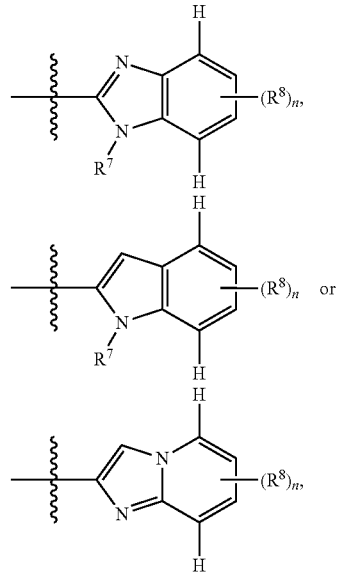

wherein n denotes the number 1, $R^7$ denotes a hydrogen atom and $R^8$ denotes a chlorine or bromine atom or the ethynyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

7. A compound of the formula I according to claim 6, wherein $A$, $R^1$, $R^2$, $R^4$, $R^5$ and B are defined as in claim 6 and $R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group, while the alkyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

8. A compound of the formula I according to claim 6, wherein $A$, $R^1$, $R^2$, $R^4$, $R^5$ and B are defined as in claim 6 and $R^3$ denotes a phenyl or heteroaryl, phenyl-$C_{1-3}$-alkyl or heteroaryl-$C_{1-3}$-alkyl group which is optionally mono- or polysubstituted in the phenyl or heteroaryl moiety by fluorine, chlorine or bromine atoms, $C_{1-3}$-alkyl, $C_{1-4}$-alkyloxy, mono-, di- or trifluoromethoxy, carboxy, or $C_{1-3}$-alkyloxycarbonyl group, a 3- to 7-membered cycloalkyl group wherein in the cyclic moiety a methylene group may be replaced by a —NH— group optionally substituted by a $C_{1-3}$-alkyl or $C_{1-3}$-alkylcarbonyl group, or by an oxygen atom, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group or an oxygen or sulphur atom and additionally a nitrogen atom or an imino group optionally substituted by a $C_{1-3}$-alkyl group and two or three nitrogen atoms, and the bond is effected via a nitrogen atom or via a carbon atom, while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, or a tautomer or salt thereof.

9. A compound of the formula I according to claim 1, wherein

A denotes a group of the formula

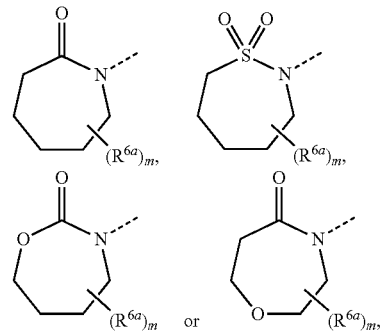

wherein m denotes the number 1 or 2, $R^{6a}$ independently of one another denote a hydrogen or fluorine atom or a $C_{1-3}$-alkyl group, with the proviso that in the above-mentioned substituted 7-membered cyclic groups A the fluorine atoms introduced as substituents are not separated from another heteroatom by precisely one carbon atom, $R^1$ denotes a chlorine or bromine atom, a methyl or methoxy group, wherein the hydrogen atoms may be wholly or partly replaced by fluorine atoms, or a nitro group, $R^2$ denotes a hydrogen atom, $R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group, a furanyl, thiophenyl, pyrrolyl, pyrazolyl, imidazolyl, oxazolyl, isoxazolyl, thiazolyl, pyridinyl, pyrimidinyl, pyrazinyl, pyridinyl-$C_{1-2}$-alkyl or imidazolyl-$C_{1-2}$-alkyl group which may optionally be substituted in the heteroaryl moiety by one or two $C_{1-3}$-alkyl groups, $C_{1-3}$-alkyloxy groups, carboxy or $C_{1-3}$-alkyloxycarbonyl groups, and $R^4$ denotes a hydrogen atom, $R^5$ denotes a hydrogen atom and B denotes a group of the formula

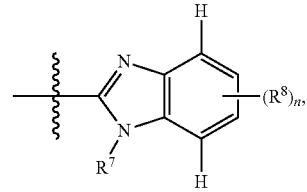

-continued

[chemical structure with (R⁸)ₙ and R⁷]

or

[chemical structure with (R⁸)ₙ]

wherein
n denotes the number 1,
R⁷ denotes a hydrogen atom and
R⁸ denotes a chlorine or bromine atom or an ethynyl group,
while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a $C_{1-3}$-alkyl group, an oxygen or sulphur atom or
an imino group optionally substituted by a $C_{1-3}$-alkyl group or an oxygen or sulphur atom and additionally a nitrogen atom or
an imino group optionally substituted by a $C_{1-3}$-alkyl group and two or three nitrogen atoms,
and the bond is effected via a nitrogen atom or via a carbon atom,
while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
or a tautomer or salt thereof.

10. A compound of the formula I according to claim 9, wherein
A, $R^1$, $R^2$, $R^4$, $R^5$ and B are defined as in claim 9 and
$R^3$ denotes a straight-chain or branched $C_{1-4}$-alkyl group wherein the hydrogen atoms may be wholly or partly replaced by fluorine atoms, and which is optionally substituted by a hydroxy, a $C_{1-4}$-alkyloxy group wherein the hydrogen atoms may be wholly or partly replaced by fluorine atoms, a $C_{1-3}$-alkylsulphanyl, $C_{1-3}$-alkylsulphonyl, carboxy or $C_{1-3}$-alkyloxycarbonyl group,
while the alkyl and alkoxy groups contained in the abovementioned definitions which have more than two carbon atoms may, unless otherwise stated, be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
or a tautomer or salt thereof.

11. A compound of the formula I according to claim 9, wherein
A, $R^1$, $R^2$, $R^4$, $R^5$ and B are defined as in claim 9 and
denote a furanyl, thiophenyl, pyrrolyl, pyrazolyl, imidazolyl, oxazolyl, isoxazolyl, thiazolyl, pyridinyl, pyrimidinyl, pyrazinyl, pyridinyl-$C_{1-2}$-alkyl or imidazolyl-$C_{1-2}$-alkyl group which may optionally be substituted in the heteroaryl moiety by one or two $C_{1-3}$-alkyl groups, wherein the hydrogen atoms may be wholly or partly replaced by fluorine atoms, $C_{1-3}$-alkyloxy groups, wherein the hydrogen atoms may be wholly or partly replaced by fluorine atoms, carboxy or $C_{1-3}$-alkyloxycarbonyl groups, and
unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a $C_{1-3}$-alkyl group, an oxygen or sulphur atom or
an imino group optionally substituted by a $C_{1-3}$-alkyl group or an oxygen or sulphur atom and additionally a nitrogen atom or
an imino group optionally substituted by a $C_{1-3}$-alkyl group and two or three nitrogen atoms,
and the bond is effected via a nitrogen atom or via a carbon atom,
while the alkyl groups contained in the foregoing definitions which have more than two carbon atoms may, unless otherwise stated, be straight-chain or branched and the alkyl groups in the previously mentioned dialkylated groups, for example the dialkylamino groups, may be identical or different,
and the hydrogen atoms of the methyl or ethyl groups contained in the foregoing definitions may be wholly or partly replaced by fluorine atoms,
or a tautomer or salt thereof.

12. A compound of the formula I according to claim 1, wherein the group $X^1$ denotes a methylene group.

13. A compound of the formula I according to claim 1, wherein the group $X^1$ denotes a carbonyl group.

14. A compound of the formula I according to claim 1, wherein the group $X^3$ denotes a methylene group.

15. A compound of the formula I according to claim 1 wherein the group $X^3$ denotes a carbonyl group.

16. A compound of the formula I according to claim 1, wherein the group $X^4$ denotes an oxygen atom.

17. A compound of the formula I according to claim 1, wherein the group B denotes the group

[chemical structure with (R⁸)ₙ and R⁷]

18. A compound of the formula I according to claim 1, wherein the group B denotes the group

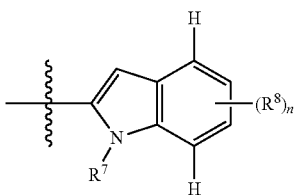

19. A compound of the formula I according to claim 1, wherein the group B denotes the group

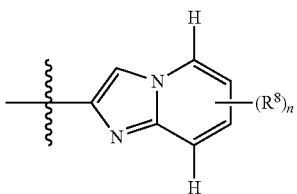

20. A compound of the formula I according to claim 1, wherein the group $R^8$ denotes a chlorine atom.

21. A compound of the formula I according to claim 1, wherein the group $R^8$ denotes a bromine atom.

22. A compound of the formula I according to claim 1, wherein the group $R^8$ denotes an ethynyl group.

23. A compound according to claim 1, having the formula Ia

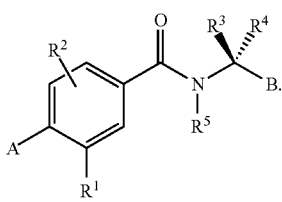

24. A compound according to claim 1 selected from the group consisting of:

(1) 4-(azepan-2-on-1-yl)-N-[(1R)-1-(5-chloro-1H-benzimidazol-2-yl)-2-methoxy-ethyl]-3-methyl-benzamide, (2) 4-(azepan-2-on-1-yl)-N-[(1R)-1-(5-chloro-1H-benzimidazol-2-yl)-2-hydroxy-ethyl]-3-methyl-benzamide, (8) 4-(azepan-2-on-1-yl)-3-chloro-N-[(1R)-1-(5-chloro-1H-benzimidazol-2-yl)-2-methoxy-ethyl]-benzamide, (9) 4-(azepan-2-on-1-yl)-N-[(1R)-1-(5-chloro-1H-benzimidazol-2-yl)-2-methoxy-ethyl]-3-trifluoromethyl-benzamide,

(10) N-[(1S)-1-(5-chloro-1H-benzimidazol-2-yl)-ethyl]-3-methyl-4-([1,3]oxazepan-2-on-3-yl)-benzamide

(12) N-[(1R)-1-(5-chloro-1H-benzimidazol-2-yl)-2-methoxy-ethyl]-3-methyl-4-([1,3]oxazepan-2-on-3-yl)-benzamide,

(13) 3-chloro-N-[(1R)-1-(5-chloro-1H-benzimidazol-2-yl)-2-methoxy-ethyl]-4-([1,4]oxazepan-5-on-4-yl)-benzamide,

(23) N-[(1R)-1-(5-chloro-1H-benzimidazol-2-yl)-2-methoxy-ethyl]-4-([1,3]oxazepan-2-on-3-yl)-3-trifluoromethyl-benzamide,

(32) N-[(1R)-1-(5-chloro-1H-benzimidazol-2-yl)-2-methoxy-ethyl]-4-(1,1-dioxo-[1,2]thiazepan-2-yl)-3-methyl-benzamide, or a tautomer or salt thereof.

25. A physiologically acceptable salt of a compound according to claim 1.

26. A pharmaceutical composition comprising a compound according to claim 1, or a physiologically acceptable salt thereof, together with one or more inert carriers and/or diluents.

27. A method for inhibiting factor Xa or a related serine protease selected from urokinase, factor VIIa, factor IXa, Factor XIa and factor XIIa which comprises administering an inhibitory amount of a compound in accordance with claim 1 or a physiologically acceptable salt thereof.

* * * * *